(12) United States Patent
Klaerner et al.

(10) Patent No.: US 7,205,161 B2
(45) Date of Patent: Apr. 17, 2007

(54) POLYMER BRUSHES FOR IMMOBILIZING MOLECULES TO A SURFACE OR SUBSTRATE HAVING IMPROVED STABILITY

(75) Inventors: Gerrit Klaerner, Campbell, CA (US); Didier Benoit, San Jose, CA (US); Dominique Charmot, Los Gatos, CA (US); Srinivas Nomula, San Jose, CA (US); Marcelo Eduardo Piotti, San Jose, CA (US); Laura T. Mazzola, Redwood City, CA (US)

(73) Assignee: Symyx Technologies, Inc., Santa Clara, CA (US)

(*) Notice: Subject to any disclaimer, the term of this patent is extended or adjusted under 35 U.S.C. 154(b) by 762 days.

(21) Appl. No.: 10/043,394

(22) Filed: Jan. 10, 2002

(65) Prior Publication Data
US 2003/0108879 A1    Jun. 12, 2003

Related U.S. Application Data

(60) Provisional application No. 60/271,692, filed on Jan. 10, 2001.

(51) Int. Cl.
*G01N 33/545* (2006.01)
*G01N 33/552* (2006.01)
*C07K 17/08* (2006.01)

(52) U.S. Cl. .................... 436/531; 435/6; 436/527; 436/532; 530/391.1; 530/402; 530/404; 530/405; 530/406

(58) Field of Classification Search ............... 435/6; 436/531, 532, 527; 530/391.1, 402, 404, 530/405, 406
See application file for complete search history.

(56) References Cited

U.S. PATENT DOCUMENTS

| | | |
|---|---|---|
| 4,581,429 A | 4/1986 | Solomon et al. |
| 4,946,778 A | 8/1990 | Ladner et al. |
| 4,973,493 A | 11/1990 | Guire |
| 5,002,582 A | 3/1991 | Guire et al. |
| 5,030,697 A | 7/1991 | Hugl et al. |
| 5,126,021 A | 6/1992 | Grossman |
| 5,143,854 A | 9/1992 | Pirrung et al. |
| 5,217,492 A | 6/1993 | Guire et al. |
| 5,240,602 A | 8/1993 | Hammen |
| 5,258,454 A | 11/1993 | Berg et al. |
| 5,424,186 A | 6/1995 | Fodor et al. |
| 5,436,327 A | 7/1995 | Southern et al. |
| 5,445,934 A | 8/1995 | Fodor et al. |
| 5,480,723 A | 1/1996 | Klainer et al. |
| 5,512,329 A | 4/1996 | Guire et al. |
| 5,512,439 A | 4/1996 | Hornes et al. |
| 5,530,079 A | 6/1996 | Veregin et al. |
| 5,539,082 A | 7/1996 | Nielsen et al. |
| 5,624,711 A | 4/1997 | Sundberg et al. |
| 5,677,195 A | 10/1997 | Winkler et al. |
| 5,700,637 A | 12/1997 | Southern |
| 5,744,305 A | 4/1998 | Fodor et al. |
| 5,753,439 A | 5/1998 | Smith et al. |
| 5,770,456 A | 6/1998 | Holmes |
| 5,800,992 A | 9/1998 | Fodor et al. |
| 5,807,522 A | 9/1998 | Brown et al. |
| 5,824,473 A | 10/1998 | Maede et al. |
| 5,837,832 A | 11/1998 | Chee et al. |
| 5,843,655 A | 12/1998 | McGall |
| 5,846,724 A | 12/1998 | Bensimon et al. |
| 5,858,653 A | 1/1999 | Duran et al. |
| 5,868,938 A | 2/1999 | Bomer et al. |
| 5,872,003 A | 2/1999 | Koster |
| 5,902,723 A | 5/1999 | Dower et al. |
| 5,919,523 A | 7/1999 | Sundberg et al. |
| 5,919,626 A | 7/1999 | Shi et al. |
| 5,932,711 A | 8/1999 | Boles et al. |
| 5,942,555 A | 8/1999 | Swanson et al. |
| 5,998,140 A | 12/1999 | Dervan et al. |
| 6,004,755 A | 12/1999 | Wang |
| 6,013,440 A | 1/2000 | Lipshutz et al. |
| 6,018,041 A | 1/2000 | Drmanac et al. |
| 6,027,880 A | 2/2000 | Cronin et al. |

(Continued)

FOREIGN PATENT DOCUMENTS

EP    0 205 232 A1    12/1986

(Continued)

OTHER PUBLICATIONS

A. Sidorenko et al, Langmuir (91999), vol. 15, pp. 8349-8355. Switching of Polymer Brushes.*

(Continued)

*Primary Examiner*—Mary E. Ceperley
(74) *Attorney, Agent, or Firm*—Senniger Powers

(57) ABSTRACT

Sensors for determining the presence and concentration of biomolecules in a biological sample are provided in the form of polymer brushes, which comprise a substrate having a surface modified with a hydrophobic polymer segment, attached to which is a water-dispersible or water-soluble polymer segment having functional groups that bind probes. The method of synthesis of such sensors preferably includes use of controlled free radical polymerization techniques, which allows for controlled architecture polymers to modify the surface of the substrate, and the use of monomers possessing functional groups which do not require activation prior to probe attachment. In this manner functional groups in the polymer chain are removed from the surface, which allows for solution chemistry to be more realistically reproduced with the benefits of a solid bound probe.

33 Claims, 11 Drawing Sheets

U.S. PATENT DOCUMENTS

| | | | |
|---|---|---|---|
| 6,040,138 | A | 3/2000 | Lockhart et al. |
| 6,040,193 | A | 3/2000 | Winkler et al. |
| 6,043,080 | A | 3/2000 | Lipshutz et al. |
| 6,045,996 | A | 4/2000 | Cronin et al. |
| 6,054,270 | A | 4/2000 | Southern |
| 6,057,100 | A | 5/2000 | Heyneker |
| 6,077,674 | A | 6/2000 | Schleifer et al. |
| 6,083,697 | A | 7/2000 | Beecher et al. |
| 6,087,102 | A | 7/2000 | Chenchik et al. |
| 6,087,112 | A | 7/2000 | Dale |
| 6,087,186 | A | 7/2000 | Cargill et al. |
| 6,100,026 | A | 8/2000 | Nova et al. |
| 6,475,808 | B1 * | 11/2002 | Wagner et al. ............... 436/518 |
| 6,833,276 | B2 * | 12/2004 | Klaerner et al. ............ 436/532 |
| 2002/0001845 | A1 * | 1/2002 | Klaerner et al. ................ 436/8 |

FOREIGN PATENT DOCUMENTS

| | | |
|---|---|---|
| EP | 0 361 229 A2 | 7/1991 |
| EP | 0 780 408 A2 | 2/1999 |
| EP | 1 035 218 A1 | 9/2000 |
| EP | 1 081 163 A1 | 3/2001 |
| EP | 1 095 711 A2 | 5/2001 |
| WO | WO 89/02449 A1 | 3/1989 |
| WO | WO 90/05303 A1 | 5/1990 |
| WO | WO 96/00251 A1 | 1/1996 |
| WO | WO 96/24620 A1 | 8/1996 |
| WO | WO 97/41425 A1 | 11/1997 |
| WO | WO 98/30601 A2 | 7/1998 |
| WO | WO 99/03894 A1 | 1/1999 |
| WO | WO 99/06425 A1 | 2/1999 |
| WO | WO 99/36571 A2 | 7/1999 |
| WO | WO 99/61653 A2 | 12/1999 |
| WO | WO 00/33078 A1 | 6/2000 |
| WO | WO 00/33084 A2 | 6/2000 |
| WO | WO 00/43539 A2 | 7/2000 |
| WO | WO 00/65352 A1 | 11/2000 |

OTHER PUBLICATIONS

Wagner et al, HCAPLUS abstract 2002: 845515 (Abstract of U.S. Patent No. 6,475,808).*

Y-C. Chang et al. "Surface Initiated Polymerization of Polyglutamate Copolymers" Abstract 304, Presented at the 209th ACS National Meeting in Anaheim, CA (Apr. 2-7, 1995).

Y-C. Chang et al. "Surface Initiated Polymerization of Polyglutamate Copolymers" American Chemical Society, Polymer Preprints, vol. 36, No. 1 (Apr. 1995).

Y-C. Chang et al. "Surface Polymerization of Poly(2-hydroxy ethyl methacrylate) for High Density DNA Arrays" Max-Planck-Institute for Polymer Research—Center on Polymer Interfaces and Macromolecular Assemblies forum, Mainz, Germany (Apr. 26-27, 1999).

Y-C. Chang et al. "Surface Polymerization of Poly(y-Alkyl-L-Glutamate) on Solid Substrates" Macromolecular Symposia, vol. 118 (1997) pp. 641-646.

Y-C. Chang Website at The Henry Samueli School of Engineering, homepage (2 pages) and Publications List (5 pages) printed Sep. 17, 2002.

Ingall et al. "Surface Functionalization with Polymer and Block Copolymer Films Using Organometallic Initiators" J. Am. Chem. Soc., vol. 122, No. 32 (2000) pp. 7845-7846.

International Search Report for analogous application No. PCT/US02/00746 dated Apr. 29, 2003.

Anders et al. "Surface Modification with Hydrogels via Macroinitiators for Enhanced Friction Properties of Biomaterials" J.M.S.—Pure Appl. Chem. vol. A36, Nos. 7&8 (1999) pp. 1017-1029.

Baker et al. "Structure of Polymer Brushes Under Shear Flow in a Good Solvent" Macromolecules, vol. 33, No. 4 (2000) pp. 1120-1122.

Benoit et al. "Development of a Universal Alkoxyamine for "Living" Free Radical Polymerizations" Journal of the American Chemical Society, vol. 121, No. 16 (1999) pp. 3904-3920.

Bergbreiter et al. "Meisenheimer Rearrangement of Allyl N-Oxides as a Route to Initiators for Nitroxide-Mediated "Living" Free Radical Polymerizations" Macromolecules, vol. 31, No. 18 (1998) pp. 6380-6382.

Biesalski et al. "Preparation and Characterization of a Polyelectrolyte Monolayer Covalently Attached to a Planar Solid Surface" Macromolecules, vol. 32, No. 7 (1999) pp. 2309-2316.

Boven et al. "Radical Grafting of Poly(methyl methacrylate) onto Silicon Wafers, Glass Slides and Glass Beads" Polymer Communications, vol. 32, No. 2 (1991) pp. 50-53.

Chan et al. "The Biophysics of DNA Hybridization with Immobilized Oligonucleotide Probes" Biophysical Journal, vol. 69, No. 6 (1995) pp. 2243-2255.

Cheung et al. "Making and Reading Microarrays" Nature Genetics Supplement, vol. 21 (Jan. 1999) pp. 15-19.

Cole et al. "The EBV-Hybridoma Technique and Its Application to Human Lung Cancer" Monoclonal Antibodies and Cancer Therapy, Alan R. Liss, Inc. (1985) pp. 77-96.

Cote et al. "Generation of Human Monoclonal Antibodies Reactive with Cellular Antigens" Proceedings of the National Academy of Sciences vol. 80, No. 7 (Apr. 1983) pp. 2026-2030.

de Boer et al. ""Living" Free Radical Photopolymerization Initiated form Surface-Grafted Iniferter Monolayers" Macromolecules, vol. 33, No. 2 (2000) pp. 349-356.

Dhar et al. "Modification of Silica Surfaces Using Surface Initiated Polymerization" Abstracts of Papers, Part 2, 215th ACS National Meeting, Dallas, TX (1998) Abstract No. 147.

Fischer "The Persistent Radical Effect In "Living" Radical Polymerization" Macromolecules, vol. 30, No. 19 (1997) pp. 5666-5672.

Glazer "Phycobilisomes: Structure and Dynamics" Annual Review of Microbiology, vol. 36 (1982) pp. 173-198.

Grabarek et al. "Zero-Length Crosslinking Procedure with the Use of Active Esters" Analytical Biochemistry, vol. 185 (1990) pp. 131-135.

Harrison et al. "Reducing Substrate Pinning of Block Copolymer Microdomains with a Buffer Layer of Polymer Brushes" Macromolecules, vol. 33, No. 3 (2000) pp. 857-865.

Hawker et al. "Accurate Control of Chain Ends by a Novel "Living" Free-Radical Polymerization Process" Macromolecules, vol. 28, No. 8 (1995) pp. 2993-2995.

Hawker "Architectural Control in "Living" Free Radical Polymerizations: Preparation of Star and Graft Polymers" Angew. Chem. Int. Ed. Engl., vol. 34, No. 13/14 (1995) pp. 1456-1459.

Hawker et al. "Initiating Systems for Nitroxide-Mediated "Living" Free Radical Polymerizations: Synthesis and Evaluation" Macromolecules, vol. 29, No. 16 (1996) pp. 5245-5254.

Hawker et al. "Manipulation of Surface Properties Using Novel Grafted Copolymer Brushes and Surface Initiated Polymerization" Polymer Preprints, vol. 40, No. 2 (Aug. 1999) p. 101.

Hawker et al. "Manipulation of Surface Properties Using Novel Grafted Copolymer Brushes and Surface-Initiated Polymerization" 218th ACS National Meeting, Abstracts of Papers, Part 2, New Orleans, LA (Aug. 1999) Abstract 345-Poly.

Hawker et al. "Synthesis and Application of Functionalized Specialty Polymers Using 'Living' Free Radical Procedures" Polymer Preprints, vol. 39, No. 1 (Mar. 1998) pp. 626-627.

Hendrickson et al. "Crystal Structure of Core Streptavidin Determined from Multiwavelength Anomalous Diffraction of Synchrotron Radiation" Proceedings of the National Academy of Sciences USA, vol. 86, No. 7 (Apr. 1989) pp. 2190-2194.

Hertler et al. "Group-Transfer Polymerization on a Polymeric Support" Macromolecules, vol. 23, No. 5 (1990) pp. 1264-1268.

Higashi et al. "High-Spatioresolved Microarchitectural Surface Prepared by Photograft Copolymerization Using Dithiocarbamate: Surface Preparation and Cellular Responses" Langmuir, vol. 15, No. 6 (1999) pp. 2080-2088.

Hodges et al. "Preparation of Designer Resins via Living Free Radical Polymerization of Functional Monomers on Solid Support" J. Comb. Chem., vol. 2, No. 1 (2000) pp. 80-88.

Hosoya et al. "In Situ Surface-Selective Modification of Uniform Size Macroporous Polymer Particles with Temperature-Responsive Poly-N-isopropylacrylamide" Macromolecules, vol. 27, No. 14 (1994) pp. 3973-3976.

Huang et al. "Mixed Lamellar Films: Evolution, Commensurability Effects, and Preferential Defect Formation" Macromolecules, vol. 33, No. 1 (2000) pp. 80-88.

Huang et al. "Neutrality Conditions for Block Copolymer Systems on Random Copolymer Brush Surfaces" Macromolecules, vol. 32, No. 16 (1999) pp. 5299-5303.

Huang et al. "Surface-Initiated Radical Polymerization on Porous Silica" Analytical Chemistry, vol. 69, No. 22 (1997) pp. 4577-4580.

Huang et al. "Surface Initiation of Living Radical Polymerization for Growth of Tethered Chains of Low Polydispersity" Macromolecules, vol. 32, No. 5 (1999) pp. 1694-1696.

Huang et al. "Using Surface Active Random Copolymers to Control the Domain Orientation in Diblock Copolymer Thin Films" Macromolecules, vol. 31, No. 22 (1998) pp. 7641-7650.

Huse et al. "Generation of a Large Combinatorial Library of the Immunoglobulin Repertoire in Phage Lambda" Science, vol. 246, No. 4935 (Dec. 1989) pp. 1275-1281.

Husseman et al. "Controlled Synthesis of Polymer Brushes by "Living" Free Radical Polymerization Techniques" Macromolecules, vol. 32, No. 5 (1999) pp. 1424-1431.

Husemann et al. "Manipulation of Surface Properties by Patterning of Covalently Bound Polymer Brushes" Journal of the American Chemical Society, vol. 122, No. 8 (2000) pp. 1844-1845.

Husemann et al. "Surface-Initiated Polymerization for Amplication of Self-Assembled Mono-layers Patterned by Microcontact Printing" Angew. Chem. Int. Ed., vol. 38, No. 5 (1999) pp. 647-649.

Jordan et al. "Surface Initiated Living Cationic Polymerization of 2-Oxazolines" Journal of the American Chemical Society, vol. 120, No. 2 (Jan. 1998) pp. 243-247.

Kohler et al. "Continuous Cultures of Fused Cells Secreting Antibody of Predefined Specificity" Nature, vol. 256, No. 5517 (Aug. 1975) pp. 495-497.

Kozbor et al. "The Production of Monoclonal Antibodies from Human Lymphocytes" Immunology Today, vol. 4, No. 3 (1983) pp. 72-79.

Laschitsch et al. "Thickness Dependence of the Solvent-Induced Glass Transition in Polymer Brushes" Macromolecules, vol. 32, No. 4 (1999) pp. 1244-1251.

Lee et al. "Surface Photograft Polymerization on Segmented Polyurethane Using the Iniferter Technique" Journal of Biomedical Materials Research, vol. 47, No. 4 (1999) pp. 564-567.

Li et al. "Mono- and Dinitroxide Styrene Polymerization Initiators" Macromolecules, vol. 29, No. 26 (1996) pp. 8554-8555.

Lockhart et al. "Expression Monitoring by Hybridization to High-Density Oligonucleotide Arrays" Nature Biotechnology, vol. 14, No. 13 (1996) pp. 1675-1680.

Lueking et al. "Protein Microarrays for Gene Expression and Antibody Screening" Analytical Biochemistry, vol. 270, No. 1 (1999) pp. 103-111.

Malmstrom et al. "Development of a New Class of Rate-accelerating Additives for Nitroxide-Mediated 'Living' Free Radical Polymerization" Tetrahedron Letters, vol. 53, No. 45 (1997) pp. 15225-15236.

Malmstrom et al. "Macromolecular Engineering via 'living' Free Radical Polymerizations" Macromol. Chem. Phys. vol. 199, No. 6 (Jun. 1998) pp. 923-935.

Mansky et al. "Controlling Polymer-Surface Interactions with Random Copolymer Brushes" Science, vol. 275, (Mar. 1997) pp. 1458-1460.

Mansky et al. "Ordered Diblock Copolymer Films on Random Copolymer Brushes" Macromolecules, vol. 30, No. 22 (1997) pp. 6810-6813.

Maty Jaszewski et al. "Polymers at Interfaces: Using Atom Transfer Radical Polymerization in the Controlled Growth of Homopolymers and Block Copolymers from Silicon Surfaces in the Absence of Untethered Sacrificial Initiator" Macromolecules, vol. 32, No. 26 (1999) pp. 8716-8724.

Maty Jaszewski et al. "Simple and Efficient Synthesis of Various Alkoxyamines for Stable Free Radical Polymerization" Macromolecules, vol. 31, No. 17 (1998) pp. 5955-5957.

McGall et al. "The Efficiency of Light-Directed Synthesis of DNA Arrays on Glass Substrates" Journal of the American Chemical Society, vol. 119, No. 22 (Jun. 1997) pp. 5081-5090.

Meier et al. "Polymerization of Styrene with Initiator Ionically Bound to High Surface Area Mica: Grafting via an Unexpected Mechanism" vol. 27, No. 6 (1994) pp. 1637-1641.

Nakayama et al. "Preparation of Poly(ethylene glycol)-polystyrene Block Copolymers Using Photochemistry of Dithiocarbamate as a Reduced Cell-Adhesive Coating Material" Biomaterials, vol. 20 (1999) pp. 963-970.

Nakayama et al. "Surface Macromolecular Architectural Designs Using Photo-Graft Copolymerization Based on Photochemistry of Benzyl $N,N$-Diethyldithiocarbamate" Macromolecules, vol. 29, No. 27 (1996) pp. 8622-8630.

Nakayama et al. "Surface Macromolecular Microarchitecture Design: Biocompatible Surfaces via Photo-Block-Graft-Copolymerization Using $N,N$-Diethyldithiocarbamate" Langmuir, vol. 15, No. 17 (1999) pp. 5560-5566.

OTSU "Iniferter Concept and Living Radical Polymerization" Journal of Polymer Science, Part A: Polymer Science, vol. 38 (2000) pp. 2121-2136.

OTSU et al. "Solid-Phase Block Copolymer Synthesis by the Iniferter Technique" vol. 19, No. 7 (1986) pp. 2087-2089.

Peng et al. "Polymer Brushes with Liquid Crystalline Side Chains" Macromolecules, vol. 32, No. 20 (1999) pp. 6759-6766.

Petro et al. "Polymers Immobilized on Silica Gels as Stationary Phases for Liquid Chromatography" Chromatographia, vol. 37, No. 9-10 (Nov. 1993) pp. 549-561.

Prucker "Grafting of Polymers to Microparticulate Silica by Using Immobilized Azo Initiators" Chemical Abstracts, vol. 123, No. 18 (1995) Abstract No. 123; 229210z.

Prucker et al. "Mechanism of Radical Chain Polymerizations Initiated by Azo Compounds Covalently Bound to the Surface of Spherical Particles" Macromolecules, vol. 31, No. 3 (1998) pp. 602-613.

Prucker "Synthesis of Poly(styrene) Monolayers Attached to High Surface Area Silica Gels Through Self-Assembled Monolayers of Azo Initiators" Macromolecules, vol. 31, No. 3 (1998) pp. 592-601.

Ruhe "Polymers Grafted From Solid Surfaces" Macromol. Symp., vol. 126 (1997) pp. 215-222.

Sarin et al. "Inhibition of Acquired Immunodeficiency Syndrome Virus by Oligodeoxynucleoside Methylphosphonates" Proceedings of the National Academy of Sciences USA, vol. 85, No. 20 (Oct. 1988) pp. 7448-7451.

Seery et al. "Designing Polymer Surfaces on Gold and Glass Using Surface Initiated Polymerizations" 214th ACS National Meeting, Los Vegas, NV (1997) Abstract 044.

Seery et al. "Direct Synthesis of Polymer Brushes" Polymer Preprints, vol. 40, No. 2 (1999) pp. 148-149.

Seidel et al. "Individual Polymer Paths and End-Point Stretching in Polymer Brushes" Macromolecules, vol. 33, No. 2 (2000) pp. 634-640.

Semenov et al. "Collective Dynamics of Polymer Brushes" Macromolecules, vol. 33, No. 2 (2000) pp. 613-623.

Shah et al. "Using Atom Transfer Radical Polymerization to Amplify Monolayers of Initiators Patterned by Microcontact Printing into Polymer Brushes for Pattern Transfer" Macromolecules, vol. 33, No. 2 (2000) pp. 597-605.

Sidorenko et al. "Radical Polymerization Initiated from a Solid Substrate. 3. Grafting from the Surface of an Ultafine Powder" Macromolecules, vol. 32, No. 14 (1999) pp. 4539-4543.

Southern et al. "Molecular Interactions on Microarrays" Nature Genetics Supplement, vol. 21 (Jan. 1999) pp. 5-9.

Stein et al. "Physicochemical Properties of Phosphorothioate Oligodeoxynucleotides" Nucleic Acids Research, vol. 16, No. 8 (1988) pp. 3209-3221.

Sugawara et al. "Novel Surface Graft Copolymerization Method With Micron-Order Regional Precision" Macromolecules, vol. 27, No. 26 (1994) pp. 7809-7814.

Theato et al. "Stabilization of Lipid Bilayers on Surfaces Through Charged Polymers" J.M.S.—Pure Appl. Chem., vol. A36, No. 7&8 (1999) pp. 1001-1015.

Tovar et al. "Patterning Molecularly Thin Films of Polymers—New Methods for Photolithographic Structuring of Surfaces" Supramolecular Science, vol. 2, No. 2 (1995) pp. 89-98.

Tsubokawa et al. "Effect of Initiating Groups Introduced onto Ultrafine Silica on the Molecular Weight Polystyrene Grafted onto the Surface" Polymer Bulletin, vol. 31, No. 4 (1993) pp. 457-464.

Tsubokawa et al. "Effect of polymerization conditions on the molecular weight of polystyrene grafted onto silica in the radical graft polymerization initiated by azo or peroxyester groups introduced onto the surface" Colloid & Polymer Science, vol. 273, No. 11 (1995) pp. 1049-1054.

Tsubokawa et al. "Surface Grafting of Polymers onto Carbon Thin Film" Journal of Applied Polymer Science, vol. 58, No. 8 (Nov. 21, 1995) pp. 1221-1227.

Tsubokawa et al. "Surface Grafting of Polymers onto Glass Plate: Polymerization of Vinyl Monomers Initiated by Initiating Groups Introduced onto the Surface" Journal of Applied Polymer Science, vol. 65 (1997) pp. 2165-2172.

Tsubokawa et al. "Surface Modification of Carbon Microbead by the Grafting of Polymers" J.M.S.—Pure Appl. Chem., vol. A32, No. 3 (1995) pp. 525-535.

Vatansever et al. "Modification of Glass Surfaces by Using Tethered Romp Catalysts" 215th ACS National Meeting, Dallas, TX (1998) Abstract 146.

Wang et al. "Facile Synthesis of New Unimolecular Initiators for Living Radical Polymerizations" Macromolecules, vol. 31, No. 19 (1998) pp. 6727-6729.

Weck et al. "Ring-Opening Metathesis Polymerization from Surfaces" Journal of the American Chemical Society, vol. 121, No. 16 (1999) pp. 4088-4089.

Weisenhorn et al. "Imaging Single-Stranded DNA, Antigen-Antibody Reaction and Polymerized Langmuir-Blodgett Films with an Atomic Force Microscope" Scanning Microscopy, vol. 4, No. 3 (1990) pp. 511-516.

Williams et al. "A New Mechanism Involving Cyclic Tautomers for the Reaction with Nucleophiles of the Water-Soluble Peptide Coupling Reagent 1-Ethyl-3-(3-dimethylamino)propyl)carbodiimide (EDC)" Journal of the American Chemical Society, vol. 103, No. 24 (1981) pp. 7090-7095.

Xia et al. "Soft Lithography" Angew. Chem. Int. Ed., vol. 37 (1998) pp. 550-575.

Yamamoto et al. "Preparation of Well-Defined Polymer Brushes on Silicon Substrate by the Surface-Initiated ATRP Technique and Their Characterization" Polymer Preprints, vol. 40, No. 2 (1999) pp. 401-402.

Yin et al. "Grafting of Poly(Acrylic Acid) onto Nonporous Glass Bead Surfaces" Polymers for Advanced Technologies, vol. 8(1997) pp. 761-766.

International Search Report for PCT/US00/18339 dated Sep. 6, 2000.

J. Ward et al. "UV free-radical polymerization for micropatterning poly(ethylene glycol)-containing films" Proceedings of SPIE—The International Soc. for Optical Engineering, vol. 4097 (2000) pp. 221-228.

* cited by examiner

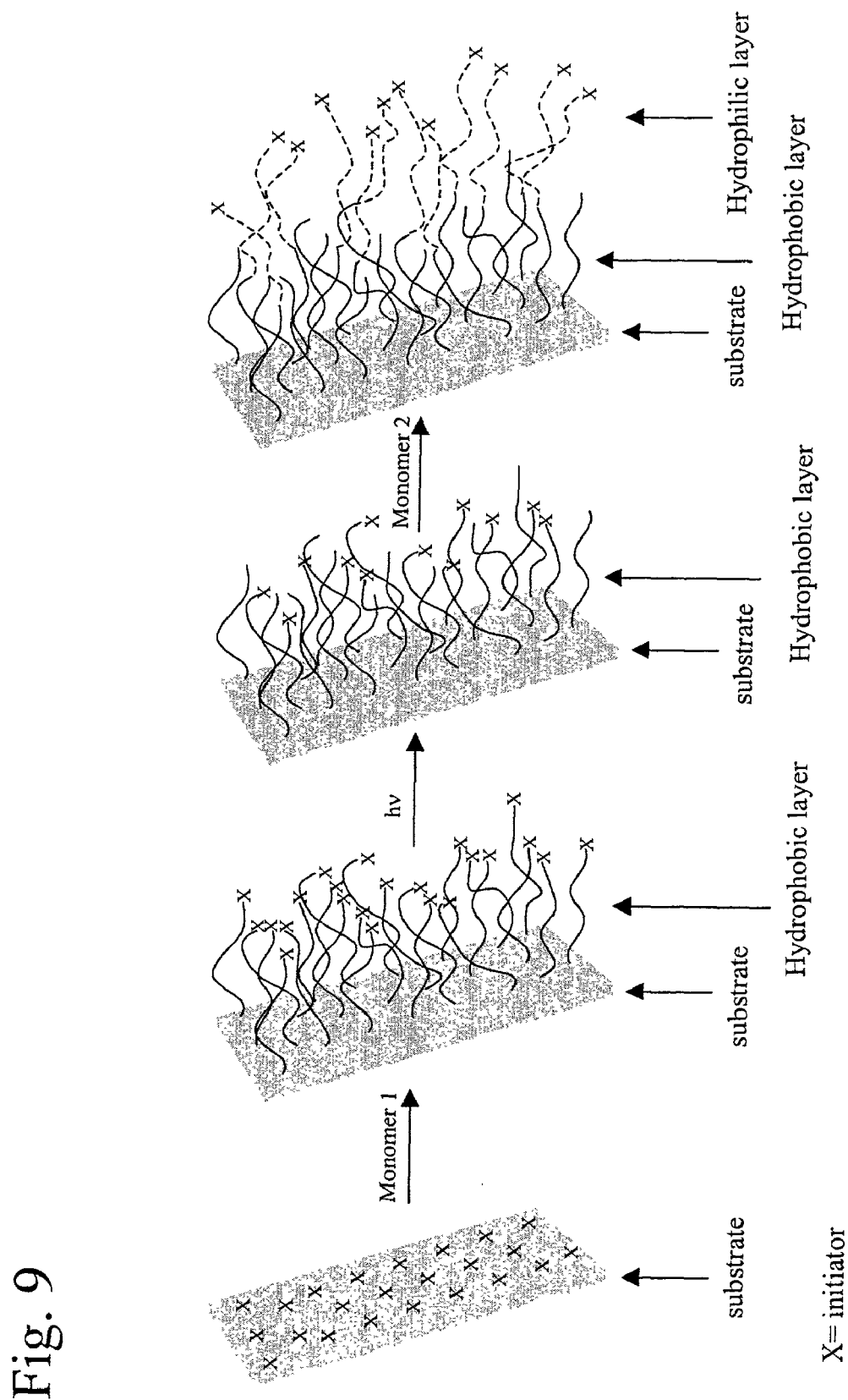

| | | NHSMA/DMA Monomer Ratio | | | | |
|---|---|---|---|---|---|---|
| | | 1% | 3% | 5% | 10% | 25% |
| Chain Density | 2% | | | | | |
| | 5% | | | | | 1042 |
| | 15% | | | 4174 | 2507 | 2064 |
| | 50% | | | 7221 | 3822 | 1961 |
| | 75% | 989 | 5048 | 25209 | | |
| | 100% | 1503 | 2865 | 10258 | | |

Probe Loading (fluorescent count)

| | | \multicolumn{5}{c}{NHSMA/DMA Monomer Ratio} |
| --- | --- | --- | --- | --- | --- | --- |
| | | 1% | 3% | 5% | 10% | 25% |
| Chain Density | 2% | | | | | |
| | 5% | | | | | 894 |
| | 15% | | | 4288 | 1342 | 1138 |
| | 50% | | | 5132 | 2567 | 539 |
| | 75% | 4300 | 9340 | 10992 | | |
| | 100% | 3588 | 9058 | 8514 | | |

Hybridization (fluorescent count)

POLYMER BRUSHES FOR IMMOBILIZING MOLECULES TO A SURFACE OR SUBSTRATE HAVING IMPROVED STABILITY

REFERENCE TO RELATED APPLICATION

This application claims priority from U.S. provisional application, U.S. Ser. No. 60/271,692, filed on Jan. 10, 2001.

BACKGROUND

This invention relates to a polymer brush that features polymer layers on a substrate surface. More specifically, the present invention is directed to a substrate having a first layer composed of a number of hydrophobic polymer chains attached to the substrate surface, and a second layer composed of a number of polymer chains, each of which include a water-soluble or water-dispersible segment having two termini, one terminus being free and the other being bound to a hydrophobic polymer chain. The present invention is particularly well suited for use as a sensor, wherein probes for biological molecules are attached to the water-soluble or water-dispersible segments. Sensors of this type are particularly useful for analyzing aqueous samples that contain biological materials. The present invention is further directed to methods of synthesizing such sensors, including a method wherein (i) an iniferter initiator is attached to the substrate surface in order to initiate polymer growth therefrom, and/or (ii) an activated monomer is used which yields polymer chains having functional groups to which probes can be attached without the need of a separate activation step.

Sensors for analyzing biological samples typically have the ability to process samples accurately and rapidly in an aqueous environment. This, in turn, looks to the presence of multiple probes on a single substrate surface capable of selectively interacting with components of the sample. For example, nucleic acid hybridization assays use multiple oligonucleotide probes bound to the substrate surface at pre-selected sites. The oligonucleotide probes, in turn, are available to participate in a hybridization reaction with selected nucleic acid components of the sample. Generally, this interaction of probe and sample relates to the utility of the components of the biological sample, such as the identity, concentration, purity or form of the components being sensed. There are generally many types of probes known, for example, antibodies that may immunoreact with a desired protein in a diagnostic assay, other protein binding assays, and dyes that change color to indicate the concentration of a desired protein, enzyme, small organic molecule, or inorganic molecule such as calcium or lithium.

Attaching probe molecules to surfaces is typically difficult for a number of reasons. For example, the surfaces often lack functional groups that are uniquely reactive in an aqueous system, or that are readily accessible to the probe molecules (as a result of factors such as surface crowding or steric hindrance). The latter problem becomes particularly acute as the number of functional groups per unit area of surface increases. In addition, once probes are bound to the surface, they must remain accessible to components of the biological sample. Here, too, factors such as steric hindrance may hamper accessibility. Molecular crowding (i.e., density) becomes a critical issue as well, particularly in systems where fluorescence quenching can be an issue. Finally, given that the biological samples to be analyzed (or "probed") are often aqueous, hydrolysis of the bond or linkage which holds the probe to the substrate surface can result in detachment of the probe, thus reducing signal sensativity.

Controlled free radical polymerization methods with living-type kinetics have been used to covalently bond polymers to the surfaces of substrates and thereby form "polymer brushes." Husseman et al., *Macromolecules* 1999, 32, 1424–31, for example, describe a variety of polymer brushes prepared using such methods. The resulting brushes, however, were not water-soluble or water-dispersible and thus were not suitable for applications involving aqueous samples such as biological samples. As a result, the stability of bonds linking the polymers to the substrate surface, when exposed to an aqueous environment, was not addressed. Additionally, Husseman et al. failed to address the importance of controlling the grafting density of, or spacing between, the polymer chains attached to the substrate surface, in order to optimize both the number of probes which may be attached for a given application, as well the efficiency of those probes, once attached, to interact with the target molecules.

Accordingly, a need continues to exist for a polymer brush, as well as a process for the preparation thereof, wherein the polymer chains are stably bound to the substrate surface, such that the polymer chains will not detach when used in an aqueous environment. Such polymer chains will preferably have a controlled molecular architecture (i.e., composition, functionality, molecular weight, polydispersity, etc.), as well as spacing or grafting density, such that the attachment of probe molecules of a given size or type can be optimized. Such brushes would thus enable the preparation of a sensor (i.e., a polymer brush having probe molecules attached thereto) having enhanced stability in an aqueous environment and a controlled structure, such that probe accessibility to the target biological molecules can be optimized.

SUMMARY OF THE INVENTION

Among the several features of the present invention therefore, is the provision of a polymer brush for selectively interacting with biomolecules having improved stability when exposed to an aqueous environment; the provision of such a brush wherein improved stability in aqueous environments is achieved by the presence of hydrophobic polymer chains on the substrate surface of the brush, forming a hydrophobic layer of a controlled thickness; the provision of such a brush wherein polymer chains having a water-soluble or water-dispersible segment having functional groups capable of bonding to a probe are attached to the hydrophobic polymer chains; the provision of such a brush wherein the molecular weight and/or density of the hydrophobic polymer chains is controlled to optimize bond stability to the substrate surface; and, the provision of such a brush wherein the density of the water-soluble or water-dispersible polymer segments is controlled independent of the hydrophobic polymer chain density, and further is controlled to optimize functional group accessibility for probe attachment and/or probe accessibility for the attachment of a molecule of interest.

Further among the features of the present invention is the provision of a polymer brush for selectively interacting with biomolecules wherein water-soluble or water-dispersible polymers, associated with the substrate surface of the brush, contain functional groups which attach probes without the need for chemical activation.

Still further among the features of the present invention is the provision of a sensor for selectively interacting with biomolecules wherein polymer chains bound to the substrate surface of the sensor have water-soluble or water-dispersible segments which contain the residue of a monomer having a probe for binding the biomolecule already attached thereto.

Still further among the features of the present invention is the provision of a polymer brush for selectively interacting with biomolecules wherein a low density of water-soluble or water-dispersible polymer segments are directly or indirectly attached to the substrate surface of the brush, in order to optimize functional group accessibility for the attachment of large diameter probes and/or probe accessibility for the attachment of large diameter molecules.

Still further among the features of the present invention is the provision of process for preparing a polymer brush for selectively interacting with biomolecules, wherein multiple polymer layers are present on the substrate surface of the brush; the provision of such a process wherein living free radical polymerization is employed to grow a first polymer layer from the surface; and, the provision of such a process wherein, prior to growth of a second polymer layer from the first, a portion of the "living" polymer chain ends are deactivated or terminated, such that additional polymer chain growth does not occur, in order to control the polymer chain density of the second layer.

Briefly, therefore, the present invention is directed to a sensor for binding a molecule in an aqueous sample in an assay. The sensor comprises a substrate surface and a layer on the substrate surface comprising polymer chains having two termini and a water-soluble or water-dispersible intermediate segment between the termini. One terminus of the polymer chain is free and the other terminus is bound to the substrate surface. The intermediate portion of the polymer chain containing groups for the attachment of a probe for binding the molecule which are capable of attaching said probe without first being subjected to a chemical treatment to activate said for probe attachment. The sensor further comprises a probe for binding the molecule.

The present invention is additionally directed to a sensor for binding a molecule in an aqueous sample in an assay. The sensor comprises a substrate surface and a layer on the substrate surface comprising polymer chains having two termini and a water-soluble or water-dispersible intermediate segment between the termini. One terminus of the polymer chains is free, and the other terminus is bound to the substrate surface. The intermediate portion of the polymer chains comprise a residue of a monomer having a probe for binding the molecule attached thereto.

The present invention is further directed to a polymer brush for binding a molecule in an aqueous sample in an assay. The brush comprising a substrate surface, a hydrophobic layer comprising hydrophobic polymer chain segments attached to the substrate surface having a dry thickness of at least about 50 angstroms, and a hydrophilic layer attached to the hydrophobic layer containing functional groups for the attachment of a probe for binding the molecule.

The present invention is still further directed to a polymer brush for binding a molecule in an aqueous sample in an assay. The brush comprises a substrate surface, a layer on the substrate surface comprising polymer chains having two termini and a water-soluble or water-dispersible intermediate portion between the termini, one terminus being free and the other terminus being bound to the substrate surface, the intermediate portion containing functionalized groups for the attachment of a probe for binding the molecule, spacer molecules bound to said surface, and a probe attached to the functional sites for binding the molecule. The density of the functionalized groups is at least about 20 picomoles per square centimeter of substrate surface area. The ratio of polymer chains to the sum of polymer chains and spacer molecules ranges from about 0.02:1 to about 0.1:1. The probe has a diameter of at least about 50 angstroms.

The present invention is still further directed to a polymer brush for binding a molecule in an aqueous sample in an assay. The brush comprises a substrate surface having a polymer layer thereon, said polymer layer comprising a first hydrophobic layer attached to the substrate surface, and a second hydrophilic layer attached to the hydrophobic layer containing sites for the attachment of a probe for binding the molecule, said brush being characterized in that, upon being immersed in a 10 mmolar sodium hydroxide solution for about 15 minutes, the polymer layer thickness is reduced by less than about 40%.

The present invention is further directed to methods for preparing the polymer brushes of the present invention. For example, the present invention is further directed to a method of preparing a polymer brush for binding a molecule in an aqueous sample in an assay, wherein the method comprises forming a hydrophobic layer on a substrate surface having a dry thickness of at least about 50 angstroms, and then forming a hydrophilic layer on said hydrophobic layer.

The present invention is still further directed to a method of preparing a polymer brush for binding a molecule in an aqueous sample in an assay. The method comprises (i) bonding a molecule, capable of initiating free radical polymerization having living-type kinetics to a surface of a substrate at one or more points to form a derivatized surface; (ii) contacting said derivatized surface with a composition comprising a hydrophobic monomer under living free radical reaction conditions to form a bound, hydrophobic polymer layer; (iii) treating said hydrophobic polymer layer to render a portion of living free radical polymer chain ends incapable of re-initiating polymerization under free radical polymerization conditions; and, (iv) contact said treated layer with a composition comprising a water-soluble or water-dispersible monomer under free radical reaction conditions to form polymer chains bound at one end to a hydrophobic polymer, said bound polymer chains comprising: (a) a water-soluble or water-dispersible segments having a weight average molecular weight of at least about 1,000; and (b) one or more functional groups on said bound polymer chains that are capable of reacting with a probe selective for the biological molecule The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

FIG. 9 is a schematic drawing illustrating a method of forming a bilayer polymer brush, wherein hydrophobic polymer chain segments are attached to the substrate surface and hydrophilic or water-soluble polymer chain segments are attached to at least a portion of the ends of the hydrophobic segments (the density of the hydrophilic chains being controlled in this illustrating by means of the photobleaching process.)

DETAILED DESCRIPTION OF THE PREFERRED EMBODIMENTS

Figure 1:
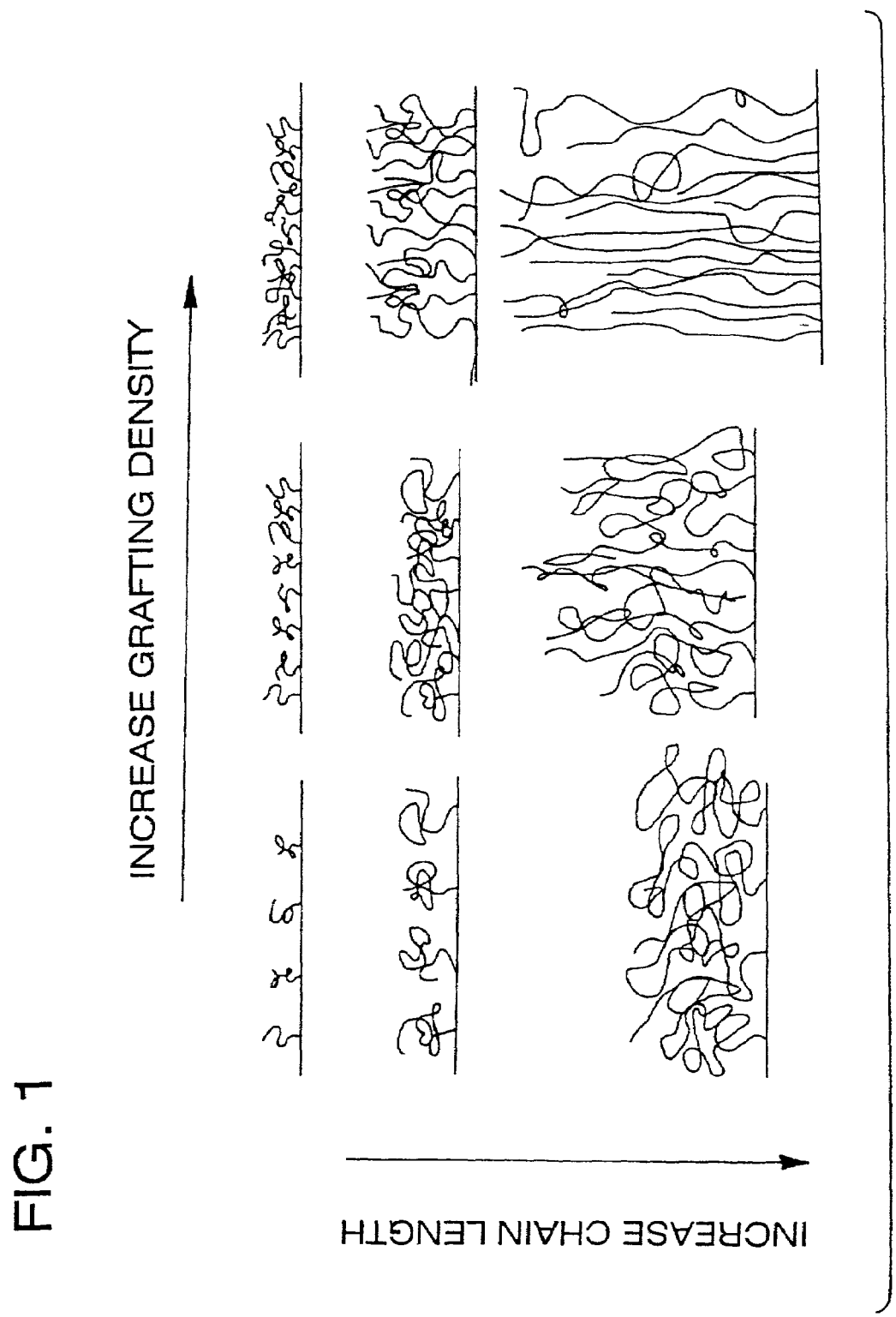
FIG. 1 is a schematic drawing showing the effect of increasing grafting density and increasing polymer chain length on a hypothetical surface to which polymer chains are bound.

As has previously been reported (see, e.g., PCT Application Serial No. PCT/US00/18339, incorporated herein by reference in its entirety), polymer brushes for binding a molecule in an aqueous sample in an assay can be prepared to possess polymer chains, attached to the substrate surface of the brush, of a controlled density having water-soluble or water-dispersible segments which contain functionalized sites that, after being activated (i.e., after being subjected to some linking chemistry), attach probes for binding the molecule of interest. Such brushes can be prepared, for example, by means of a free radical polymerization process having living-type kinetics, wherein an initiator (e.g., a nitroxide) is bound (e.g., covalently bound) to the substrate surface to ensure polymer chain growth from the surface, the chain density being controlled by the ratio of initiator molecules to non-initiating, spacer or "dummy" molecules attached to the substrate surface.

In accordance with certain embodiments of the present invention, it has been discovered that, for applications wherein an aqueous sample is to be analyzed, an improved polymer brush can be prepared by growing polymer chains from the substrate surface wherein at least a portion of the chains comprise a first segment or block which is hydrophobic, in order to form a hydrophobic layer of some minimum thickness on the substrate surface (e.g., about 50 angstroms, 75 angstroms, 100 angstroms or more), a second water-soluble or water-dispersible segment or block then being grown from at least a portion of hydrophobic segment ends. This hydrophobic layer renders the polymer chains more stable to aqueous environments, the layer acting as a barrier to reduce, and possibly prevent, hydrolysis of the covalent bonds linking the chains to the substrate surface. As a result, the polymer brushes of the present invention can be used under more extreme conditions (e.g., higher temperatures, pressures, pH), and can additionally be reused for some applications (the brushes now being able to undergo washing to remove bound molecules and/or probes).

In accordance with other embodiments of the present invention, which may or may not include the above-described multi-layer system, the density of the water-soluble or water-dispersible segments or blocks can advantageously be controlled, at least partially for example, by a process wherein a portion of the "living" hydrophobic segment ends are terminated or rendered inactive to subsequent polymerization. More specifically, such polymer brushes can be prepared to have a controlled density of water-soluble or water-dispersible polymer chain segments, essentially independent of the density of the hydrophobic polymer chain segments, by means of, for example, an iniferter/UV initiation system (which is advantageous because it is relatively inexpensive and enables a broad range of monomers to be used compared to, for example, a nitroxide/heat system). As further described herein, the ability to control polymer chain density is particularly advantageous in view of the various sizes of probes than can be employed.

Furthermore, in accordance with certain embodiments of the present invention, which may or may not include the above-described hydrophobic layer, it has been discovered that a polymer brush can be prepared wherein at least a portion of the water-soluble or water-dispersible polymer segments possess functional groups which do not require a separate activation step prior to probe attachment; that is, after the polymer brush has been prepared, at least a fraction of the polymer chains attached to the substrate surface contain water-soluble or water-dispersible segments comprising functional groups that do not have to be subjected to some linking chemistry before probes can be attached. As described in greater detail below, such segments can be prepared by using monomers having functional groups that are directly reactive with the probe of interest. Alternatively, the need for activation (i.e., linking chemistry) may be obviated by attaching the probe to the monomer prior to the polymerization process; that is, the polymer chains may be formed from monomer which already contains the desired probe, as further described herein.

These and other advantageous features of the present invention are described in greater detail below.

Overview—Polymer Brushes

Water-dispersible/Water-soluble Segments

In accordance with the present invention, a layer is formed on a surface of a substrate which comprises a plurality of polymer chains. Each of these polymer chains has two termini and a water-soluble or water-dispersible intermediate portion between the termini, one terminus being free and the other terminus being bound to the substrate surface in some way. The water-soluble or water-dispersible intermediate portion typically has a weight average molecular weight of at least about 1000 and, depending upon the particular assay, may preferably have a weight average molecular weight of at least about 5,000, 10,000, 50,000, 100,000, 200,000, 300,000, 400,000, 500,000 or even at least about 750,000. (In some alternative embodiments, the molecular weight may range from about 1,000 to about 5 million, from about 25,000 to about 1 million, or from about 50,000 to about 750,000.)

In addition, the intermediate portion contains functionalized sites or groups for the attachment of a probe for binding a molecule, and is typically substantially free of crosslinks to the intermediate portion of other polymer chains. As a result, one terminus of each of the polymer chains is free to extend into an aqueous environment and the other terminus is bound to the substrate surface, either directly (including, for example, where the end of the water-soluble or water-dispersible segment is bound to a portion of the initiator, or linker-initiator, molecule attached to the substrate surface, as further described herein) or indirectly (including, for example, (i) where an intervening, hydrophobic segment or layer of polymer is present between the water-soluble or water-dispersible segment and the substrate surface, or (ii) where a triblock copolymer is formed, the central block being for example hydrophobic and attached or associated with the substrate surface in some way).

In this regard it is to be noted that, as used herein, "terminus" generally refers to end regions of the polymer chain, within which various polymer architectures may be present (e.g., linear chains, branched chains, etc.); that is, it is to be understood that, as used herein, "terminus" does not necessarily refer to the last atom at each end of the principal polymer chain.

It is to be further noted that, as mentioned herein, in order to maximize the "solution-like" character of the probes, it is preferred that these water-soluble or water-dispersible segments be substantially free (i.e., less than about 50%, 25%, 10%, 5%, or even about 1%) of covalent crosslinking, and more preferably substantially free of all types of physical crosslinking as well.

Hydrophobic Polymer Layer—Enhanced Stability

Experience to-date has show that the conditions or environments to which common sensors are subjected typically lead to the detachment of the probes from the substrate surface (e.g., glass), rendering the sensor unacceptable for use. More specifically, as further described herein, experience has shown that silane linkers or linkages, which are most commonly employed to attach probes (e.g., DNA probes) to a substrate surface, are susceptible to hydrolysis when subjected to conditions commonly employed in gene expression tests (e.g., heating to about 40 to 60° C. for about 16 hours). In fact, it is not uncommon for up to about 90% or more of the probes to be lost as a result of links being broken during such tests.

In addition to the common test conditions to which sensors are subjected, it is also desirable at times to be able to de-hybridize the probe/molecule duplex after the assay is complete, in order to remove the molecule from the probe while keeping the probe bound to the polymer segment, so that the sensor can be reused. A common practice for de-hybridization is to submerge the sensor in boiling water at a neutral pH, or if more extreme conditions are needed in a basic solution (e.g., a sodium hydroxide solution, pH ranging from about II to about 13), for several minutes (e.g., about 5, 10, 15 minutes or longer). However, most sensors currently available commercially would not be able to withstand such conditions; that is, after being subjected to such conditions, for most sensors, substantially all of the probes would not remain attached to the substrate surface. As a result, any attempt to "clean" the sensors would essentially render them useless. Because most sensors cannot be reused, the overall cost of such methods of analysis is significantly increased.

As reported in PCT Application Serial No. PCT/US00/18339, probe retention can be significantly increased by attaching the probes to a water-soluble or water-dispersible polymer chain segment which is then bound to the substrate surface. Although these polymer chains are typically bound to the substrate surface by covalent bonds, which are also susceptible to hydrolysis, the number of probes lost when subjected to hydrolyzing conditions is significantly reduced (e.g., less than 20%). In accordance with the present invention, it has now been discovered that the stability of the bonds which link the polymer chains to the substrate surface, when exposed to hydrolyzing conditions (such as the exemplary gene expression conditions, or alternatively the basic sodium hydroxide solution, described above), can be increased by forming a hydrophobic layer of some minimum thickness on the substrate surface, the layer comprising hydrophobic polymer chain segments having one end attached to the substrate surface (and a fraction of the hydrophobic chain segments having the other end attached to a water-soluble or water-dispersible polymer segment, as further described herein). This hydrophobic layer thus acts as a "barrier" which limits, and preferably prevents, the access of hydrolyzing reactants to the covalent bonds. As a result, the degree of polymer chain detachment can be limited such that, upon being exposed for example to a sodium hydroxide solution (e.g., about 5, 10, 15, 20 mmol) for about 10, 15, 20 or even 30 minutes, the overall thickness of the polymer layer (i.e., the thickness of the hydrophobic layer plus the thickness of the water-soluble or water-dispersible layer) is reduced by less than about 40%, 30%, 20%, 10% or even 5%, thus limiting the degree of probe loss.

While the thickness of the layer may vary from one application to another, typically the average dry thickness will be at least about 50 angstroms, 100 angstroms, 250 angstroms, 500 angstroms, 750 angstroms, 1000 angstroms or more (e.g., about 1250, 1500, 1750, 2000 angstroms or more). In some preferred embodiments, the average dry thickness will range from about 50 to about 2000 angstroms, from about 100 to about 1500 angstroms, from about 250 to about 1250 angstroms, or even from about 500 to about 1000 angstroms.

It is to be noted in this regard, however, that layer thickness is at least in part a function of the density of the hydrophobic polymer segments as well as the molecular weight (in at least some applications, a higher molecular weight resulting in a lower density being necessary to achieve the desired degree of hydrophobicity, or protection from hydrolysis, and vice versa). Accordingly, typically the segment density and molecular weight will be controlled to achieve the desired layer thickness. Segment density can be controlled as further described herein (e.g., by controlling the ratio of initiator to spacer or "dummy" molecules on the substrate surface prior to initiating the polymerization process, or by terminating living ends of the hydrophobic polymer chains prior to initiating growth of a hydrophilic or water-soluble polymer chain segment), while molecular weight is controlled by means common in the art. Generally speaking, the ratio of the hydrophobic polymer segments to the sum of the hydrophobic polymer segments and spacer or dummy molecules attached to the substrate surface will range from about 0.1 to about 1, from about 0.2 to about 0.8, or even from about 0.4 to about 0.6, in some preferred embodiments this ratio having a value of about 1, about 0.8 or even about 0.6.

It is to be further noted that the hydrophobic polymer segment can optionally be crosslinked; that is, in some embodiments, crosslinks between the hydrophobic polymer segments can be present. Additionally, the hydrophobic segment or block can be linear or non-linear (e.g., branched, star, etc.). When present, crosslinking and/or branching may serve to enhance the degree of protection imparted by the hydrophobic layer. As a result, in some cases the presence of crosslinks and/or branching may enable the thickness of the hydrophobic layer to be reduced.

The hydrophobic layer comprises hydrophobic polymer chain segments or blocks, each having one end attached to the substrate surface (by means generally described herein), each segment in turn comprising repeat units derived from one or more hydrophobic monomers; that is, each segment may comprise repeats unit derived from a single hydrophobic monomer (i.e., a homopolymer) or of different hydrophobic monomers (i.e., a copolymer).

Generally speaking, essentially any monomer which will impart hydrophobicity to the segment or block can be used. Quantitatively, the hydrophobic/hydrophilic nature of the monomers may be determined according to the log P of the particular monomers, which is sometimes referred to as the octanol-water partition coefficient. Log P values are well known and are determined according to a standard test that determines the concentration of monomer in a water/1-octanol separated mixture. In particular, computer programs are commercially available, as well as on various internet sites, that will estimate the log P values for particular monomers. For example, some of the log P values in this application were estimated using a program available from an internet website (esc.syrres.com), which provides an estimated log P value for molecules by simply inserting the CAS registry number or a chemical notation. Hydrophobic monomers typically will have a log P value above zero and hydrophilic monomers typically will have a log P value close to or below zero. Accordingly, typically monomers employed in preparing the hydrophobic segments which make up the hydrophobic layer will have a log P value of greater than about 0.5, and preferably will have a log value of greater than about 1 (e.g., greater than about 1.5, 2, 2.5 or even 3).

For example, the following hydrophobic monomers have the following log P values: styrene, about 2.95; n-butylacrylate, about 2.36; and tert-butylacrylate, about 2.09. Other suitable hydrophobic monomers include, but are not limited to, acrylic or methacrylic acid esters of $C_1$–$C_{18}$ alcohols (such as methanol, ethanol, methoxy ethanol, 1-propanol, 2-propanol, 1-butanol, 2-methyl-1-propanol, 1-pentanol, 2-pentanol, 3-pentanol, 2-methyl-1-butanol, 1-methyl-1-butanol, 3-methyl-1-butanol, 1-methyl-1-pentanol, 2-methyl-1-pentanol, 3-methyl-1-pentanol, t-butanol (2-methyl-2-propanol), cyclohexanol, neodecanol, 2-ethyl-1-butanol, 3-heptanol, benzyl alcohol, 2-octanol, 6-methyl-1-heptanol, 2-ethyl-1-hexanol, 3,5-dimethyl-1-hexanol, 3,5,5-trimethyl-1-hexanol, 1-decanol, 1-dodecanol, 1-hexadecanol, 1-octadecanol, and the like, the alcohols having from about 1 to about 18 carbon atoms, preferably from about 1 to about 12 carbon atoms); styrene; polystyrene macromer, vinyl acetate; vinyl chloride; vinylidene chloride; vinyl propionate; alpha-methylstyrene; t-butylstyrene; butadiene; cyclohexadiene; ethylene; propylene; vinyl toluene; and mixtures thereof. Preferred hydrophobic monomers (with approximate log P values listed in parentheses) for some embodiments of the present invention include n-butyl methacrylate (2.36), isobutyl methacrylate (2.66), t-butyl acrylate (2.09), t-butyl methacrylate (2.54), 2-ethylhexyl methacrylate (4.09), methyl methacrylate (1.38), vinyl acetate (0.73), t-butyl acrylamide (1.02) and mixtures thereof. (For additionally log P values and information, see, e.g., log P listings from Hansch et al., *Exploring QSAR: Hydrophobic, Electronic, and Steric Constants* (ACS Professional Reference Book, 1995), which is incorporated herein by reference.)

Once the hydrophobic layer has been formed on the substrate surface, a second, hydrophilic layer may be formed on the hydrophobic layer (by means described further herein below); that is, after a hydrophobic polymer layer, comprising hydrophobic polymer chain segments or blocks wherein one end of the segment or block is attached to the substrate surface, has been formed, a second layer comprising polymer blocks having a water-soluble or water-dispersible segment can be formed by attaching one end of the block to a "free" end of a hydrophobic polymer block. Various methods for the formation of block copolymers are further described herein below. However, generally speaking, block copolymers can be formed by, for example, linking two pre-existing chains, or by in-situ polymerization (e.g., growing one block and then another, such as by free radical polymerization, preferably free radical polymerization having living-type kinetics, and still more preferably by means of an iniferter initiated process).

In one preferred embodiment, a polymer brush of the present invention is formed using free radical polymerization techniques, and more preferably living free radical polymerization techniques, wherein a block copolymer is formed by growing a first hydrophobic polymer block from the substrate surface, followed by the growth of a second water-soluble or water-dispersible block from at least a portion (e.g., 10%, 20%, 40%, 60%, 80%, 90% or more) of the "living" hydrophobic block ends. In such instances, the ratio of water-soluble or water-dispersible segments to hydrophobic segments is less than 1:1 (e.g., less than about 0.8:1, 0.6:1, 0.4:1, 0.2:1, 0.1:1, 0.05:1, or even 0.01:1). Additionally, also in such instances, the ratio of water-soluble or water-dispersible segments to the number of attachments points on the substrate surface is less than about 1:1 (e.g., less than about 0.8:1, 0.6:1, 0.4:1, 0.2:1, 0.1:1, 0.05:1, or even 0.01:1).

Generally speaking, essentially any monomer which will impart hydrophilicity to the polymer segments of this second layer can be used. As noted above, quantitatively, the hydrophobic/hydrophilic nature of the monomers may be determined according to the log P of the particular monomers. Hydrophilic monomers typically have a log P close to or below zero. Accordingly, monomers employed in preparing the hydrophilic segments which make up the hydrophobic layer will typically have a log P value of less than about 1 or 0.5, and preferably will have a log P value of about 0.3, 0.1 or less (e.g., less than about −0.1, −0.3, −0.5 or less).

For example, the following hydrophilic monomers have the following log P values: acrylic acid, about 0.35; 2-methoxyethylacrylate, about 0.45; and 2-hydroxyethyl-methacrylate, about 0.47. Other hydrophilic monomers and their log P values include, but are not limited to, acrylamide (about −0.67), 2-hydroxyethylacrylate (about −0.21), acrylic acid (0.35), methacrylic acid (0.93), N,N-dimethylacrylamide (−0.13), dimethyl aminoethyl methacrylate (0.97), quaternized dimethylaminoethyl methacrylate, methacrylamide (−0.26), maleic acid (−0.48), maleic anhydride and its half esters, crotonic acid (0.72), itaconic acid (−0.34), acrylamide (−0.67), acrylate alcohols, hydroxyethyl methacrylate, diallyldimethyl ammonium chloride, vinyl ethers (such as methyl vinyl ether), maleimides, vinyl pyridine, vinylimidazole (0.96), other polar vinyl heterocycles, styrene sulfonate, allyl alcohol (0.17), vinyl alcohol (such as that produced by the hydrolysis of vinyl acetate after polymerization), salts of any acid or amine listed above, as well as mixtures thereof. Preferred hydrophilic monomers for some embodiments of the present invention are further described herein below. (For additionally log P values and information, see, e.g., log P listings from Hansch et al., *Exploring QSAR: Hydrophobic, Electronic, and Steric Constants* (ACS Professional Reference Book, 1995), which is incorporated herein by reference.)

It is to be noted in this regard that, in some embodiments, it is also preferable for there to be some minimum absolute difference in the log P values for the hydrophobic and hydrophilic monomers used in preparing the hydrophobic and water-soluble or water-dispersible polymer segments, respectively. More specifically, in some embodiments it is preferred that the absolute difference between the log P values of the hydrophobic and hydrophilic monomers employed in preparing the polymer brushes of the present invention be at least about 0.5, 0.75, 1, 1.25, 1.5, 1.75, 2 or even 2.5.

It is to be further noted that, like the hydrophobic layer, the density and molecular weight of the water-soluble or water-dispersible segments can be controlled to achieve the desire degree of functional group and/or probe accessibility (as further described herein); that is, the density and molecular weight can be controlled to ensure the desired number of functional groups are present for probe attachment, and that spacing between these segments is optimized to ensure accessibility of the probe to the functional groups as well as accessibility of the probes to the molecules to which the probes are ultimately to be attached. The density of this second layer can be determined, for example, by measuring the increase in thickness of the second block and comparing it to the thickness of the same layer grown from a substrate of known density, expressed for example as initiator to spacer to dummy ratio (the hydrophilic layer having a dry thickness, for example, which ranges from about 10 to about 2000 angstroms, from about 15 to about 1000 angstroms, or from about 25 to about 100 angstroms).

It is to be still further noted that while the present invention is particularly well suited for use with glass or fused silica surfaces, as further described herein, this approach can also be employed with other surfaces that are notoriously sensitive to corrosive media, such as for example nylon membranes.

Polymer Chain Attachment—Grafting "from" vs. "on to"

In view of the foregoing, generally speaking the polymer brushes of the present invention may be prepared by one of two general approaches: (i) the "grafting from" approach, whereby the polymer chain is grown from the substrate surface; and, (ii) the "grafting on to" approach, whereby a preformed polymer chain is linked on to the substrate surface. The "grafting from" approach includes the attachment of an initiating moiety onto a substrate capable of starting the polymerization of monomers. Possible polymerization techniques include radical, cationic, anionic, and metathesis, as well as insertion-type chain growth mechanisms. In one embodiment, the radical polymerization process is preferred due to its robustness towards aqueous environments and the large range of functional monomers available for this type of polymerization.

Radical polymerizations can be implemented in a number of different ways known in the art, each having as a common feature that a radical forming species is linked to the substrate surface through the functional sites available on the surface. Standard radical initiators include, for example, azo and peroxide initiators, as well as redox systems which lead to uncontrolled polymerizations.

Uncontrolled free radical polymerizations usually produce broader molecular weight distributions, and moreover the number of chain keeps growing as the reaction proceeds, as opposed to controlled polymerization where ideally all the chains are formed at the beginning of the reaction. To a first approximation, the number of grafted chains is equal to the sum of the initiation events, which depend upon the half-life of the bound initiators and the initiator efficiency. "Initiator efficiency" refers to the fraction of the radicals which, once formed, actually generate a new chain. When implementing uncontrolled free radical polymerization, reaction conditions are typically chosen in order to control the chain density and the molecular weight. For example, in one embodiment, uncontrolled polymerization is carried out so as to decompose all the bound initators (achieved by selecting the proper combination of reaction time and temperature). More specifically, if $t_{1/2}$ is the half-life of the bound initators at a given temperature, then the reaction time is preferably $5*t_{1/2}$. The chain density is then the density of initiators bound on the surface, weighted by the initiator efficiency.

For uncontrolled free radical polymerization, it is difficult to control the chain length because the radical concentration is not uniform in the polymerization mixture. Here, the non-covalently attached radicals on the surface can diffuse away from the substrate and, as a result, the local radical concentration will be extremely low, leading to uncontrollably high molecular weights. One way to address both the control of chain density as well as the control of molecular weight is to implement living free radical polymerization (LFRP) techniques. In the case of LFRP, the control of molecular weight is enabled through a control agent which reversibly deactivates the propagating radical. Living free radical polymerization techniques include, for example, nitroxide mediated polymerization, degenerative transfer (such as reversible addition/fragmentation transfer), atom transfer radical polymerization, among other techniques known to people skilled in the art. In one specific case, the initiator and the control agent are combined in one molecule, which is referred to as an initiator-control agent adduct. To gain control of molecular weight, it is necessary to control the radical concentration at the vicinity of the surface. One way to address this issue is to add both extra initiators and/or adducts, as well as control agents into the polymerization mixture.

Various combinations of initiating moieties, control agents and adducts, as well as the manner by which they are employed (e.g., in solution, bound to the surface, or both), may be used in the preparation of the polymer brushes of the present invention including, for example:

| Approach | Surface | Solution |
|---|---|---|
| 1 | Initiator | — |
| 2 | Initiator | initiator |
| 3 | Initiator | control agent |
| 4 | Adduct | adduct |
| 5 | Adduct | control agent |
| 6 | Adduct | — |

In one embodiment, an initiator-control agent adduct is attached to the surface via the initiator moiety and non-surface bound adduct is added to the polymerization mixture. This approach leads to the formation of both polymer bound to the substrate surface as well as polymers in solution (which enable valuable information to be learned about the resulting surface because the molecular weight, monomer incorporation and molecular weight distribution are believed to be identical for both polymers). This technique leads to excellent molecular weight control, narrow polydispersities and allows one to monitor the polymer brush growth by measuring the properties of the solution grown polymer.

In another embodiment, the adduct is also attached to the substrate surface, but here only the control agent (instead of the adduct) is added to the polymerization mixture.

In yet another embodiment, no adduct is used but the control agent is added at a concentration similar to the steady-state concentration achieved in the above embodiment wherein adduct is both bound to the substrate surface and present in solution. Hence, the radicals that are found stem mostly from the bound initiator/bound initiator-control agent adduct. The control over molecular weight is ensured by the stable free radical purposely added in the polymerization reaction. As the polymerization proceeds mainly from the surface, virtually no polymer is formed in the solution. Polymer growth is monitored by measuring the polymer layer thickness (e.g. by ellipsometry). Since no polymer is formed in solution, this approach has the advantages of providing (i) a lower viscosity reaction mixture, which facilitates the recovery of monomer and isolation of the modified substrate, and (ii) a lower cost of manufacturing, since no solution adduct is used.

The "grafting on to" approach provides for the preparation of the present polymer brushes from pre-formed polymer chains having water-soluble or water-dispersible segments, the polymer chains having functional groups that react with the substrate surface. A variety of chain-coupling techniques are useful to attach the pre-formed polymer chains to the substrate surface, either by covalent bonding or physical interaction. Covalent coupling is, for example, achieved by chemical reaction between electrophilic entities (such as, for example, acyl halides, isocyanates, sulfonyl halides, activated esters and the like) and nucleophilic entities (such as, for example, hydroxyl, amine, thiol and the like), the nucleophilic or electrophilic groups being present either on the water-soluble or water-dispersible segment or the substrate surface. Many other techniques known by those skilled in the art, which result in bond formation between carbon atoms, heteroatoms, metals and combination thereof are also applicable.

The immobilization of blocks copolymers or graft copolymers is also an efficient way to prepare polymer brushes, whereby these block/graft copolymers comprise (i) water-soluble or water-dispersible segments at their termini (as defined herein), or as pendant entities, and (ii) one or more other segments which exhibit some affinity towards the substrate surface. Such segmented macromolecules can be anchored through, for example, hydrophobic interaction, hydrogen bonding or coulombian interaction. Segmented polymers can be chosen among the following examples: polystyrene-b-polyethyleneoxide, polyethyleneoxide-b-polypropyleneoxide-b-polyethyleneoxide, polymethylmethacrylate-b-polyethyleneoxide, polystyrene-b-poly(meth)acrylic acid, polystyrene-b-polyvinylpyridine, polydimethysiloxane-b-polyethyleneoxide, polydimethylaminoethylmethacrylate-b-polymethacrylic acid and the like.

According to another method, polymer brushes can also be built from polymer particles stabilized by hydrophilic polymers that are deposited on the surface and allowed to fuse in a coherent film by the action of drying.

The grafting process occurs gradually over time periods of hours to days, and the grafted layer is built up continuously. The rate of grafting also increases with the concentration of dissolved polymer. Generally, a limiting value of the brush thickness is approached at long times, but by stopping the grafting process at an earlier selected time it is possible to control the ultimate grafting density, so long as this is less than the ultimate limiting value. While this makes it more difficult to access very high grafting densities, because the grafting process is self-limiting, as discussed herein high grafting densities are typically undesirable, as they lead to reduced accessibility of the binding sites.

It will be understood by those of skill in the art that "grafting" is used in multiple ways in this specification, and that "grafting density" does not require use of the "grafting onto" approach to surface preparation.

Derivatized Surface—Surface-bound Initiators and Spacer or "Dummy" Molecules

The above-noted polymer segments may be bound to the surface through covalent bonding or non-covalent bonding (such as, for example, electrostatic, hydrophobic or affinity binding interactions). In other embodiments, there may be a functional group attached to the polymer segment that is designed to interact with the surface to bind the segment to the surface. For example, the polymer segment may include an —SH group that will interact with certain surfaces, such as gold, to bind it to the surface; other embodiments include Langmuir-Blodgett films, lipid monolayers and lipid bilayers, for the attachment of the polymers.

However, in one embodiment, the polymer segments are attached to the surface functionalities by means of a surface bound initiator which is suitable for free radical polymerization; that is, the polymer segment is attached as a result of, for example, the reaction of monomer with an initiator (such as one suitable for free radical polymerization) that has first been attached to the surface functionalities.

The initiator for the free radical polymerization of the polymer attached to the surface may be any known initiator for water-soluble or water-dispersible monomers. Known initiators include peroxides and the like. In other embodiments, however, a free radical control method is employed, such as a reversible chain transfer process, atom transfer radical polymerization or stable free radical controlled polymerizations. In the specific case of the use of nitroxide control agents, the nitroxide may serve as a control agent or as a chain transfer agent to control molecular weight.

Figure 2:
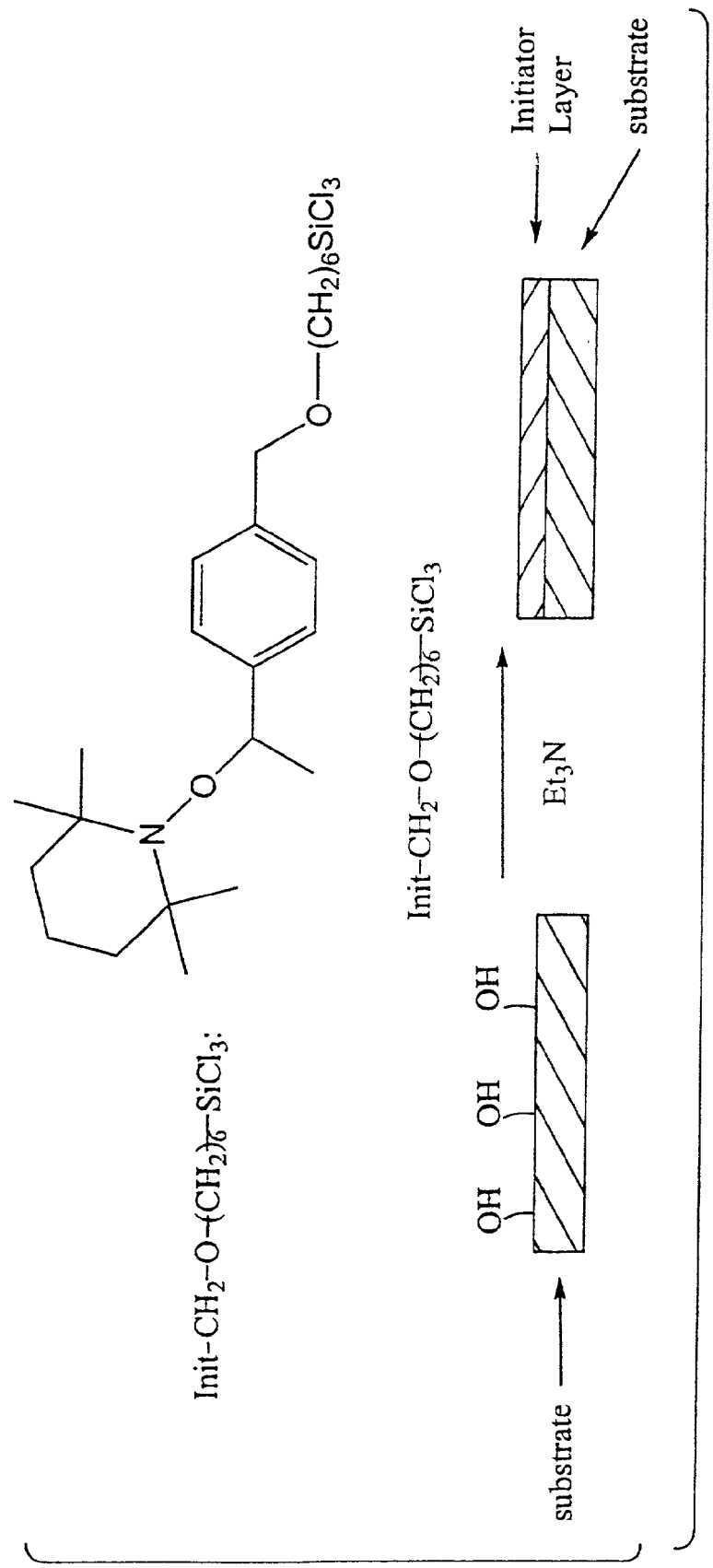
FIGS. 2–5 are schematic drawings showing a method for forming surface-bound polymers having water-soluble or water-dispersible segments bearing functional groups available for bonding to various probe molecules.

When a surface bound initiator is employed, in one preferred embodiment the initiator is covalently bound to the surface of the substrate and is capable of initiating a free radical polymerization reaction with living-type kinetics. A surface-bound initiator may be characterized by the general formula:

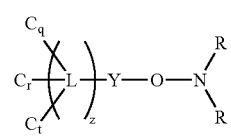

wherein: C is a functional moiety on the surface of the substrate; L is a linker group capable of bonding to at least one C moiety; q, r, and t, independently, are 0 or 1; z is 0, and in some embodiments is preferably 1; O is oxygen, N is nitrogen; and, R is a substituent, as further described herein. The remainder of the structure (i.e., —Y—O—NR$_2$) is referred to as an initiator-control agent adduct, described in greater detail below. When bound to the surface, at least one of q, r or t must be 1. The C moiety is a portion of the surface functionality and is typically oxygen because, as shown in FIG. 2, hydroxyl groups are typically found on the surface of commonly used substrates such as silicon wafers and glass. However, it is possible to bond the initiator to other surface moieties as well. The above formula show the initiator-control agent adduct attached to the substrate surface. For addition to the surface, the starting molecule takes the form $(L)_z$-Y—O—$NR_2$, with the same definitions for L, Y, R and z.

The linker group, L, is optional; that is, the initiator may be directly bound to the substrate surface. However, in some embodiments a linker may be preferred because it helps space the polymer chains away from the substrate surface, which may enhance the accessibility of functional groups on the polymer chains. The length and identity of the linker group is selected depending on the type of surface to which the initiator will be bound and the identity of the particular initiator. In addition, the linker group moieties preferably do not substantially interfere with the polymerization reaction.

As generally indicated above, linkers have an end-group capable of binding to the surface of the substrate, and may be selected from the group consisting of substituted alkyl, heteroalkyl and polyethylene glycol. When substituted alkyls are used, it is preferred that one end of the alkyl chain is substituted with a silyl group.

Figure 3:
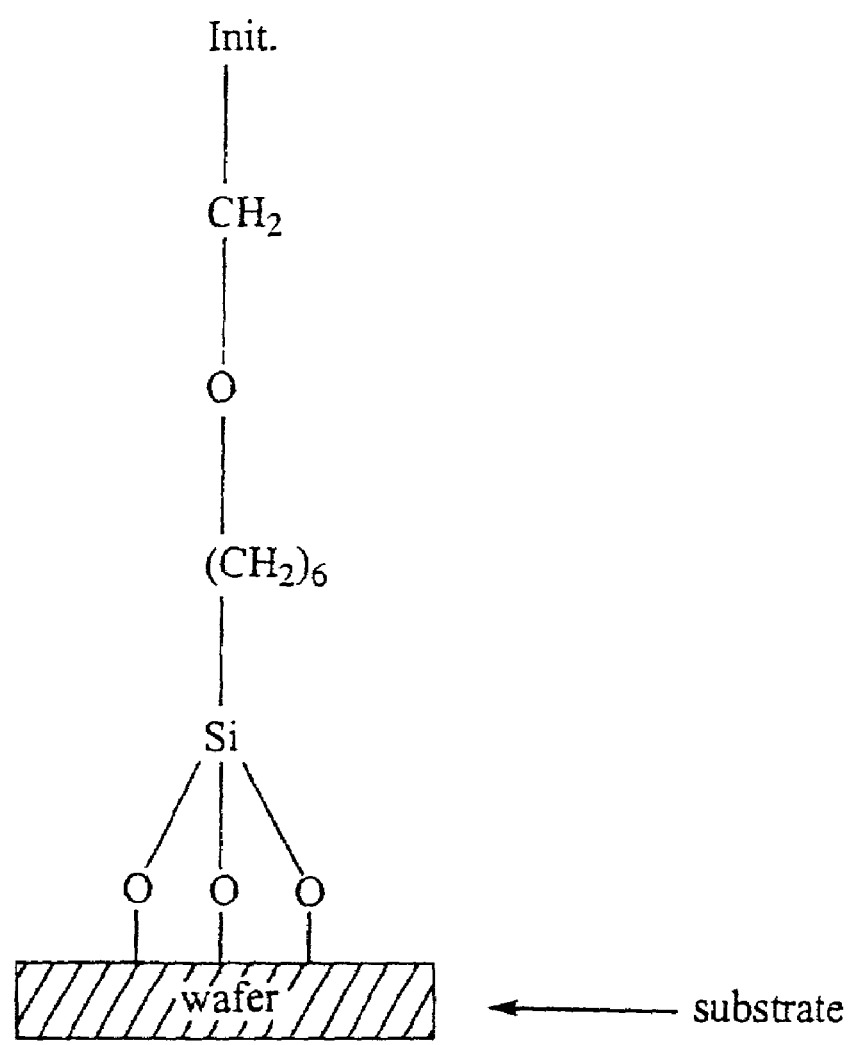
Figure 4:
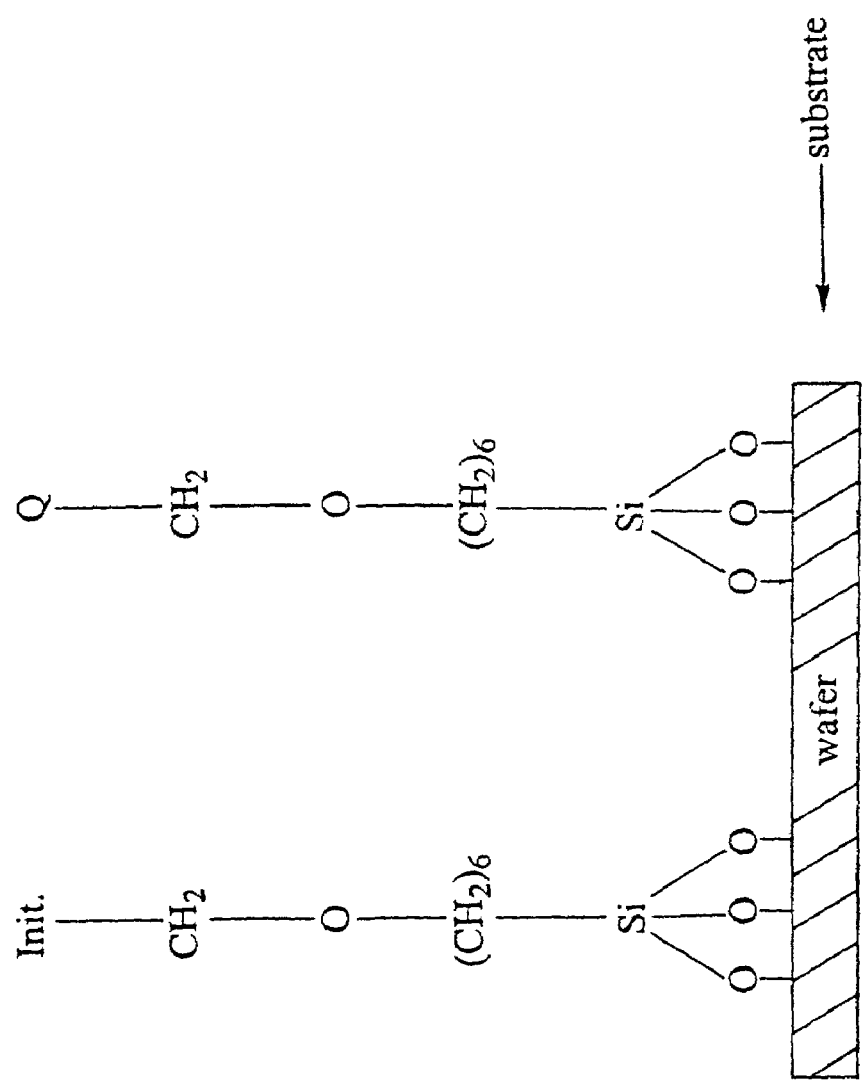

In one preferred embodiment, wherein Si or a $SiO_2$ based surface are used (e.g., such as silicon, silica, fused silica glass, quartz or other silicon based glasses), it is especially desirable for the linker group to include a silicon atom, as shown in FIGS. 2–4, because silicon bonds readily to such surface hydroxyl groups. Additional spacing may be provided by an alkyl or alkoxy group separating the silicon atoms from the initiator-control agent adduct. Linear alkyl and alkoxy groups are preferred because they do not interfere with the subsequent free radical polymerization.

To maximize the stability of the bond between the surface hydroxyl groups and the silicon atom, it is desirable to include at least three atoms, and preferably up to about eight atoms, in the group separating the silicon atom from the initiator-control agent adduct. (As further described herein, in some embodiments stability is enhanced by the presence of a hydrophobic layer being formed on the substrate surface.)

As shown in FIGS. 3 and 4, in some embodiments the initiator is bonded to the substrate surface through the linker atom through at least one attachment site, but preferably to two or (as shown in the figures) three sites of attachment. As further described herein (see, e.g., "Stability Test"), bonding to multiple surface moieties advantageously increases stability by ensuring that the initiator will remain tethered to the substrate even if one or more bonds between the linker atom and the surface moieties were to break. Although covalent bonding of the polymer to the surface (e.g., via the linker, L and initiator fragment, Y) is the preferred in some embodiment, in other embodiments, the polymer is associated with the surface through bonding other than covalent bonding. Alternative non-covalent binding techniques can be selected from among ion pair association, hydrophobic interaction, metallic complexes, multiple H-bonding systems and other host-guest interactions.

In order to control, adjust or optimize the accessibility of functional groups on water-soluble (or water-dispersible) segments of the surface-bound polymer chains to probe molecules, in some embodiments it is important to control the surface grafting density of these segments. As described in more detail elsewhere herein, the desired grafting density, or spacing between these segments, is at least in part a function of the size of the probes to be attached to the functional groups, the grafting density decreasing as the probe size increases in order to prevent, for example, steric hinderance from impeding probe attachment. Density may be controlled in a number of different ways, as further described herein, including the use of of "dummy" or "spacer" molecules bound to the surface, as illustrated in FIG. 4, or alternatively by "terminating" or "quenching" living chain ends prior to growth of the polymer chain segment to which the probes will ultimately be attached, as illustrated for example in FIG. 9.

Density Control—General Considerations Concerning Functional Group Accessibility The nature of the problem associated with functional group accessibility is generally illustrated in FIG. 1, which depicts a hypothetical surface to which a number of polymer chains are bound. As further described in greater elsewhere herein, without being held to a particular theory, it is generally believed that, for polymers of a given composition and chain length, as the average chain grafting density (i.e., the average number of bound chains per unit area) increases, the number of accessible functional groups (i.e., the number of functional groups on the polymer chains which are capable of attaching to a molecule of a given size) increases. However, as the grafting density continues to increase, eventually chains are close enough to become entangled and otherwise sterically hinder the functional group-bearing sites, thereby limiting the ability to attach a probe molecule to the polymer chain at these sites; that is, as the grafting density continues to increase, eventually a point may be reached where the number of accessible functional groups begins to decrease due to increased steric hinderance, a reduction of total free volume, a reduction of the mesh size, and a hindered diffusion of the biomolecules, even though the total number of functional groups continues to increase. If the grafting density increases further, the polymer chains can become so tightly packed or so entangled that essentially the only functional groups accessible to a probe are located at or near to the chain ends (e.g., near the surface below which the grafting density essentially approaches zero).

Figure 6:
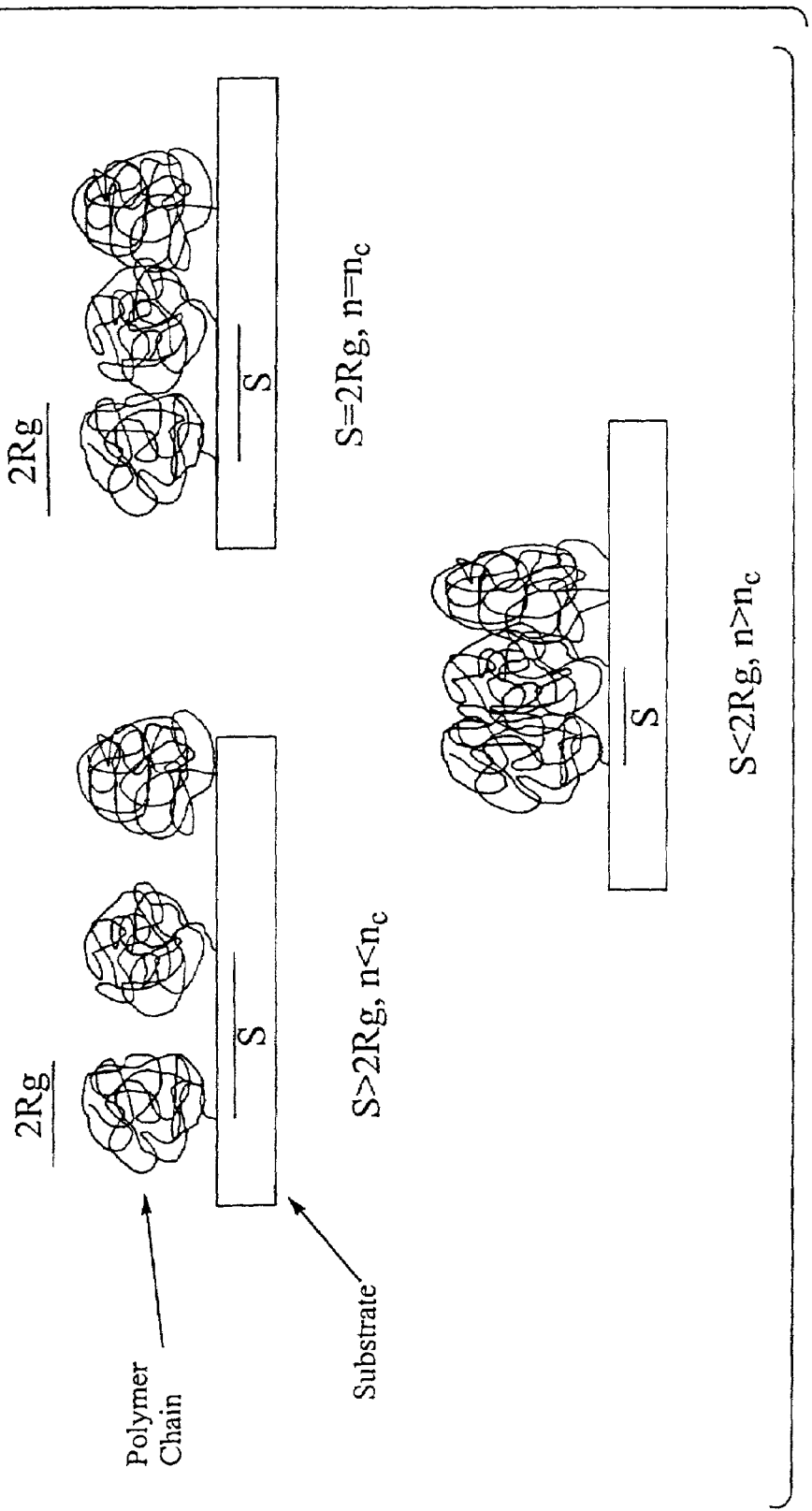
FIG. 6 is a schematic drawing between chain spacing, S, radius of gyration, Rg, and chain grafting density, n, and a critical chain grafting density, $n_c$, at which chain entanglements begin.

A similar phenomenon is believed to occur as chain length increases for a given grafting density. If the segments are short enough so that the average coil diameter is significantly less than the average distance between attachment points, then there is no overlap between the segments. As the segments are made longer, the size of the coils which they form increases until they overlap. With further increase in the chain length, the chains begin to stretch away from the substrate. Once the chains are stretched, further increase in the chain length at a fixed grafting density leads primarily to an increase in the "wet thickness" of the brush, but does not lead to significant further increases in the average polymer concentration within the brush or a reduction of the mesh size. (Mesh sizes may be determined, for example, by means analogous to those described in U.S. Pat. No. 5,126,021.) Accessibility issues are also graphically displayed in FIG. 6, where it is shown that there exists a critical chain density, $n_c$, which is the point at which surface bound polymer chains begin to entangle. As described elsewhere herein, this density may be controlled to control the accessibility of the functional groups on the polymer as desired for a particular embodiment.

In some embodiments, the present invention addresses the problem of functional group accessibility by disclosing how to control various aspects of the preparation methods, including for example the density of available functional moieties on the surface (controlled, for example, by various surface treatments, as described herein and in the literature), the chain lengths (e.g., molecular weight), chain grafting density, and the type and/or number of functional group-containing monomers, thus enabling those of skill in the art to design a sensor with a desired number of available or accessible functional groups present. Stated another way, the present invention discloses how to control the manner by which surface-bound polymers having water-soluble or water-dispersible segments are prepared to enable functional group accessibility to be adjusted which, in turn, enables the polymer-modified surface to be tailored for a given application. As a result, subsequent probe attachment and probe availability for sample screening can be optimized.

In this way, the present invention provides the ability to control the number of functional groups that are available for binding probes of a biosensor, and ultimately thereby to control or tune the sensitivity and other properties of the biosensor. More specifically, depending on the volume occupied by the probe molecules in a particular solution (e.g., aqueous), the grafting density of the polymer chains can be "tuned" to accommodate such probe molecules to avoid surface crowding and optimized accessibility of the probe molecules to the bio-process. It is believed that increased numbers of functional groups, along with minimizing surface effects as discussed elsewhere herein, advantageously provides improved sensitivity of the probe in a bio-process, along with increasing signal, increasing signal to noise ratios and increasing dynamic range (i.e., increasing ability to detect decreasing numbers of target molecules in the sample, as further described herein).

Referring to FIGS. 2–5, in one embodiment, a radical initiator is bound to the surface of a substrate to form a derivatized substrate surface (e.g., FIGS. 2, 3 and 4), as further described herein, which is subsequently contacted with one or more monomers to form surface-bound polymer chains (e.g., FIG. 5) which extend from the substrate surface generally in a direction normal to the substrate surface. In one embodiment, the polymer chains are not substantially crosslinked to other strands, covalently or otherwise, thus permitting a range of movement substantially independent of other polymer chains. According to one approach (and as further described herein), it can be assumed that substantially all functionalities originally on the surface are bound to either an initiator or initiator-control agent adduct or, in some embodiments, a dummy molecule (i.e., a molecule which does not participate in a subsequent polymerization reaction). In some embodiments, the monomers are chosen to provide the desired functional groups (e.g., hydroxyl, carboxyl, amino, thiol, etc. groups) on the polymer, so that the desired probes can subsequently be attached to the functional groups to complete the sensor.

As further described herein, probe size is a factor to be considered when attempting to optimize polymer chain density. Stated another way, the average distance between the polymer chains depends, at least in part, upon the size of the probes to be attached, as well as the sensing process to be employed. Typically, however, the average distance between the polymer chain attachment points is less than about 10 times the radius of gyration (Rg) of polymer chain under the conditions of the assay being employed, preferably less than about 4 times Rg, and more preferably less than about equal to twice the Rg of the polymer chain. Without being held to a particular theory, it is generally believed that about twice the radius of gyration or more is preferred because, if the polymer chains are further apart than their diameter, then there will be an unnecessary amount of space between them; that is, if the polymer chains are further apart than their diameter there will be empty areas which could be filled with additional polymer chains without causing any significant additional chain overlap and crowding.

Those of skill in the art will also understand that grafting density and molecular weight may be expressed in terms of a "mesh size," which relates to the size of the molecule that may diffuse into, or access, the free volume or space between the polymer chains. Stated another way, for a polymer brush of a given grafting density and molecular weight, a molecular volume or size threshold exists, below which molecules may diffuse into the free volume or space between the chains, while above which the molecules are repelled or prevented from entering this free volume (instead remaining at or near the surface of the polymer layer comprised of the polymer chains). Accordingly, the mesh size of the polymer brush in some embodiments should be sufficient to allow diffusion of the anlyte molecule (e.g., the probe molecule to be attached to the segment functional groups or the target molecule which is to bind with the probe) into this free volume between the surface-bound polymer chains, and preferably in a commercially practical period of time. If there are multiple target analytes, then the mesh should be at least as large as the largest target analyte. Typically, therefore, the mesh size may range from greater than about 0.1, 0.2, 0.5 or even 1 times the radius of gyration of the analyte molecule, up to greater than about 1, 2, 4 or even 5 times the radius of gyration of the analyte molecule. (In other contexts, this theory is discussed in U.S. Pat. No. 5,126,021, which is incorporated herein by reference.)

Examples of anlyte molecules commonly of interest in the art include:

Single-strand DNA: As determined by means common in the art (in this case, Atomic Force Microscopy; see, e.g., Weisenhorn et al., *Scanning Microscopy*, 4(3), 1990, pp. 511–516), the spacing between bases in a single-strand DNA segment is roughly about 5 Å. Because the single-strand DNA is very flexible and can coil upon itself, the width or thickness of a coiled 25 mer is about 6 Å, while the average contour length is about 50 Å.

Additionally, common radii of gyration (Rg) of single-strand DNA of various sizes known in the art (see, e.g., Chan et al., *Biophysical Journal*, 69, 2243–55 (1995)), include:

| Size (# of bases) | Rg (Å) |
|---|---|
| 6 | 10 |
| 30 | 40 |
| 160 | 250 |
| 2686 | 1190 |
| 4373 | 1600 |

Double-strand DNA: As determined by means common in the art (see, e.g., L. Stryer, *Biochemistry*, W. H. Freeman, pp. 76–77 (1988)), a double-strand DNA has a regular structure which is more rigid than the single-strand counterpart, and a length which has been calculated to be about 3.2 Å per base pair. Therefore, a double-strand 25 mer would have a length of about 80 Å, with a helical diameter of about 20 Å, and an estimated radius of gyration of about 45 Å.

Proteins: As determined by means common in the art (see, e.g., Hendrickson et al., PNAS 86, 1989), Streptavidin (SA) has a molecular weight of about 60 kDaltons, with dimensions of about 54×58×48 Å, which equals about 150,336 Å$^3$, and a radius of gyration of about 30 Å. Similarly, Phycoerythrin (PE) has been found to have a molecular weight of about 240 kDaltons, with an estimated molecular volume of about 600,000 Å$^3$, and a radius of gyration of about 50 Å. The SA-PE conjugate molecular volume is about 750,000 Å$^3$ (see, e.g., Glazer, A. Ann., *Rev. Microbiol.*, 36, pp. 173–198 (1982)), and a radius of gyration of about 50 Å.

Related to the concept of free volume between the water-soluble (or water-dispersible) segments bound to the substrate surface is another parameter, referred to herein as the "swelling ratio." Briefly, this is the ratio of the solvated brush thickness to the dry film thickness, and indicates both the degree of expansion of the brush as well as the "free volume" fraction in the solvated brush. The solvated film thickness, as further described herein, may be measured using techniques standard in the art, including neutron scattering and reflectivity, the surface force apparatus, and scanned probe microscopy (such as AFM).

In general, brushes with equivalent dry thickness, but with different molecular weight and grafting density, may demonstrate a significant variation in the degree of swelling and the height of the solvated brush as a function of polymer chain molecular weight. For example, for a 10 Å thick dry film, the solvated thickness is 123 Å for a Mw=10,000 polymer, 573 Å for a Mw=100,000 polymer, and 2660 Å for a Mw=1,000,000 polymer. Thus although the total amount of polymer present per unit area is the same in both cases (expressed, for example, as mass per unit area), the higher molecular weight polymer becomes distributed over a much larger volume, and at much lower concentration, than the lower molecular weight polymer.

Similarly, it can be seen that for the same dry film thickness, the solvated brush made up of a higher molecular weight polymer has a much larger mesh size than a lower molecular weight polymer. For example, for a 40 Å thick dry film, the calculated mesh sizes for solvated brushes having three different molecular weights are 20 Å, 64 Å, and 204 Å, for molecular weights of 10,000, 100,000, and 1,000,000 gm/mole, respectively. As was discussed above regarding the brush height and density, the same number of monomers or the same mass of polymer is distributed in a much more open and accessible way when the polymer has the form of a smaller number of very long segments, versus a larger number of shorter segments.

In general, mesh size depends largely on the absolute grafting density (expressed in picomoles per square centimeter), and not so much on the molecular weight or the dimensionless grafting density. That is, a brush with a specified mesh size can be made to include a larger total volume and total number of binding sites by increasing the molecular weight while keeping the chain grafting density, n, essentially fixed.

The brush structure may be optimized with respect to both sensitivity and kinetics of attachment by always choosing the highest possible molecular weight, and tuning the mesh size and entanglement lifetime via the grafting density. By extending a brush with a very open structure (large mesh size) a great distance away from the substrate, it may be possible to achieve sensitivity much higher than is attainable with brushes commercially available to-date while maintaining a mesh size which is much larger than the size of the biomolecules of interest, thereby permitting very rapid diffusion of the biomolecules throughout the brush and possibly faster kinetics of attachment.

Regardless of the manner by which the "openness" of the brush is defined (i.e., by a swelling ratio, grafting density or mesh size), the important factor to be noted is the free movement of the polymer segments and the ability of molecules of a particular size (e.g., probe or target molecules) to diffuse into the polymer layer comprised of these segments. Accordingly, as mentioned herein, the substantial absence of permanent crosslinks (e.g., covalent crosslinks), and preferably all types of crosslinking, between these segments is preferred so that any entanglements (i.e., obstructions to segmental motion and molecular diffusion or movement) are short lived, thus maximizing the "openness" or mobility of the polymer brush.

The total number of functional groups for the attachment of probe is, at least in part, a function of polymer chain molecular weight, the number of functional groups per polymer chain and the grafting density of polymer chains on the substrate surface. Because of steric hindrance and/or polymer chain overlap, not all functional groups will necessarily be accessible to probe. The number of accessible functional groups may be determined by means common in the art. For example, the number of accessible functional groups, in a given area or volume, may be determined by adding dye molecules to the polymer-coated substrate of the present invention which bind to the accessible functional groups of the polymer chains. Once attached, the dye molecules may then be cleaved from the surface, collected and measured to determine the number of molecules that were attached to the surface, which in turn corresponds to the number of functional groups accessible to the dye molecules. The number of attached, or "cleavable," dye molecules also corresponds to the number of functional groups that would be accessible to probe molecules of a size similar to that of the dye molecules used in the analysis.

While the number of accessible function groups for a given brush configuration will vary with the size of the dye molecules utilized in the test (or, alternatively, the size of the probe molecules to be attached), generally speaking the number of accessible functional groups or sites for small molecules (e.g., small dye molecules having a size of, for example, less than about 10 Å) will typically range from about (i) 20, 25 or even 30 picomoles/cm$^2$, to about (ii) 100, 500, 1000, 5000 picomoles/cm$^2$, up to about (iii) $1\times10^4$, $5\times10^4$, $5\times10^5$, or even $5\times10^6$ picomoles/cm$^2$ (as determined by the cleavable dye analysis methods described herein). However, as the size of the molecule to be attached increases, these ranges may also change. For example, if the molecule to be attached is a protein (which in some cases may have a molecular volume 100 times greater than the dyes molecules referenced above), the number of accessible functional sites for the same surface may range from about 1, 5 or even 10 picomoles/cm$^2$, up to about $1\times10^4$, $1\times10^5$, or even $1\times10^6$. Sizes of common molecules which may be attached to the accessible functional sites include, for example:

Approximate Dye or Probe Size

Fluorescein: D~10 Å
Dansyl choloride: D~10 Å
8 mer ss oligo: Rg~10 Å
25 mer ss oligo: Rg~30 Å
50 mer ss oligo: Rg~100 Å
Streptavidin (SA): D~55 Å
IgG antibody: D~65 Å
Phycoerythrin (PE): D~100 Å
SA-PE conjugate: D~120 Å where D is diameter (used herein for molecules which have a well-defined structure), Rg is radius of gyration (used herein for molecules which do not have a well-defined structure, such as molecules having a random coil structure), ss is single strand and ds is double strand.

It is to be noted that which the Cleavable Dye Analysis may be used to determine the number of accessible functional groups, alternative methods known in the art may also be used to determine the total or actual number of functional groups in the polymer brush. For example, one method involves the use of radioactive or labeled monomers in the polymerization process. Once the polymer chains have been grown, analysis will provide the total number of monomer units that have been incorporated into the brush, which directly correlates to the number of functional groups present.

Density Control—"Dummy" or "Spacer" Molecules

In one embodiment, surface-bound spacer molecules are utilized, which are typically very similar to the surface-bound initiator molecules so that the chemistry of the polymerization reaction is not substantially affected. In some embodiments, the spacers are characterized by the formula:

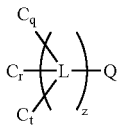

wherein: C is a functional moiety on the surface of the substrate (as defined above); q, r, and t, independently, are 0 or 1; L is a linker group (as defined above) that is capable of bonding to at least one C moiety; z is 0 or 1; and, Q is a group that is substantially incapable of initiating free radical polymerization. Q can be, for example, selected from the group consisting of alkyl, substituted alkyl, alkoxy, substituted alkoxy, aryl, substituted aryl, and combinations thereof.

When bound to a surface, at least one of q, r or t is 1. The above formula shows the spacer or dummy molecules attached to the surface. Thus, the spacer or dummy molecules may be added to the surface by using a molecule that fits the formula $(L)_z$-Q, with the same definitions for L, Q and z.

Because these surface-bound dummy or spacer molecules are incapable of reacting with a monomer or otherwise binding a water-soluble (or water-dispersible) segment as described herein, they perform the role of neutral space-holders, thereby allowing control of the grafting density of the water-soluble (or water-dispersible) segments on the surface. In some embodiments, this control is important to prevent the grafting density of these surface-bound segments from becoming so high the functional groups are not accessible for binding probes and/or the probes are not accessible to the sample components (i.e., the "target" molecules of the sample). The relative concentration of surface-bound initiator (or surface-bound initiator-control adduct) to surface-bound spacer molecules can be selected based upon the surface grafting density desired or needed for a particular application. For example, in some embodiments the concentration of surface-bound spacer molecules exceeds that of the surface-bound initiators (or initiator-control adducts), the ratio ranging from about 1000:1 to about 1:1 (i.e., about 1000:1, 500:1, 100:1, 50:1, 25:1, 10:1, 5:1, etc.), while in other embodiments the concentration of surface-bound initiators exceeds that of the surface-bound spacer molecules, the ratio ranging from about 100:1 to about 1:1 (i.e., about 100:1, 50:1, 25:1, 10:1, 5:1, 3:1, etc.). In other words, in some embodiments the dummy to initiator ratio can range from 100 mol % initiator (i.e., no dummy molecules present) to 0.001 mol % initiator. Typically, however, the dummy to initiator ratio ranges from about 95% initiator/5 mol % dummy to about 1 mol % initiator/99 mol % dummy. Depending upon the molecular weight of the polymer chains attached to the substrate surface and the molecular size of, for example, the probe to be attached, this ratio may range from about 75 mol % initiator/25 mol % dummy to about 10 mol % initiator/90 mol % dummy.

The surface density of initiator or initiator-control adducts can be expressed as a normalized value representing the ratio of the available substrate surface functionalities having an initiator (or initiator control adduct) attached thereto to the total number of such available substrate surface functionalities. For example, when substantially all of the available substrate surface functionalities have an initiator (or initiator control adduct) attached, then the surface is considered to have a polymer chain population distribution of about 1 (assuming each surface bound initiator acts as a site for the initiation of a polymer chain). Further, when about 50% of the available surface functionalities have an initiator (or initiator control adduct) attached and the remainder of the surface functionalities have a dummy molecule attached, then the surface is considered to have a polymer chain population distribution of about 0.5. Similarly, when about 25% of the available surface functionalities have an initiator (or initiator control adduct) attached and the remaining 75% of the surface functionalities have a dummy or spacer molecule attached, then the surface is considered to have a polymer chain population distribution of about 0.25.

Moreover, the population distribution of initiator or initiator-control adducts may be estimated, as a first approximation assuming equally competitive binding, based on the relative amount of dummy or spacer molecules to, when present, the amount of initiator (or initiator-control adduct) in the polymerization mixture. In this manner, those of skill in the art will appreciate how to adjust the population distribution of the polymer chains on the substrate surface, as may be desirable for a particular sensor or application. The chain population distribution, based on the fraction of initiator on the surface to the total number of surface sites (assuming all are occupied by either initiator or dummy molecules), may range from about 0.01 to about 1, more typically from about 0.2 to about 0.8.

In this regard it is to be noted that, as further described herein (see, e.g., discussion below under the heading "Density Calculation"), grafting density may also be calculated based on the molecular weight of the polymer chain segments and the thickness of the polymer layer on the substrate surface. Generally speaking, segment grafting density may range, for at least some embodiments, from greater than about 0.001, 0.01, 0.1 or event 1 picomole/cm$^2$ to greater than about 100 picomoles/cm$^2$ or more. Typically, however, the segment grafting density will range from less than about 1 picomole/cm$^2$ to about 100 picomoles/cm$^2$, from about 2 to about 75 picomoles/cm$^2$, from about 5 to about 55 picomoles/cm$^2$, from about 10 to about 45 picomoles/cm$^2$, or from about 15 to about 35 picomoles/cm$^2$.

Density Control—Controlled Quenching of "Living" Segment Termini

In the case of a "living" system, the termini of the polymer chain segments or blocks which have been formed remain active once all of the monomer present has been consumed or reacted. As a result, additional chain block or segment growth will occur if more monomer is added to the surface. In such instances, the surface density of these subsequent segments will be dependent upon the density of the reactive or living segment ends. Accordingly, the density of these subsequent segments can be reduced, relative to the number of living segments ends, by first rendering a portion of these ends inactive (i.e., terminating or quenching the "living" ends, such that they are incapable of re-initiating polymer chain growth).

Quenching can be achieved by a number of means, including for example chemical, thermal and photochemical. More specifically, quenching can be achieved, for example, by means of: (i) photobleaching, typically employed with photoiniferter systems, wherein the surface is subjected to UV irradiation at a given wavelength (e.g., 254 nm, 366 nm, etc.) for a given period of time (e.g., from about a few minutes (about 2, 5, 10, 20, 30 or more), up to a few hours (e.g., about 2, 4, 6, 8 or even 10)), the light intensity and/or duration of irradiation varying in order to achieve the desired rate and degree of inactivity; (ii) thermal treatment, typically employed with nitroxide systems, wherein the substrate is heated at a given temperature for a given period of time, the temperature and/or duration of the thermal treatment varying in order to achieve the desired rate and degree of inactivity; and, (iii) chemical treatment, typically employed with ATRP (atom transfer radical polymerization) systems, wherein for example the active alkyl halide group is subjected to nucleophilic displacement of the halide.

It is to be note in this regard that the degree of quenching, in the case of the UV/iniferter system, can in some instances also be further dependent upon the initial concentration of monomer in a solvent (and more specifically a solvent which may lead to a transfer reaction), used in the synthesis of the first, hydrophobic layer. For example, it is possible that for a given monomer (e.g., t-butyl acrylamide) and solvent (e.g., DMF), or a particular type of solvent, the "livingness" of the system, and therefore the deactivation or quenching process, can be affected. Furthermore, as the dissociation-recombination between the growing center and the scavenger radical is still occurring in the process, a lower concentration of monomer will decrease the rate of propagation and, therefore, increase the probability of either dissociation-recombination or side reactions that would deactivate the active centers. Additionally, the type of control or chain transfer agent employed may also impact the degree of quenching achieved for a given set of conditions (e.g., duration, wavelength, etc.), more or less stable agents taking more or less time, respectively, to quench. Accordingly, it is to be noted that these factors are to be considered when determining the duration of irradiation and light intensity to be employed, in order to achieve the desired degree of quenching.

In at least some embodiments, use of the photoiniferter process is preferred for growth of the polymer brush, as further described herein, and more specifically the first layer of the polymer brush, followed by photobleaching of the substrate surface prior to the growth of a second polymer layer. Without being held to a particular theory, it is generally believed that, for at least a fraction of the reactive ends, the dithocarbamate extremity of the iniferter cleaves to form a polymer radical and a dithocarbamyl radical, which eventually decomposes.

Regardless of the manner by which quenching is achieved, the number of reactive chain segment ends or termini which remain after quenching has occurred can range from about 10%, 20%, 40%, 60%, 80%, 90% or more, relative to the number of reactive chain segment ends prior to treatment. As a result, the density of a subsequent polymer block (e.g., hydrophilic block, such as a block comprising a water-soluble or water-dispersible segment) can be controlled.

In this regard it is to be noted that, when quenching of some form is employed, control of the initiator to spacer or dummy molecules initially placed on the substrate surface, for growth of the first polymeric (e.g., hydrophobic) layer, is not narrow critical. Stated another way, if quenching is to be employed, the density of the second layer being formed can be controlled exclusively in this way, or by some combination of quenching and initiator to dummy ratio (for growth of the first layer). In one preferred embodiment, wherein a highly dense first layer is desired, only initiator will be placed on the substrate surface, the density of the second layer being controlled exclusively by means of the quenching process.

Additionally, it is to be noted that when a two layer brush (or more) is formed, the chain (or block) density of the second layer may be expressed in terms of the number of blocks relative to the total number of attachment sites on the substrate surface. Accordingly, in view of the discussion provided herein below with respect to density, it is to be noted that in some instances only a fraction of the attachment sites will ultimately be linked to a second polymer chain block (e.g., 1%, 2%, 3%, 4%, 5%, 10%, 20%, 30%, 40%, 50%, 60% or more), while in others substantially all of the of the attachment sites will be linked to a second polymer chain block (e.g., 70%, 80%, 90% or more).

Density Control—Probe/Molecular Size

Figure 7:
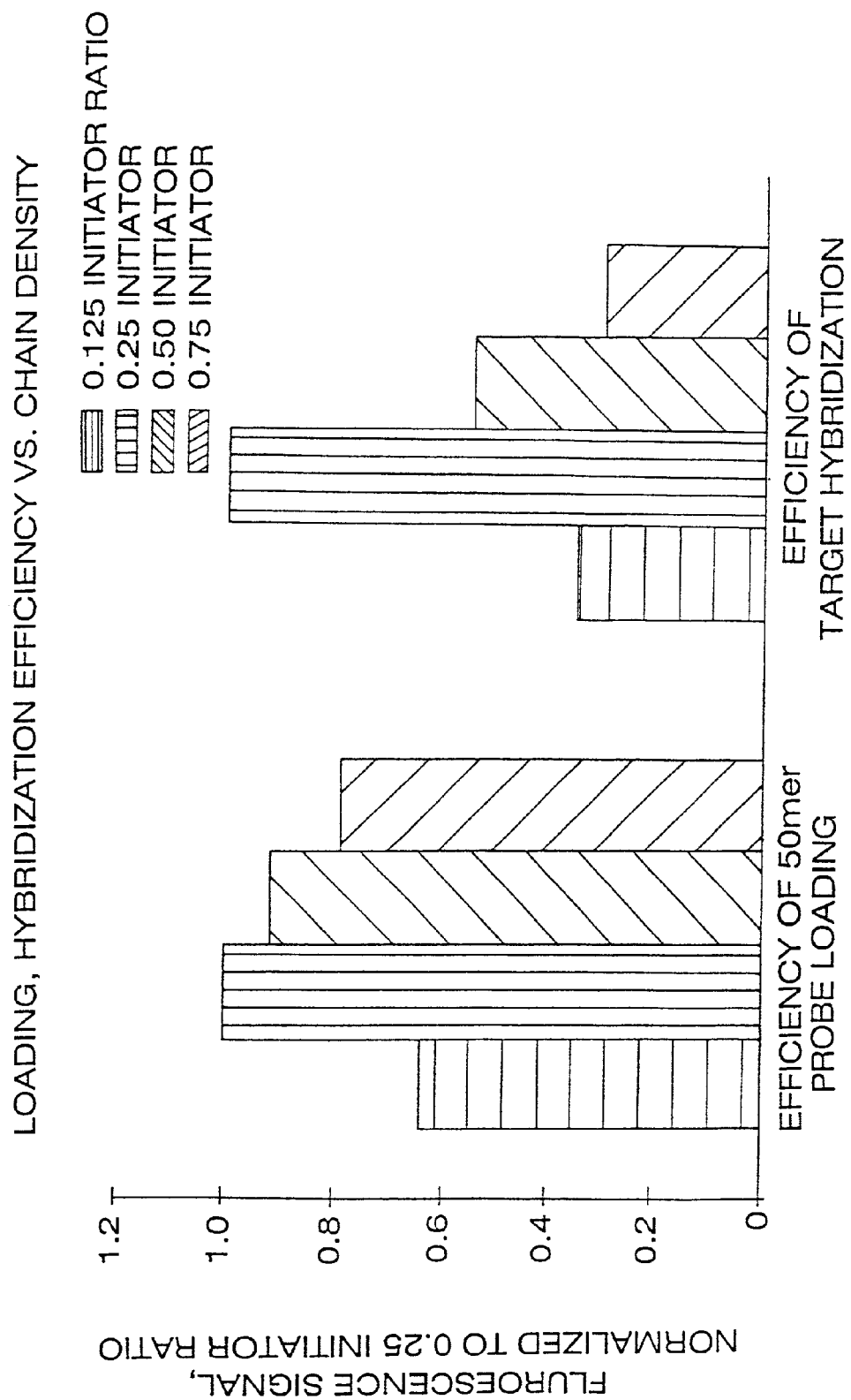
FIG. 7 is a bar graph illustrating efficiency of oligonucleotide loading and hybridization as a function of chain density.

As previously noted, the density of chain segments is an important consideration when optimizing both functional group accessibility for probe attachment, as well as probe accessibility for the attachment of a molecule of interest (i.e., the molecule for which the assay is being performed). Referring to FIG. 7, to a point, the efficiency of probe attachment or loading, as well as attachment or hybridization of the target molecule, increases as the polymer segment density increases. However, at some point a density threshold is reached, at which chain crowding begins to limit the number of probes that can be attached (and thus the number of molecules that can be hybridized). Generally speaking, the density at which crowding becomes a factor tends to decrease as the size of the probe or target molecule increases. This relationship holds particularly true when large probes or target molecules are involved, having average molecular diameters ranging from about 25 angstroms up to about 300 angstroms (e.g., from about 50 to about 250 angstroms, or from about 75 to about 150 angstroms), or more.

In such situations, the density of the polymer chain segments attached to the substrate surface can be controlled, for example, by using and initiator to spacer or dummy molecular ratio on the surface of about 2:98, about 3:97 or even about 4:96; that is, the density is controlled such that the ratio of polymer chain segments to the sum of polymer chain segments and spacers ranges from about 0.02:1 to about 0.1:1, or from about 0.04:1 to about 0.08:1. Similarly, in those instances wherein a first hydrophobic layer is grown from the substrate surface, followed by the growth of water-soluble or water-dispersible segments or blocks there from, the density of the water-soluble or water-dispersible segments can be controlled by quenching about 96%, 97% or even 98% of the reactive or "living" polymer segment ends (by, for example, those methods described above).

Initiators

As noted elsewhere herein, and as shown in FIGS. 2–5, in one embodiment of the present invention the initiator is capable of initiating free radical polymerization with living-type kinetics. Useful molecules for this purpose are initiator-control agent adducts that decompose in situ to yield a control agent and a free radical initiator. "Control agent" is generally used herein to refer to a molecule that comprises a free radical that cannot initiate a polymerization under polymerization conditions, such as those discussed herein. The initiator-control agent adduct can be characterized by the general formula:

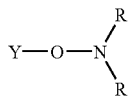

where Y is a residue capable of initiating a free radical polymerization upon cleavage of the Y—O bond (Y being more fully defined below) and each R, which may be the same or different, is independently selected from the group consisting of hydrocarbyl and substituted hydrocarbyl. Optionally, the two R groups may be joined together; that is, each R may be linked to the other by, for example, a hydrocarbylene or heterohydrocarbylene moiety, forming a heterocyclic ring structure with the nitrogen atom. Many free radical control initiators of this type have been disclosed previously, for example, in U.S. Pat. No. 4,581,429, WO 98/30601, WO 96/24620, and WO 99/03894, each of which is incorporated herein by reference.

Again, the above formula shows the initiator-control agent adduct without the linker. For addition to the surface with a linker, the starting molecule takes the form $(L)_z$-Y—O—NR$_2$, with the same definitions for L, Y, R and z as provided elsewhere herein.

In some embodiments, however, the control agents used in this invention are preferably nitroxide control agents having an alpha-destabilizing moiety, X, with alpha-hydrido nitroxide control agents being particularly preferred in such embodiments. Particularly preferred control agent-initiator adducts capable of generating these control agents can be characterized by the general formula:

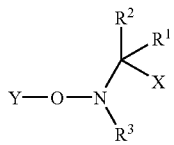

where each of $R^1$, $R^2$ and $R^3$ may be the same or different, and are independently selected from the group consisting of hydrogen, straight chain, branched or cyclic substituted or unsubstituted hydrocarbyl groups, including, for example, alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, silyl, boryl, phosphino, amino, thio, seleno, and combinations thereof. $R^1$ and $R^2$ also may be joined together in a cyclic ring structure; likewise, $R^2$ and $R^3$ may also be joined together in a cyclic ring structure that may have fused with it another saturated or aromatic ring.

It is to be noted that the above formula shows the initiator-control agent adduct without the linker. For addition to the surface with a linker, the molecule takes the form $(L)_z$—Y—O—NR$^3$(CR$^1$R$^2$X), with the same definitions for L, Y, $R^1$, $R^2$, $R^3$, X and z.

The moiety X that is capable of destabilizing the free radical such as, for example, a hydrogen or phosphate group. In this regard it is to be noted that by "destabilizing moiety" or "capable of destabilizing" it is meant that the moiety, X, allows the free radical to destabilize, decompose, destroy, or otherwise remove itself from the reaction (e.g. spontaneously or by interaction with another such control agent), or to be destabilized, be decomposed, be destroyed or be removed from the reaction by the addition of a reagent.

It is to be noted, however, that when X is hydrogen, preferably the $R^3$ moiety is selected from among the group such that, relative to the nitrogen atom, no alpha hydrogens are present in $R^3$. Stated another way, with regard to the preferred nitroxide control agent-initiator adducts, generally represented by the above structure, it is preferred that only one hydrogen atom is alpha to the nitrogen atom. Accordingly, when $R^3$ is alkyl, for example, it is preferred that $R^3$ be a tertiary alkyl moiety. Furthermore, when X is hydrogen, it is preferred that $R^1$ and $R^2$ be other than hydrogen, as well.

For an aqueous solution polymerization, in at least some embodiments it is preferred that one of the R groups ($R^1$, $R^2$ or $R^3$) includes a water-solubilizing group, such as sulfonate, sulfate, carboxylate, hydroxyl, amino, ammonium and the like, to enhance the solubility of the control agent. The presence of monomer in the reaction mixture can, in some cases, also enhance the solubility of the control agent.

In more specific embodiments, each $R^1$, $R^2$ and $R^3$ is independently selected from a group consisting of alkyl, substituted alkyl, cycloalkyl, substituted cycloalkyl, heteroalkyl, substituted heteroalkyl, heterocycloalkyl, substituted heterocycloalkyl, aryl, substituted aryl, heteroaryl, substituted heteroaryl and silyl. Specific examples of $R^1$, $R^2$ and $R^3$ are methyl, ethyl, propyl, butyl, cyclopentyl, cyclohexyl, cyclooctyl, phenyl, benzyl, trimethylsilyl, those specific moieties listed in the above definitions and the like. In alternative embodiments, $R^1$, $R^2$ or $R^3$ may include a water-solubilizing group, such as SO$_3$G, where G is Na, K and the like. In a preferred embodiment, $R^1$ is an aryl (such as phenyl), $R^2$ is an alkyl (such as isopropyl) and $R^3$ is either an alkyl or a heteroalkyl (such as tert-butyl or Me$_3$SiOCH$_2$(CH$_3$)$_2$C). In an alternative preferred embodiment, $R^1$ is aryl (such as phenyl), $R^2$ is a cycloalkyl (such as cyclohexyl or cyclopentyl) or a tertiary alkyl (such as tert-butyl) and $R^3$ is either a tertiary alkyl or a heteroalkyl (such as tert-butyl or Me$_3$SiOCH$_2$(CH$_3$)$_2$C). In still another preferred embodiment, $R^1$ is a substituted alkyl (such as NC(CH$_3$)$_2$C) and $R^2$CNR$^3$ form a cyclic ring structure.

Y is a residue capable of initiating free radical polymerization upon homolytic cleavage of the Y—O bond, including, for example, alkyl, substituted alkyl, alkoxy, substituted alkoxy, heteroalkyl, substituted heteroalkyl, aryl, and substituted aryl residues. Use of such adducts can eliminate concerns about the speed of initiation of polymer chains, effectively initiating all polymer chains at substantially the same time upon addition of the adduct to the monomer under polymerization conditions. The adducts may be prepared by methods known in the art, such as those disclosed in WO 99/03894, which is incorporated herein by reference. In another such embodiment, the control agent is generated in situ from the nitrone precursor, as is also discussed in WO 99/03894. The adducts are, for polymerization in aqueous solution, preferably water soluble, or at least water soluble in the presence of the monomer.

In yet another embodiment, the adducts useful in this invention encompass compounds having a monomer, oligomer or polymer disposed between the Y residue and the oxygen atom of the adduct, as shown in the formula below.

Thus, embodiments including compounds of the structure shown in this formula are within the definition of "adduct" as that term is applied to the invention; that is, the growing polymer chain, as well as the "capped" chain, can themselves be considered adducts (with $Y'$-$(M)_n$- being considered the Y moiety). An adduct comprising an oligomer or polymer of this invention may be characterized by the formula:

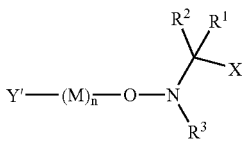

wherein: $R^1$, $R^2$, $R^3$ and X have the above-recited meanings and scope; Y' can be the same as Y (as recited above); M is one or more monomer units selected from the monomers described herein; and n is zero, 1, or greater than 1. Thus, for example, when n is zero, the compound of the formula collapses to the compound of the previous formula. When n equals 1, the compound of this formula can be considered a first-monomer adduct. When n is 2 or more, the compounds of this formula are considered to be oligomer adducts or polymer adduct. All of such various adducts are capable of initiating the free radical polymerizations of the invention.

The above formula shows the initiator-control agent adduct without the linker. For addition to the surface with a linker, the molecule takes the form $(L)_z$-Y-$\alpha$-$(M)_n$-ONR$^3$(CR$^1$R$^2$X), with the same definitions for L, Y, $R^1$, $R^2$, $R^3$, X and z. If attached to the surface, the previously defined C would be added to this formula.

It is frequently convenient to generate the Y (or Y') radical in the presence of monomer and control agent, and to isolate an adduct where n ranges from 1 to about 5, is preferably 2 or 3, and is more preferably 1. These are isolable compounds that can be easily purified and used in subsequent polymerization processes of the invention.

Monomers—Generally

The polymers may be prepared from a variety of monomers. A particularly useful class of water-soluble or water-dispersible monomers, for at least some embodiments, features acrylamide monomers having the formula:

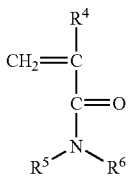

wherein: $R^4$ is H or an alkyl group; and $R^5$ and $R^6$, independently, are selected from the group consisting of hydrogen, alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, and combinations thereof; $R^5$ and $R^6$ may be joined together in a cyclic ring structure, including heterocyclic ring structure, and that may have fused with it another saturated or aromatic ring. One preferred embodiment is where $R^5$ and $R^6$, independently, are selected from the group consisting of hydroxy-substituted alkyl, polyhydroxy-substituted alkyl, amino-substituted alkyl, polyamino-substituted alkyl and isothiocyanato-substituted alkyl. In preferred embodiments, the polymers include the acrylamide-based repeat units derived from monomers such as acrylamide, methacrylamide, N-alkylacrylamide (e.g., N-methylacrylamide, N-tert-butylacrylamide, and N-n-butylacrylamide), N-alkylmethacrylamide (e.g., N-tert-butylmethacrylamide and N-n-butylmethacrylamide), N,N-dialkylacrylamide (e.g., N,N-dimethylacrylamide), N-methyl-N-(2-hydroxyethyl)acrylamide, N,N-dialkylmethacrylamide, N-methylolmethacrylamide, N-ethylolmethacrylamide, N-methylolacrylamide, N-ethylolacrylamide, and combinations thereof. In another preferred embodiment, the polymers include acrylamidic repeat units derived from monomers selected from N-alkylacrylamide, N-alkylmethacrylamide, N,N-dialkylacrylamide and N,N-dialkylmethacrylamide. Preferred repeat units can be derived, specifically, from acrylamide, methacrylamide, N,N-dimethylacrylamide, and tert-butylacrylamide.

Copolymers can include two or more of the aforementioned acrylamide-based repeat units. Copolymers can also include, for example, one or more of the aforementioned polyacrylamide-based repeat units in combination with one or more other repeat units. The monomers are selected such that the resulting copolymer contains water-soluble or water-dispersible segments. Examples of other such repeat units include those derived from monomers suitable for forming copolymers such as styrene, substituted styrene, alkyl acrylate, substituted alkyl acrylate, alkyl methacrylate, substituted alkyl methacrylate, acrylonitrile, methacrylonitrile, isoprene, butadiene, ethylene, vinyl acetate and combinations thereof. Functionalized versions of these monomers may also be used. Specific examples include methyl methacrylate, ethyl methacrylate, propyl methacrylate (all isomers), butyl methacrylate (all isomers), 2-ethylhexyl methacrylate, isobornyl methacrylate, methacrylic acid, benzyl methacrylate, phenyl methacrylate, methacrylonitrile, $\alpha$-methylstyrene, methyl acrylate, ethyl acrylate, propyl acrylate (all isomers), butyl acrylate (all isomers), 2-ethylhexyl acrylate, isobornyl acrylate, acrylic acid, benzyl acrylate, phenyl acrylate, acrylonitrile, styrene, glycidyl methacrylate, 2-hydroxyethyl methacrylate, 2-hydroxyethyl methylacrylate, hydroxypropyl methacrylate (all isomers), hydroxybutyl methacrylate (all isomers), N,N-dimethylaminoethyl methacrylate, N,N-diethylaminoethyl methacrylate, triethyleneglycol methacrylate, itaconic anhydride, itaconic acid, glycidyl acrylate, 2-hydroxyethyl acrylate, hydroxypropyl acrylate (all isomers), hydroxybutyl acrylate (all isomers), N,N-dimethylaminoethyl acrylate, N,N-diethylaminoethyl acrylate, triethyleneglycol acrylate, vinyl benzoic acid (all isomers), diethylaminostyrene (all isomers), $\alpha$-methylvinyl benzoic acid (all isomers), diethylamino a-methylstyrene (all isomers), p-vinylbenzene sulfonic acid, p-vinylbenzene sulfonic sodium salt, trimethoxysilylpropyl methacrylate, triethoxysilylpropyl methacrylate, tributoxysilylpropyl methacrylate, dimethoxymethylsilylpropyl methacrylate, diethoxymethylsilylpropyl methacrylate, dibutoxymethylsilylpropyl methacrylate, diisopropoxymethylsilylpropyl methacrylate, dimethoxysilylpropyl methacrylate, diethoxysilyl propyl methacrylate, dibutoxysilylpropyl methacrylate, diisopropoxysilylpropyl methacrylate, trimethoxysilylpropyl acrylate, triethoxysilylpropyl acrylate, tributoxysilylpropyl acrylate, dimethoxymethylsilylpropyl acrylate, diethoxymethylsilylpropyl acrylate, dibutoxymethylsilylpropyl acrylate, diisopropoxymethylsilylpropyl acrylate, dimethoxysilylpropyl acrylate, diethoxysilylpropyl acrylate, dibutoxysilylpropyl acrylate, diisopropoxysilylpropyl acrylate, maleic anhydride, N-phenylmaleimide, N-butylmaleimide, butadiene, isoprene, chloroprene, ethylene, vinyl acetate, 2-(2-oxo-1-imidazolidinyl)ethyl 2-methyl-2-propenoate, 1-[2-[[2-hydroxy-3-(2-propyl)propyl)]amino]ethyl]-2-imidazolidinone, N-vinyl pyrrolidone, N-vinylimidazole, crotonic acid, vinyl sulfonic acid, and combinations thereof.

As further described herein, it is to be noted that the attachment of probes or other molecules to the water-soluble or water-dispersible segment of the polymer chain may be achieved by a number of ways including, for example: (i) post-polymerization activation and derivatization (wherein the probe molecules react with the functional moieties on the segments after polymerization, and after the moieties have been activated, as further described herein); (ii) post-polymerization derivatization (wherein the probe molecules react directly with active functional moieties, the moieties having been formed in their active state as part of the polymerization process); and, (iii) the monomers are modified so as to include the probe molecules prior to polymerization. Alternatively, however, it is to be further noted that these water-soluble or water-dispersible segments can be derived from hydrophobic polymers prepared from hydrophobic monomers, these polymers subsequently being made water-soluble or water-dispersible by means of, for example, alkylation, phosphorylation, carboxylation, amination, sulfonation, sulfatation, metallation and the like.

Monomers Which do not Require Activation for Probe Attachment

As previously noted, the attachment of probes or other molecules to the water-soluble or water-dispersible segment of the polymer chain may be achieved by a number of methods including, for example, subjecting the functional groups (e.g., hydroxyl or amino groups) of these segments to some activation process (i.e., some linking chemistry to enable probe attachment). However, in some embodiments of the present invention, the monomers from which the polymer chains are derived may themselves possess functional groups that will directly attach the probe molecules; that is, the monomers from which the polymer chains attached to the substrate surface are derived may possess functional groups that will directly react with and attach the desired probe molecules, without the need of some additional derivatization step (e.g., linking chemistry, such as hydroxylation or amination) to activate the functional groups for probe attachment.

Generally speaking, in some embodiments of the present invention the monomer may be represented by the following formula:

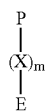

wherein P is a functional group that polymerizes in the presence of free radicals (e.g., a carbon-carbon double bond), and E is a group that can react with the probe of interest and form a chemical bond therewith. The bond which forms between E, or a portion thereof, and the probe in most cases is covalent, or has a covalent character. It is to be noted, however, that the present invention also encompasses other type of bonds or bonding (e.g., hydrogen bonding, ionic bonding, metal coordination, or combinations thereof). One example of the latter is when the E group contains a metal complexing agent that can bind a protein through a mixed complex: E can be, for instance, a ligand, such as iminodiacetic acid that can bind histidine tagged proteins through Ni mixed complexes.

In another embodiment, E is a phenylboronic acid moiety, which can strongly complex to biological probes that contains certain polyol molecules (e.g., 1,2-cis diols or other related compounds). In one preferred embodiment, E is an electrophilic group that, upon reaction with a nucleophilic site present in the probe, forms a chemical bond with the probe. Such activated monomers include, but are not limited to, N-hydroxysuccinimides, tosylates, brosylates, nosylates, mesylates, etc. In other embodiments, the electrophilic group consists of a 3- to 5-membered ring which opens upon reaction with the nucleophile. Such cyclic electrophiles include, but are not limited to, epoxides, oxetanes, aziridines, azetidines, episulfides, 2-oxazolin-5-ones, etc. In still other embodiments, the electrophilic group may be a group wherein, upon reaction with the nucleophilic probe, an addition reaction takes place, leading to the formation of a covalent bond between the probe and the polymer. These electrophilic groups include, but are not limited to, maleimide derivatives, acetylacetoxy derivatives, etc.

With respect to X, it is to be noted that, when present (i.e., when m is not equal to zero), X represents some linking group which connects P to E, such as in the case of X linking an unsaturated carbon atom of P to an electrophilic E group. X may be, for example, a substituted or unsubstituted hydrocarbylene or heterohydrocarbylene linker, a hetero linker, etc., including linkers derived from alkyl, amino, aminoalkyl or aminoalkylamido groups. In such instances, m is an integer such as 1, 2, 3, 4 or more. In other embodiments (i.e., when m is equal to zero), P is directly bound to E.

In one preferred embodiment, X is a linker generally represented by the formula

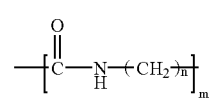

wherein n is an integer from about 1 to about 5, and m is an integer from about 1 to about 2, 3, 4 or more. In one such embodiment, preferred monomers include those having an N-hydroxysuccinimide group. For example, certain of such monomers may generally be represented by the following formula:

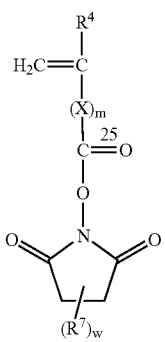

wherein $R^4$ is a hydrogen or an akyl substitutent, and $R^7$ is one or more substituents (i.e., w is 1, 2, 3, 4) selected from the group consisting of hydrogen substituted or unsubstituted hydrocarbyl (e.g., alkyl, aryl, heteroalkyl), heterohydrocarbyl, alkoxy, substituted or unsubstituted aryl, sulphates, thioethers, ethers, hydroxy, etc. Generally speaking, $R^7$ can essentially any substituent that does not substantially decrease the hydrophilic of the water-soluble or water-dispersible segment in which it is contained. In this regard it is to be noted that a number of substituted succinimide compounds are commercially available and are suitable for use in the present invention.

Among the particularly preferred monomers is included N-acryloxysuccinimide and 2-(methacryloyloxy)ethylamino N-succinimidyl carbamate, which are generally represented by the formulas:

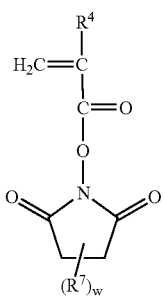

where $R^4$, $R^7$ and w are as previously defined. Also preferred are those monomers represented by formulas (III) and (IV) below, wherein the terminal carbonyl-oxo-succinimide group is positioned further from the polymer chain backbone by the presence of a aminoalkyl or aminoalkylamido linker (i.e., "X"), respectively:

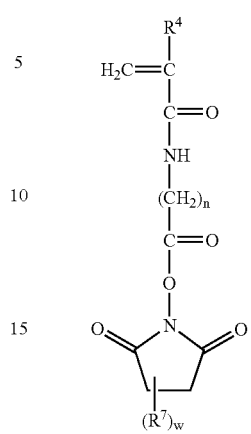

(III)

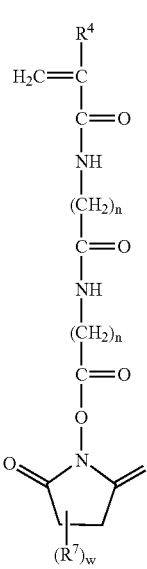

(IV)

where $R^4$, $R^7$, n and w are as previously defined. Alternatively, however, monomers such as 2-(methylacryloyloxy) ethyl acetoacetate, glycidyl methacrylate (GMA) and 4,4-dimethyl-2-vinyl-2-oxazolin-5-one, generally represented by formulas (V), (VI) and (VII), respectively, may also be employed (wherein $R^9$ is hydrogen or hydrocarbyl, such as methyl, ethyl, propyl, etc., as defined herein).

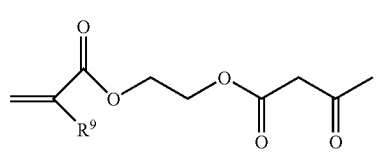

(V)

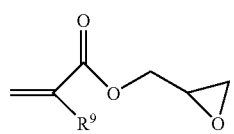

(VI)

-continued

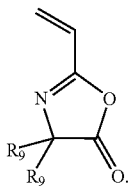

(VII)

Figure 8A:
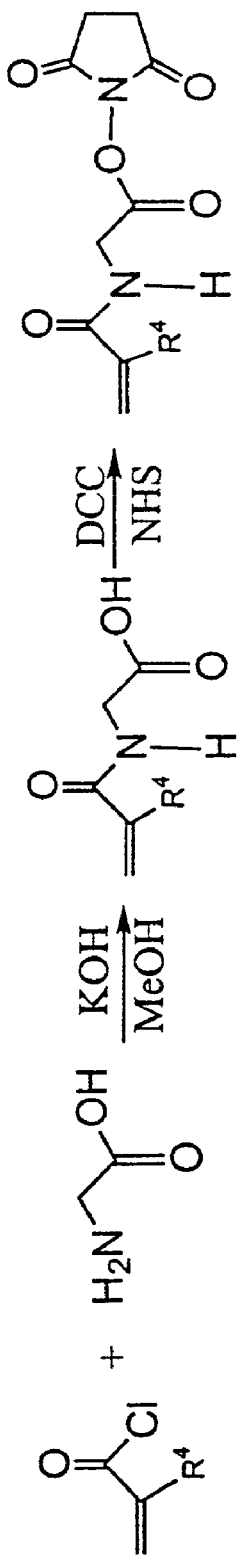
FIGS. 8a and 8b generally represent reaction schemes that can be employed to prepare monomers for use in some embodiments of the present application, having functional groups which do not require "activation" prior to, for example, DNA probe attachment.
Figure 8B:
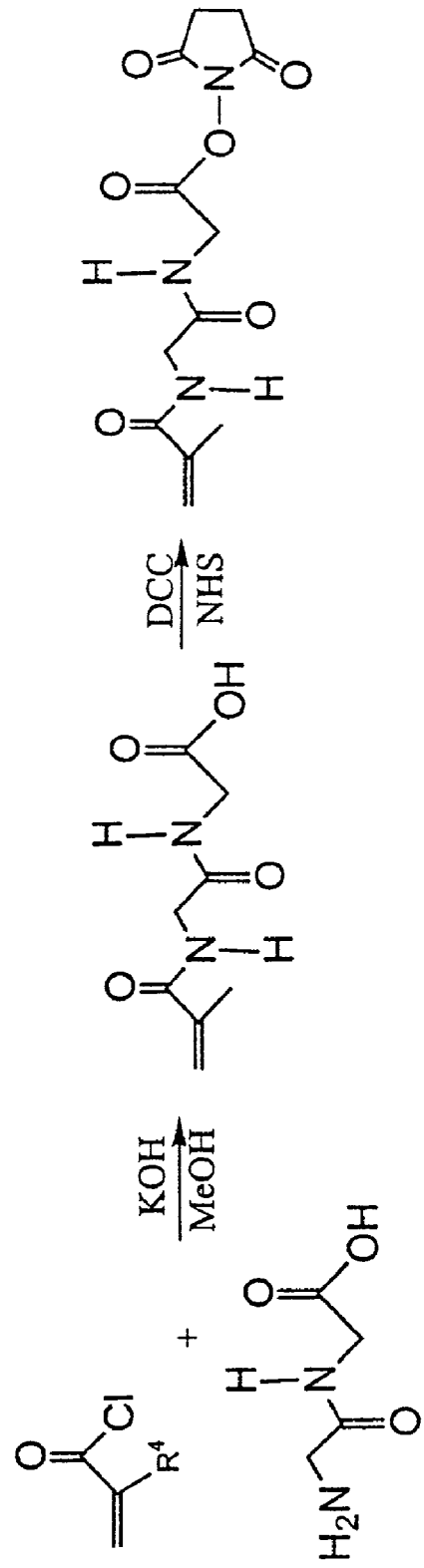
Figures 10A, 10B:
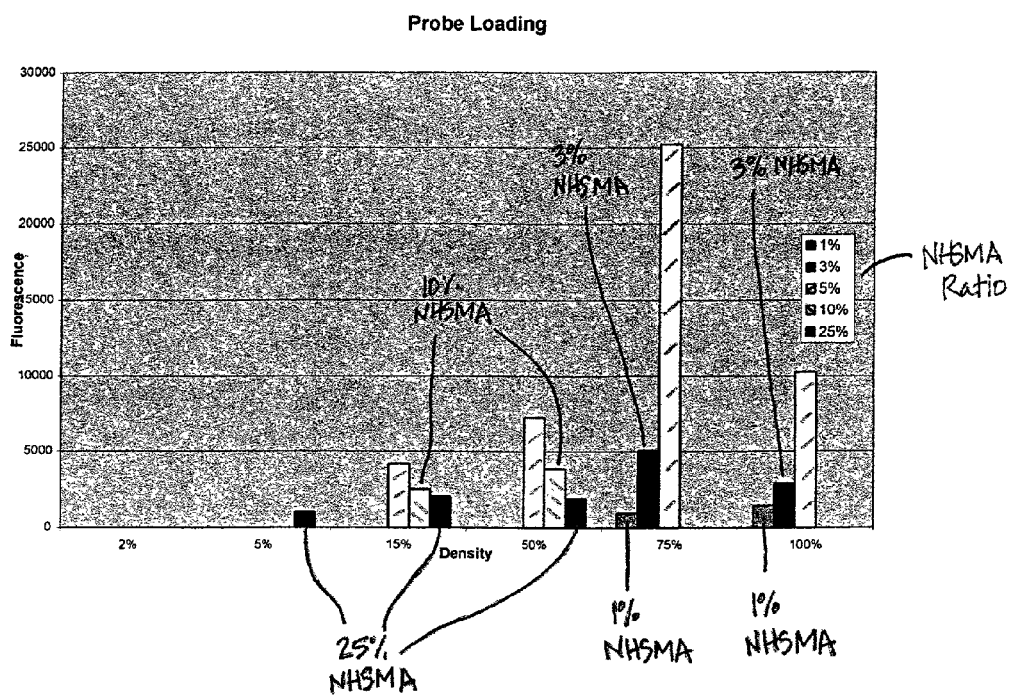
FIGS. 10a an 10c provide tables of exemplary data for probe loading and hybridization signal (10a and 10c, respectively), while corresponding FIGS. 10b and 10d graphically illustrate this data versus chain density and monomer ratio, for polymer containing NHSMA groups; that is, these FIGS. collectively illustrate the dependence of the fluorescent count on chain density and monomer ratio, after coupling and hybridization of amino-modified oligonucleotides on polymer brushes containing NHS groups (as further described in Example 22).
Figures 10C, 10D:
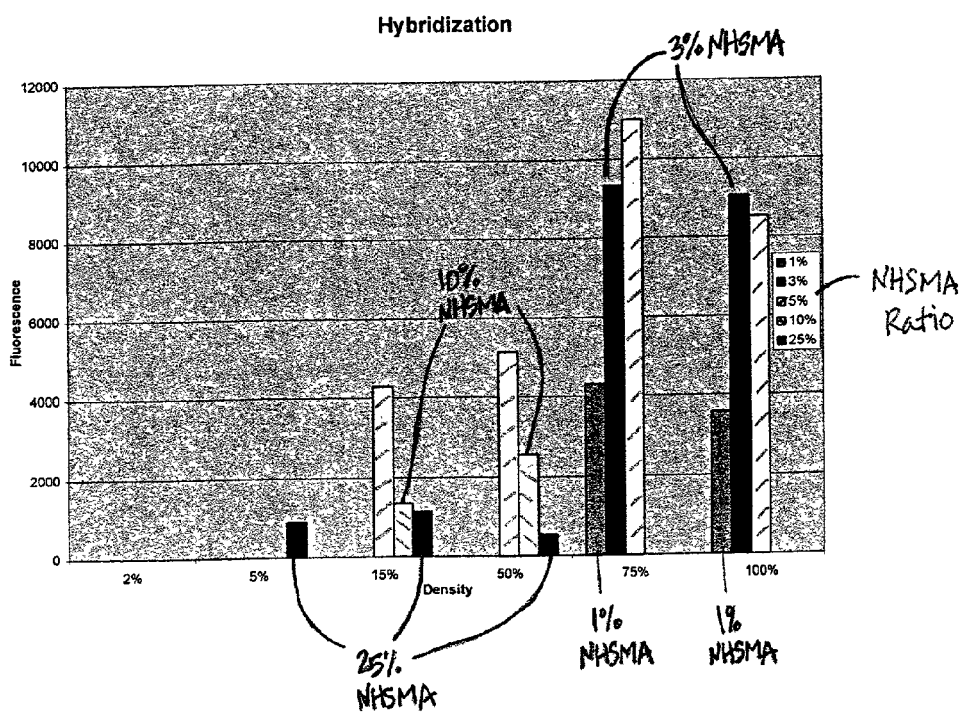

One or more of the above referenced monomers (e.g., N-acryloxysuccinimide, 2-(methylacryloyloxy)ethyl acetoacetate, glycidyl methacryl ate and 4,4-dimethyl-2-vinyl-2-oxazolin-5-one) are commercially available, for example from Aldrich Chemical Company. Additionally, monomers generally represented by formulas (III) and (IV), above, may be prepared by means common in the art, such as by employing the reaction scheme generally represented in FIGS. 8a and 8b, respectively (wherein in each case n=1).

It is to be noted that such monomers may advantageously be employed in any of the polymerization processes described herein, including nitroxide and iniferter initiated systems.

Monomers Which Display Pre-Coupled Probes

As one alternative to the "pre-activated" embodiment described herein, it is to be noted that polymers can also be formed from monomers that already display or possess the molecular probes of interest. In this approach, the polymerization process forms a brush which already contains the biological probes of interest, thus eliminated the subsequent steps of polymer activation and/or probe attachment. By way of illustration, (i) monomers that display or contain a ligand such as biotin are capable of binding proteins from the avidin family, (ii) monomers that display a particular sequence of oligonucleotide are capable of hybridizing nucleic acids containing the complementary sequence, (iii) monomers that display a molecular drug candidate may be used to screen proteins that interact or bind or are inhibited by the monomer's active moieties.

It is to be noted that, in some instances, the size of the probe attached to the monomer may need to be taken into consideration, in order for example to avoid hindering the efficiency of the polymerization process. In such instances, the probe to monomer size ratio is typically less than 100:1, and preferably is less than about 50:1, more preferably less than about 20:1, still more preferably less than about 10:1, and still more preferably is less than about 5:1 (e.g., less than about 4:1, 2:1, or even 1:1).

Additionally, it is to be noted that, depending on the class of the probe, the probe may bear a molecular moiety (such as, for example, an amine group, a carbonyl group, a thiol group, etc.) that may be vulnerable to, or also interfere with, the process of polymerization. In this event, the probe itself may need to be chemically protected during the polymerization reaction, using means known in the art. In such instances, a subsequent deprotection step may be need, if for example the protecting group interferes with probe affinity or recognition after polymerization.

These pre-formed monomers may display several classes of probes, which are described further herein below. As an example, one class of suitable probe for certain embodiments is nucleic acid-containing probes, such as nucleic acid polymers (i.e., DNA, RNA, PNA and derivatives thereof), as further described herein. Nucleic acid polymer probes are generally at least about six nucleotides in length, and can range in size up to the length of an entire chromosome. Typically, nucleic acid probes are oligonucleotides that are about 8 to 100 nucleotides in length (e.g., ranging from about 15 to 30, 40, 50 nucleotides) or complementary DNA fragments ("cDNA") that are partial or complete (e.g., having 100 to 5,000 nucleotides). Amino acid polymers, such as polypeptides, represent a second class of useful probes. Additional probes are described further below.

The Polymerization Process—Preparation of Polymer Brushes

In one embodiment of the present invention, the polymerization reaction is a controlled, living free radical polymerization reaction (such as that of the type generally described in Husseman et al., Macromolecules 1999, 32, 1424–31, the contents of which are hereby incorporated by reference). More specifically, in the process, the substrate surface is analyzed to estimate or specifically determine the amount of surface functionalities that are available for binding the polymer chains via one of the methods discussed herein. If necessary, the surface is modified to adjust the amount (e.g., concentration per unit area or location on the surface) and type of surface functionality, for example by acid treatment or coating the surface. After the surface is prepared, in accordance with various embodiments of the present invention, the initiators, initiator-control adducts and/or dummy or spacer molecules may be attached to the surface via the surface functionalities; that is, once the substrate surface has been prepared, one or more of these may be attached to the surface or, alternatively, added in solution at some point during the polymerization process (as further described in detail below in the general procedure portion of the example section). In those embodiments wherein the surface is to be further modified, typically before doing so the desired surface grafting density of the polymer chain segments is determined.

In those embodiments wherein the substrate surface is further modified prior to initiation of polymerization, such as by the attachment of initiators or initiators-control adducts and/or dummy molecules to the substrate surface, the substrate surface is generally referred to herein as a "derivatized surface." Subsequently, the derivatized surface is placed into a polymerization system that contains the desired monomers. As discussed below, unbound or "free" initiators or initiator-control adduct, which generally refers to initiators or initiator-control adducts that are not bound to the substrate surface, can also be included in the polymerization system. Accordingly, in one embodiment the polymerization system includes at least the desired monomers, the derivatized surface and the unbound initiators or initiator-control adducts under polymerization conditions, while in a second embodiment no unbound initiators or initiator-control adducts are present in the polymerization system.

For controlled radical polymerizations generally, when present, the number of unbound initiators or initiator-control adducts may be greater than the number of bound initiators or initiator-control adducts. The addition of unbound initiators or initiator-control adducts, therefore, creates an overall concentration of control agent in the polymerization system which is believed to control the growth of both bound (insoluble) and unbound (e.g., typically soluble) polymer chains. In general, depending on the surface and the method used to polymerize the polymer, a useful range for the ratio of the number of unbound initiator or initiator-control agent adduct to number of surface bound initiator or initiator-control agent adduct is from about zero:1 to about $1 \times 10^7$:1.

Thus, when the ratio is zero, there is no unbound initiator or initiator-control agent adduct. In those embodiments wherein unbound initiator or initiator-control agent adduct is present, preferably this ratio is not less than about 10:1, where the unbound initiator or initiator adduct is at least 10 times greater than the bound initiator or initiator adduct.

By having both bound and unbound adducts, polymerization results in the formation of both bound and unbound polymers. The unbound polymer can then be removed, e.g., by washing the derivatized substrate with water or other solvent to yield the article. As discussed elsewhere, the bound polymer chain ends may be modified, for example to remove the control agent and replacement of the same with a functionality. Also, it will be appreciated by those of skill in the art that only the derivatized surface, or a portion thereof, needs to be exposed to the polymerization system. In other embodiments, the entire substrate may be immersed in the polymerization mixture.

Using both bound and unbound adducts overcomes the problem associated with many surface polymerizations of not being able to form a sufficient number of polymer chains bonded to the surface. Moreover, because both the bound and unbound polymers are formed under the same conditions, they can have substantially the same composition. Accordingly, the unbound polymer can be analyzed to determine properties such as molecular weight, extent of branching, etc. and thereby provide a convenient way of determining the properties of the bound polymer without disturbing the bound polymer. Furthermore, the molecular weight of the unbound polymer can be correlated with the thickness of the polymer layer on the surface. The amount of incorporated functional group containing co-monomer can be determined by $^1$H NMR spectroscopy of the unbound polymer.

It is to be noted, however, that "free" initiator is not required and, in some cases, may preferably be absent from the polymerization system. When free initiator is not present, the polymerization reaction may be controlled by using an unbound control agent in the polymerization mixture such as, for example, a nitroxide radical control agent having the general formula:

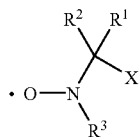

In this approach, polymer growth is monitored by measuring the polymer layer thickness (e.g. by ellipsometry). The molecular weight may then be calculated from the thickness of a substrate with a known density of initiating sites. The appropriate concentration of the stable free radical to be added to the polymerization mixture may be determined empirically, or it may be deduced from ESR experiments performed.

Conducting the present process in this manner (i.e., in the absence of free initiator) is advantageous for a number of reasons. For example, because initiator is not present in solution, essentially no polymer is formed therein, which facilitates the washing procedure; that is, because essentially no polymer is formed in the solution, repeated washings are not required to remove the "free" polymer from the surface.

In addition, the approach is comparably more cost effective as a result of the fact that significantly less of what is typically very expensive polymerization initiator can be used.

When no "free" initiator or initiator-control agent adduct is used, chain length may be tuned by the concentration of control agent in solution and the reaction time. For example, high concentrations of control agent will need longer reaction times in order to grow polymers of a given molecular weight. In general, depending upon the surface and the polymerization method used, a useful range of control agent concentration is $1\times10^{-8}$ mol/L to about $1\times10^{-1}$ mol/L.

In one embodiment, the control agent is preferably the nitroxide radical control agent depicted above. However, other preferred embodiment of the present invention, other methods are employed, such as ATRP or iniferter (as further described below), where the control agent is generally a ligated metal at a high oxidation state or a dithio compound, respectively.

Iniferter Process—Generally

When using the iniferter process, the surface-bound initiator has a general formula:

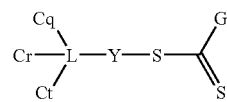

wherein S is sulfur and L, Y, C, q, r and t are as defined elsewhere herein (Y in particular being a residue which, upon cleavage of the Y—S bond, is capable of initiating free radical polymerization, preferably with living-type kinetics). Additionally, G is nitrogen or oxygen (such as in the case of $NR^2_2$ and $OR^3$, respectively, $R^2$ and $R^3$ being as defined herein but typically being hydrocarbyl). The control agent has the general formula:

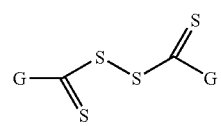

wherein G is as defined above. The reaction is triggered by UV initiation. Such an approach is further described herein with reference to nitroxide-mediated living free radical polymerizations.

Iniferter Process—Photoiniferter Process

As noted, the polymer brushes of the present invention may be formed by several polymerization methods which are standard in the art, including free radical polymerization, and preferably free radical polymerization having living-type kinetics. Such reactions can be carried out using a number of initiators or initiating systems, including nitroxides with heat and photoiniferters with UV.

In this regard it is to be noted that "photoiniferters" may at times be referred to herein generally as initiators or iniferter initiators.

It has been found that, for at least some applications, the iniferter initiators are advantageous for a number of reasons. For example, in comparison to most nitroxide initiators: (i) photoiniferters are significantly less expensive; and, (ii) photoiniferters can be used with a number of different monomer types, enabling a much larger variety of polymers to be formed. Additionally, because polymerization essentially occurs only while the system is exposed to UV light, greater control over the polymerization process is possible.

Generally speaking, the photoiniferter-initiated polymerization process may be carried out by means common in the art. (See, e.g., T. Otsu et al., *Controlled Synthesis of Polymers Using the Iniferter Technique: Developments in Living Radical Polymerization*, Advances in Polymer Science, 136, pp. 75–137 (Springer-Verlag 1998), which is incorporated herein by reference.) Furthermore, the polymerization process may be carried out in bulk or it can be performed in solution (a solvent being used to solubilize the monomer, for example). Although various wavelengths for UV irradiation can be employed (e.g., 254, 365, 366 nm), 366 nm has been found to be suitable for most applications. When using the iniferter process, a surface-bound initiator having a general formula as provided above is typically employed. Preferably, however, embodiments of such initiators include, for example, the surface bound initiators represented by formulas (I) and (II), below:

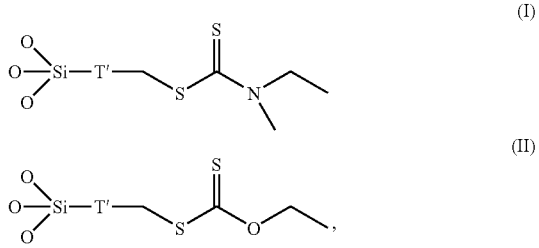

wherein T' generally represents essentially any linker which does not interfere with surface bonding of the silyl group (e.g., substituted or unsubstituted hydrocarbylene, including alkylene, arylene, alkarylene, etc.).

It is to be noted that essentially any of the photoiniferters known in the art can be used in the present invention (such as those disclosed by Braun, wherein initiation is achieved with the loss of nitrogen gas), provided they can be bound to the substrate surface in some way (such as, for example, using the silyl linkage shown).

While this approach can generally be applied to all of the methods for preparing polymer brushes described herein, as further noted below, the iniferter process may be particularly well suited for the preparation of a multilayer brush. More specifically, the iniferter process may be particularly well suited for those applications wherein control of the polymer chain density of a second layer on the substrate surface is desired, such as wherein a first hydrophobic layer is grown from the substrate surface (the iniferter being initially attached to the substrate surface), followed by the growth of a second water-soluble or water-dispersible layer (wherein water-soluble or water-dispersible segments are growth from a portion of the hydrophobic segment ends or termini which are capped by "living" iniferter molecules).

Accelerators

If desired, one or more accelerators may be added to the reaction mixture. Examples of suitable accelerators include alkylating and acylating agents, Lewis Acids, ketones, aldehydes, anhydrides, acid esters, imides, oxidants and reducing agents. Specific accelerators include acetic acid, acetic anhydride, camphor sulfonic acid, other sulfonic acids, acetole (1-hydroxyacetone) and the like. Other accelerators useful herein are recited in Hawker et al., "Development of a New Class of Rate-Accelerating Additives for Nitroxide-Mediated 'Living' Free Radical Polymerization," *Tetrahedron*, Vol. 53, No. 45, pp. 15225–15236 (1997), which is incorporated herein by reference.

Process Conditions/Parameters

Polymerization reaction conditions may be adjusted to control the polymer length and architecture. Polymerization conditions include a temperature in the range of from about minus 40° C. to about 300° C., preferably between about 25° C. and about 200° C., more preferably between about 50° C. and about 150° C., and most preferably between about 70° C. and about 130° C. Alternatively, the temperature may be between about room temperature and 250° C. Polymerization conditions also include a pressure between about ambient pressure up to about 100 atmospheres. The atmosphere may also be one of the polymerization conditions, and the atmosphere may be air, nitrogen, argon or another suitable atmosphere. Polymerization conditions also include the time for reaction, which may be from about 0.5 hours to about 72 hours, preferably in the range of from about 1 hour to about 24 hours, more preferably in the range of from about 2 hours to about 12 hours. The ratios of components (e.g., initiators/control agents, monomers and accelerators) in the polymerization mixture may be important. The initiator to free radical control agent ratio (with the assumption that the amount of initiator is approximately equivalent to the number of radicals produced) is typically in the range of from about 1:0.1 to about 1:4, more preferably the range of from about 1:0.3 to about 1:2 and most preferably the range of from about 1:0.4 to about 1:1.6. Another ratio that may be controlled is the monomer to initiator (or initiator-control adduct) ratio, which typically is in the range of from about 10:1 to about 10,000:1, more preferably the range of from about 100:1 to about 10,000:1 and most preferably the range of from about 100:1 to about 1000:1. When an accelerator is present the ratio of free radical control agent to accelerator is typically in the range of from about 1:0.1 to about 1:4, more preferably the range of from about 1:0.3 to about 1:2 and most preferably the range of from about 1:0.4 to about 1:1.6.

It is to be noted here that, in the case of living-type polymerizations when an excess of unbound initiator or initiator-control agent (as discussed above) is used, it is this excess of unbound initiator or initiator-control agent that determines the monomer to initiator ratio, and thus the molecular weight of the polymer chain in solution as well as on the surface.

A single substrate may have more than one type of polymer chain, including polymer chains with different types, numbers and spacing of functional groups, polymer chains with different molecular weights, etc. In addition, different areas of the substrate surface may feature different arrangements and/or densities of polymer chains. In this way, a single substrate can, if desired, perform multiple analytical operations, making the derivatized substrates particularly useful for complex nucleic acid hybridization studies.

Polymer Architecture

The polymer architecture (including, for example, the identity and length of the polymer chains; the extent, if any, of branching within the chain; the concentration of functional groups, the thickness of the resulting polymer layer, etc.) may be carefully controlled and selected depending on the desired characteristics of the end product. Within these parameters, a large degree of design flexibility is available.

The polymers, for example, can be homopolymers or copolymers prepared from two or more different monomers. The copolymers, in turn, can be random copolymers, block copolymers or graft copolymers. To improve the stability of the water-soluble (or water-dispersible) segment attachment to the surface (or to the linker), a first part of the polymer chain containing the water-soluble (or water-dispersible) segment can be crosslinked and then linear chains may be grown from the crosslinked base. In order to perform this crosslinking a bi-functional monomer may be used.

It is to be noted in this regard, however, that if crosslinking is employed, the crosslinking sites should be spaced sufficiently far from the water-soluble or water-dispersible segments and near the substrate surface in order to ensure maximum mobility of these segments.

As used herein, "block copolymer" refers to a polymer comprising at least two segments of differing composition; having any one of a number of different architectures, where the monomers are not incorporated into the polymer architecture in a solely statistical or uncontrolled manner. Although there may be three, four or more monomers in a single block-type polymer architecture, it will still be referred to herein as a block copolymer. In some embodiments, the block copolymer will have an A-B architecture (with "A" and "B" representing the monomers). Other architectures included within the definition of block copolymer include A-B-A, A-B-A-B, A-B-C, A-B-C-A, A-B-C-A-B, A-B-C-B, A-B-A-C (with "C" representing a third monomer), and other combinations that will be obvious to those of skill in the art. In another embodiment, the block copolymers that may be used in the sensors of this invention include one or more blocks of random copolymer together with one or more blocks of single monomers. Thus, a polymer architecture of A-J, A-J-B, A-B-J, A-J-B-J-C, J-J'-J, etc. is included herein, where J and J' are random blocks of monomers A and B or of monomers B and C. Moreover, the random block can vary in composition or size with respect to the overall block copolymer. In some embodiments, for example, the random blocks J or J' will account for between 5 and 80% by weight of the mass of the block copolymer. In other embodiments, the random blocks J or J' will account for more or less of the mass of the block copolymer, depending on the application. Furthermore, the random block may have a compositional gradient of one monomer to the other (e.g., A:B) that varies across the random block in an approximately algorithmic fashion, with such algorithm being either linear having a desired slope, exponential having a desired exponent (such as a number from 0.1–5) or logarithmic. The random block may be subject to the same kinetic effects, such as composition drift, which would be present in any other radical copolymerization and its composition, and size may be affected by such kinetics, such as Markov kinetics. Any of the monomers listed elsewhere in this specification may be used in the block copolymers. A "block" within the scope of the block copolymers of this invention typically comprises about 10 or more monomers of a single type (with the random blocks being defined by composition and/or weight percent, as described above). In preferred embodiments, the number of monomers within a single block is about 15 or more, about 20 or more or about 50 or more. However, in an alternative embodiment, the block copolymers of this invention include blocks where a block is defined as two or more monomers that are not represented elsewhere in the copolymer. This definition is intended to encompass adding small amounts of a second monomer at one or both ends of a substantially homopolymeric polymer. In this alternative embodiment, the same copolymer architectures discussed above apply. This definition is therefore intended to include telechelic polymers, which include one or more functional end groups capable of reacting with other molecules. Thus, generally, a telechelic polymer is a block copolymer within the definitions of this invention. The functional groups present at one or both ends of a telechelic polymer may be those known to those of skill in the art, including, for example, hydroxide, aldehyde, carboxylic acid or carboxylate, halogen, amine and the like, which have the ability to associate or form bonds with another molecule.

The polymer chains may be linear or non-linear. Examples of non-linear molecules include branched and star polymers. The star molecules typically have anywhere between 2 and 12 arms growing from a common core, although structures having more than 12 arms can also be prepared. Branched polymer chains include polymer molecules in which there are side branches of linked monomer molecules protruding from various central branch points along the main polymer chain. Hence a branched polymer molecule can include two or more polymeric segments covalently bonded to each other at a point other than their common ends—either directly (e.g., through functional groups on side chains thereof), or indirectly through a linking moiety. The various "branches" of branched polymers can include polymeric segments having substantially the same or different repeat units, and can themselves be homopolymers or copolymers. The extent of branching is selected based upon the particular application for which the surface-bound polymers are intended.

With respect to crosslinking it is to be noted that, it is typically preferred for the water-soluble (or water-dispersible) segment to have a single point of attachment to the substrate surface (i.e., having a single terminus, as defined herein, attached to the surface) and be substantially free of covalent crosslinking, and preferably all crosslinking. Compared to the permanent entanglements present in a chemically crosslinked gel layer, for example, the entanglements present in a brush composed of singly attached polymer are relatively short lived. These entanglements constantly form and dissipate, so that any loop in the polymer layer which blocks the motion of a biomolecule in a particular direction is temporary. In contrast, in a chemically crosslinked gel, a loop or other obstructing entanglement can act as a permanent impediment or barrier to the movement of a biomolecule through the layer. Thus, in the case of a singly end-grafted brush, penetration of large biomolecules into the brush is facilitated by the dissipation of these entanglements in advance of the moving biomolecule. Therefore, a polymer layer comprised of singly end-attached, non-crosslinked water-soluble (or water-dispersible) segments offers many advantages in comparison to the alternative structures, such as cross linked gel layers or polymer pseudo-brushes where each chain has multiple points of attachment.

The polydispersity index of the polymer can generally range from about 1 to about 100. The polydispersity may be adjusted depending on the application. In the case of living polymerizations, it typically ranges from about 1 to about 2.5, while under certain conditions it may be less than about 2 (range from about 1 to about 2), with values of less than about 1.8, 1.6, 1.5, 1.4, 1.3, 1.2, or even about 1.1 being attainable. Hence, it is possible to control process conditions to achieve a polydispersity index ranging from about 1 to about 1.8, from about 1 to about 1.6, or from about 1 to about 1.5. In a controlled polymerization, the polydispersity typically is less than about 2.

The molecular weight of the polymer chains is adjusted to suit the needs of a particular sensor or application, as discussed in connection with FIG. 1. In general, the molecular weight is adjusted to be sufficiently high such that the functional group-bearing segments (i.e., the water-soluble or water-dispersible segments) are spaced from the surface to the point where they simulate the behavior of a polymer chain in solution with respect to the ability to bond probe molecules to the functional groups. As discussed herein, the polymer chain preferably has a water-soluble or water-dispersible segment that has a molecular weight of at least about 1,000, but can also have a molecular weight of not less than about 2,000, not less than about 10,000, not less than about 50,000, or not less than about 100,000. The incorporation of the functional-group containing monomer may also be calculated relative to other monomer(s) present in the polymer chain. In this context, the relative mole percent of the functional-group containing monomer to other monomer(s) present in the polymer chain may be in the range of from about 1 to 100, more specifically about 2 to 50, without regard to the specific polymer architecture.

Unless otherwise specifically noted, the molecular weight values recited herein are weight-average molecular weights (as determined by size-exclusion chromatography, SEC, performed on polymer chains formed in solution during the polymerization process), based on correlation to narrow linear polystyrene standards. For example, a SEC-observed Mw value of 100,000 means that the measured polymer has the same hydrodynamic volume as the polystyrene of the molecular weight 100,000 under the conditions used for both calibration and characterization (DMF+0.1% TFA) of all samples.

It is to be noted, however, that the actual molecular weight of the polymer may differ from the observed molecular weight, as determined by SEC. For example, in some cases the actual molecular weight may vary from the observed molecular weight of the polymer by at least about +/−10%, 25%, 50% or more. The actual molecular weight, as used herein, means the weight-average of the actual weight of polymer molecules in the polymer based on the actual atomic structure thereof. Because of the inherent difficulties in determining actual molecular weight, however, the actual molecular weight can be approximated by other suitable means. For example, for purposes of the present invention, the actual molecular weight can be approximated as the target molecular weight. The target molecular weight refers to the estimated molecular weight based on the total amount (e.g., moles) of monomer to be incorporated into polymer during the polymerization reaction, as determined by the amount (e.g., moles) of initiator, and the monomer to initiator ratio, assuming that each initiator starts one chain, and that all monomer is incorporated. In situations where initiator efficiency is about 0.9 or less, and/or monomer conversion is less than about 95%, then adjustments for the target molecular weight are made based on initiator efficiency and/or monomer conversion, respectively.

In other embodiments, characterization of the polymer bristle can be accomplished via cleaving the polymers from the surface of the substrate and subsequent analysis, as described above, including chromatography or nuclear magnetic resonance (NMR). The usefulness of this technique depends on the type of surface and the overall amount of polymer available from the cleavage step.

The resulting surface-bound polymer chains include water-soluble or water-dispersible segments having a molecular weight of at least 1,000, preferably at least 2,000 and even more preferably a molecular weight that is adjusted according to the desired length of the polymer chains, which, as discussed elsewhere herein, depends upon, inter alia, the application of the sensors. These segments may be located anywhere along the polymer chain, although they are preferably located at or near the free termini of the chains. These segments further contain functional groups to which probe molecules, described in greater detail, below, can be covalently or non-covalently bonded. Examples of useful functional groups for this purpose include —OH, —COOH, —NH$_2$, —SH, —SCN, —C(O)H, combinations thereof and the like. The selection of useful functional groups is dependent on the application of the sensor, generally, and can be adjusted with the proper selection of monomers. In order to adjust the number of functional groups on the bound polymers, the appropriate concentration of functional group containing monomer is added to the polymerization system, discussed above. Typically, the ratio of functional group containing monomer to non-functional group containing monomer is adjusted to a predetermined ratio prior to adding monomer to the polymerization system. Useful ranges of functional group containing monomer relative to the total amount (volume, mass or moles) of monomer added to the polymerization system include about 0.5% to about 99% function group containing monomer, more specifically from about 10% to about 90%, even more specifically about 15% to about 50% and most specifically about 15% to about 30%.

After the polymerization reaction, in preferred embodiments with living-type polymerizations, the polymer chain end that carries the control agent can be modified, with for example, a reduction step that yields a functional chain end or in a radical exchange step to introduce other functionalities. Probes may be attached to these modified chain ends.

Figure 5:
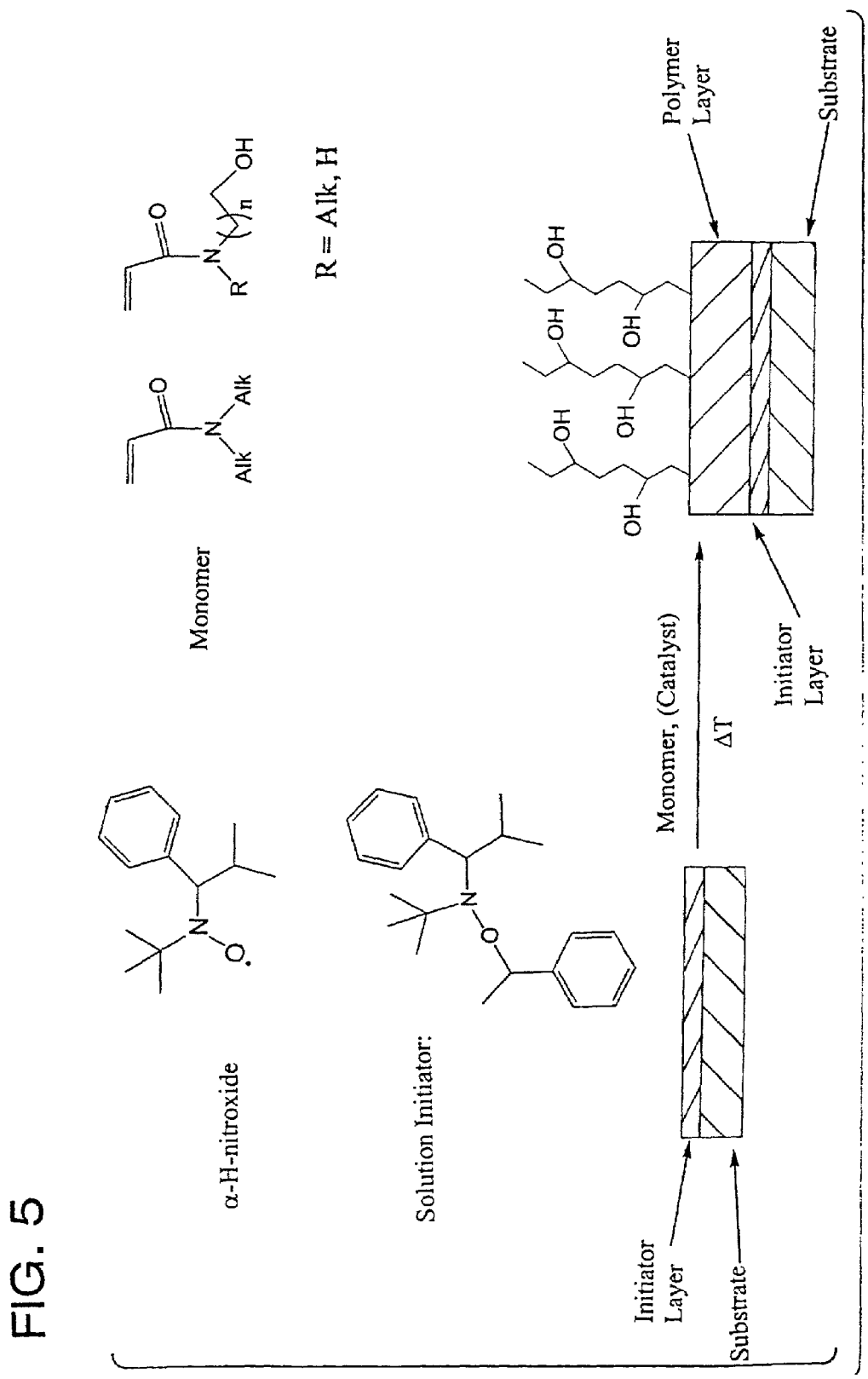

As shown in part of FIG. 5, the polymer-modified surface may be referred to as having a "polymer layer" on top of the surface. The depiction in FIG. 5 actually shows the substrate (e.g., a wafer), an initiator layer (e.g., bound initiator or initiator-control adduct), a "polymer layer" and then some polymer chains on top of the polymer layer. The polymer chains on top of the polymer layer are part of the polymer layer and are shown for illustration purposes to show what the polymer layer comprises in the embodiment shown in FIG. 5. Generally, the polymer-modified surface will have a determinable thickness. The thickness of the polymer layer, measured from the substrate surface, is selected based upon the particular application. In general, however, dry thickness of the polymer layer (either the hydrophobic layer, the hydrophilic layer, or the two layers combined, as further described herein) may in some instances ranges from about 20 to about 2000 angstroms, while in some embodiments this thickness may range from about 30 to about 1500 angstroms, or from about 50 to about 1000 angstroms, all of which are useful for analyzing biological samples of various types.

It is to be noted that the thickness is measured as a dry thickness, in the absence of solvent, by ellipsometry as known to those of skill in the art. See, e.g., "A User's Guide to Ellipsometry", by Harland G. Tompkins (Academic Press (owned/published by Harcourt Brace Jovanovich), 1993), which is incorporated herein by reference. Also, depending on the chain molecular weight and grafting density, as well as the solvent, the polymer chains can also be measured when in the presence of a solvent. This "wet thickness" might be many times the dry thickness. The polymer chain conformation in solvent can also be measured by means known to those of skill in the art (as further described herein).

Probes

A wide variety of biological probes can be employed in connection with the present invention. In general, the probe molecule is preferably substantially selective for one or more biological molecules of interest. The degree of selectivity will vary depending on the particular application at hand, and can generally be selected and/or optimized by a person of skill in the art.

The probe molecules can be bonded to the functional group-bearing polymer segments using conventional coupling techniques (an example of which is further described herein below under the heading "Application"). The probes may be attached using covalently or non-covalently (e.g., physical binding such as electrostatic, hydrophobic, affinity binding, or hydrogen bonding, among others). For example, one technique is the in situ synthesis of probes onto the polymer. See, e.g., Sundberg et al., U.S. Pat. No. 5,919,523 which is incorporated herein by reference. Another technique is the covalent attachment of pre-formed probes (e.g., spotting of probes), which can be achieved as long as a functionality for covalent attachment (such as an amine, hydroxyl, thiol, etc.) is present. Spotting techniques are generally known (see, for example, U.S. Pat. Nos. 5,424,186; 5,677,195; and, 5,744,305, which are incorporated herein by reference for all purposes). In an alternative embodiment, the probes can be bonded, preferably covalently bonded to the monomer units (before polymerization), and then incorporated into the substrate-bound polymer during the polymerization reaction.

Typical polymer brushes functionalities that are useful to covalently attach probes are chosen among hydroxyl, carboxyl, aldehyde, amino, isocyanate, isothiocyanate, azlactone, acetylacetonate, epoxy, oxirane, carbonate sulfonyl ester (such as mesityl or tolyl esters), acyl azide, activated esters (such as N(hydroxy)succinimide esters), O-acylisourea intermediates from COOH-carbodiimide adducts, fluoro-aryle, imidoester, anhydride, haloacetyl, alkyliodide, thiol, disulfide, maleimide, aziridine, acryloyl, diazo-alkane, diazo-acetyl, di-azonium, and the like. These may be provided by copolymerizing functional monomers such as 2-hydroethyl(meth)acrylate, hydroxyethyl(meth)acrylamide, hydroxyethyl-N(methyl)(meth)acrylamide, (meth)acrylic acid, 2-aminoethyl(meth)acrylate, amino-protected monomers such as maleimido derivatives of amino-functional monomers, 3-isopropenyl, αα-dimethylbenzylisocyanate, 2-isocyanato-ethylmethacrylate, 4,4-dimethyl-2-vinyl-2-oxazoline-5-one, acetylacetonate-ethylmethacrylate, and glycidylmethacrylate.

Post derivatization of polymer brushes proves also to be efficient. Typical methods include activation of —OH functionalized groups with, for example phosgene, thiophosgene, 4-methyl-phenyl sulfonylchoride, methylsulfonylchloride, and carbonyl di-imidazole. Activation of carboxylic groups can be performed using carbodiimides, such as 1-ethyl-3-(3-dimethylaminopropyl) carbodiimide hydrochloride, or 1-cyclohexyl-3-(2-morpholinoethyl) carbodiimide, among others. Aldehyde groups can be synthesized from the periodate-mediated oxidation of vicinal —OH, obtained from hydrolysis of epoxy functional brushes. Alternatively, aldehyde groups are attached by reaction of bis-aldehydes (e.g, glutaraldehyde) onto amino-modified polymer brushes. Amino-functional brushes can also be prepared by reacting di-amino compound on aminoreactive brushes, such as N(hydroxy)succinimide esters of carboxylates brushes. (Other state-of-the-art coupling chemistries, such as described in *Bioconjuguate Techniques*, Greg. T. Hermanson, Academic Press, 1996, are also applicable and are incorporated herein by reference.)

One useful class of probes is nucleic acid-containing probes, such as nucleic acid polymers. As used herein, a "nucleic acid" of the nucleic-acid containing probe includes DNA, RNA, and derivatives thereof. For example, the nucleic acid can be DNA or RNA-based molecules containing bases other than adenine, cytosine, guanine, thymine, or uracil (e.g., bromothymine or azaguanine), sugars other than deoxyribose or ribose (e.g., arabinose, 2'-O-methylribose, xylulose, or hoexose), or modified phosphate backbones. A modified phosphate backbone can include, for example, phosphorothioate, phosphorodithioate, phosphoramidothioate, phosphoramidate, phosphordiamidate, methylphosphonate, alkyl phosphotriester, and formacetal linkages, or analogs thereof. In addition, the nucleic acid-containing probe can be a peptide nucleic acid ("PNA"), or an uncharged or possibly positively charged nucleic acid derivative that contains a pseudopeptide backbone. Peptide nucleic acids can be produced using standard techniques as described, for example, in U.S. Pat. No. 5,539,082, which is hereby incorporated by reference.

Nucleic acid polymer probes are typically at least six nucleotides in length, and can range in size up to the length of an entire chromosome. Typically, nucleic acid probes are oligonucleotides that are 8 to 100 nucleotides in length (e.g., 15 to 30, 40, 50 nucleotides) or complementary DNA fragments ("cDNA") that are partial or complete (e.g., having 100 to 5,000 nucleotides).

Nucleic acid probes can be synthesized by standard methods known in the art such as, for example, by use of an automated nucleic acid synthesizer of the type commercially available from Biosearch and Applied Biosystems. Phosphorothioate oligonucleotides can be synthesized according to the method of Stein et al. (*Nucleic Acids Res.*, 1988, 16:3209–3221), which is hereby incorporated by reference. Methylphosphonate oligonucleotides can be prepared by use of controlled pore glass polymer supports, as described by Sarin et al. (*Proc. Natl. Acad. Sci. USA*, 1988, 85(20): 7448–7451).

Nucleic acid probes also can be isolated from genomic DNA, total cellular RNA, or messenger RNA ("mRNA") using standard methods known in the art. For example, the nucleic acid probes may be obtained from microdissected RNA, a clone set from a genome of interest (e.g., a set of expressed sequence tags ("ESTs") or a cDNA library), a restriction enzyme fragment, or a polymerase chain reaction ("PCR") product. PCR refers to a procedure or technique in which target nucleic acids are amplified. Generally, sequence information from the ends of the region of interest or beyond is employed to design oligonucleotide primers that are identical or similar in sequence to opposite strands of the template to be amplified. PCR can be used to amplify specific sequences from DNA as well as RNA (reverse-transcriptase PCR), including sequences from total genomic DNA or total cellular RNA. Primers are typically 14 to 40 nucleotides in length, but can range from 10 nucleotides to hundreds of nucleotides in length. These primers can be used to incorporate chemical "hooks" for attaching the probe to the activated polymer (e.g., by incorporating a terminal amine, thiol, or biotin moiety). PCR is described, for example, in PCR Primer: A Laboratory Manual, ed. by C. Dieffenbach and G. Dveksler, Cold Spring Harbor Laboratory Press, 1995.

Amino acid polymers, such as polypeptides, represent a second class of useful probes. As used herein, "amino acid polymers" or interchangeably, "polypeptide," refers to a chain of amino acids, regardless of length and regardless of functionality. Typically, the polypeptide is at least 5 amino acid residues in length and can range up to a full-length protein. Short polypeptides can be created using automated synthesis, nearly identical to the above description for DNA with Applied Biosystems instrumentation. Moreover, the polypeptide can have a known or suspected functionality or partial functionality (e.g., as a component of a functionally active moiety). Non-limiting examples of polypeptides include enzymes, receptors, and antibodies. As used herein, the term "antibody" includes polyclonal antibodies, monoclonal antibodies, humanized or chimeric antibodies, single chain antibodies, Fab fragments, and $F(ab)_2$ fragments. Polyclonal antibodies are heterogeneous populations of antibody molecules that are contained in the sera of immunized animals. Monoclonal antibodies, which are homogeneous populations of antibodies with affinity for a particular epitope of an antigen, can be prepared using standard methodology. In particular, monoclonal antibodies can be obtained by any technique that provides for the production of antibody molecules by continuous cell lines in culture such as described by Kohler et al. (Nature, 256:495 (1975)); the human B-cell hybridoma technique (Kosbor et al., Immunology Today, 4:72 (1983) and Cole et al., Proc. Natl. Acad. Sci. USA, 80:2026 (1983)); and the EBV-hybridoma technique (Cole et al., "Monoclonal Antibodies and Cancer Therapy," Alan R. Liss, Inc., pp. 77–96 (1983)). Such antibodies can be of any immunoglobulin class including IgG, IgM, IgE, IgA, IgD, and subclasses thereof. A hybridoma producing the monoclonal antibodies can be cultivated in vitro or in vivo. As those of skill in the art will understand, the immobilization of proteins has been linked to the loss of secondary structure, and thus the overall activity in non-aqueous environments; it is believed that the present invention provides a pathway to enable a sensor using protein probes that have sufficient activity of the immobilized proteins. Applications involving such polypeptide probes (e.g., antibodies) can be used, for example, as biosensors in diagnostic assays, as well as separation media for bioseparations (e.g. affinity chromatography).

A chimeric antibody is a molecule in which different portions are derived from different animal species, such as those having a variable region derived from a murine monoclonal antibody and a human immunoglobulin constant region. Chimeric antibodies can be produced through standard techniques.

Single chain antibodies are formed by linking the heavy and light chain fragments of the Fv region via an amino acid bridge, resulting in a single chain polypeptide. Single chain antibodies can be produced using standard techniques as described, for example, in U.S. Pat. No. 4,946,778.

Antibody fragments can be generated using known techniques. For example, such fragments include $F(ab')_2$ fragments that can be produced by pepsin digestion of the antibody molecule, and Fab fragments that can be generated by reducing the disulfide bridges of $F(ab')_2$ fragments. Alternatively, Fab expression libraries can be constructed as described, for example, in Huse et al., Science, 246:1275 (1989).

The probe can also be a cell. The cells can be naturally occurring or modified cells. In some embodiments, the cells can be genetically modified to express surface proteins (e.g., surface antigens) having known epitopes or having an affinity for a particular biological molecule of interest. Examples of useful cells include blood cells, liver cells, somatic cells, neurons, and stem cells. Other biological polymers can include carbohydrates, cholesterol, lipids, etc.

While biological molecules can be useful as probes in many applications, the probe itself can be a non-biological molecule. In one case, the dye probe can be used for selective biomolecule recognition, as generally described herein. Non-biological probes can also include small organic molecules that mimic the structure of biological ligands, drug candidates, catalysts, metal ions, lipid molecules, etc. Also, dyes, markers or other indicating agents can be employed as probes in the present invention in order to enable an alternative detection pathway. A combination of dyes can also be used. Dyes can also be used, in another case, as a substrate "tag" to encode a particular substrate or a particular region on a substrate, for post-processing identification of the substrate (polymer probe or target).

Substrates

A substrate is generally a material having a defined surface (e.g., rigid or semi-rigid surface). In many embodiments, at least one surface of the substrate will be substantially flat, although in other embodiments small beads, pellets, porous, etched substrates or irregular objects may provide the surface. The substrate may be organic or inorganic. Examples of suitable substrates include, in addition to those previously referenced herein, glass (e.g., silica glass), quartz, fiber optic threads, silicon (including silicon dioxide), inorganic and organic microspheres, plastic and polymer-coated substrates. The substrate may also take any desired size or shape, such as a square or round flat chip or a sphere. The substrate may also be a composite material or a multi-layer material with one or more materials presented at the surface.

As is generally known in the art, the surface of the substrate will contain functional groups (e.g., such as hydroxyl groups). The density of these functional groups is a function of the type of substrate material and any treatment steps applied to that substrate. For example, using known techniques, such as acid treatment (e.g., using a commercial product called Nochromix (Godax Laboratories)), the surface can be cleaned and left in a hydrophilic state. Polymer substrates may have functional groups intrinsic to the polymer or may have surface functional groups introduced by chemical treatment, corona discharge, plasma treatment, etc. Those of skill in the art may also use established methods for determining the density of the functional groups on the surface of substrates, such as titration, ellipsometry, X-ray photoelectron spectroscopy, fluorescent labeling, surface energy and contact angle measurements, and the like. Determining the concentration of functional groups per unit area on the surface of the substrate to be modified with the polymer chains discussed herein may be important to determining the grafting density of the polymer chains, as discussed herein. In many cases, knowledge of the surface being used will allow those of skill in the art to estimate or assume the number of functional groups per unit area, thereby providing a reasonable estimate of the amount of reagents to use in order to obtain a desired chain density per unit area. For example, an excess of reagent may be used when it is desired to attach polymer chains to all available surface functionalities. Substrates that do not contain accessible functional groups can also be used in the sensors of this invention, provided that they are first coated with a coating that provides such functional groups (as discussed elsewhere herein).

Sensors

The sensors of the present invention (i.e., the polymer brush with a probe attached) can also be utilized in a multi-step or "sandwich" assay format, wherein a number of biomolecule targets can be applied or analyzed in sequential fashion. This approach may be useful to immobilize a protein probe for the desired biomolecule target. It may also be applied as a form of signal enhancement if the secondary, tertiary, etc. biomolecules serve to increase the number of signal reporter molecules (i.e., fluorophores). For example, an attached probe may bind a protein target A through affinity binding or covalent attachment. Some portion of protein A then acts as a probe to immobilize protein target B through affinity binding or covalent attachment. Some portion of protein B then acts as a probe to immobilize protein target C through affinity binding, and so on. A similar assay may be performed using duplex and triplex DNA, RNA, PNA and/or some combination thereof.

The sensors can be used to analyze biological samples such as blood, plasma, urine, saliva, tears, mucuous derivatives, semen, stool samples, tissue samples, tissue swabs and combinations thereof. For example, where the probes are nucleic acids, the resulting sensor can be used to monitor expression levels of genes or to identify mutations or polymorphisms, or to detect the genetic material related to a disease state. In either case, target nucleic acids (i.e., free nucleic acid molecules) typically are labeled and hybridized to the tethered nucleic acid probes. For example, the target nucleic acid molecules can be fluorescently labeled and hybridized with the tethered probes under suitable conditions. Fluorescence from target nucleic acids that hybridize at discrete locations on the sensor surface can be detected by a fluorescence reader (e.g., such as a laser scanning device, a CCD camera, a confocal scanning device or plate reader, etc.). Hybridization of target nucleic acids that are labeled with a radioisotope can be detected by phosphor-imaging. Alternative methods of detection include electronic signal detection in which positive hybridization events are detected by electron transfer reactions (e.g., as described in U.S. Pat. No. 5,824,473), by the use of mass spectrometry (e.g., as described in U.S. Pat. No. 5,872,003), by electrical charge, or by magnetic detection techniques, among others.

Hybridization conditions can be tailored for particular applications. For example, hybridization conditions may differ based on length or base composition of the probes and target nucleic acids. Standard blocking agents such as Denhardt's reagent and sheared salmon sperm DNA can be used to minimize background hybridization as described, for example, in Southern et al., *Nature Genet.*, supplement, 1999, 21:5–9 and Cheung et al., *Nature Genet.*, supplement, 1999, 21:15–19.

Sensors in which the tethered probes are polypeptides can be used, for example, to screen or characterize populations of antibodies having specific binding affinity for a particular target antigen or to determine if a ligand had affinity for a particular receptor, according to procedures described generally in Leuking et al., *Anal. Biochem.*, 1991, 270(1): 103–111. Target polypeptides can be labeled, e.g., fluorescently or with an enzyme such as alkaline phosphatase, or radio labeling for easy detection.

Analyses/Measurements—Density Calculation

The present invention enables the "tailoring" of the surface of a polymer brush in order to achieved a desired number of accessible functional groups on its surface. As previously noted, one factor which must be controlled as part of the tailoring process is the grafting density of the water-soluble (or water-dispersible) segments on the substrate surface. One method for determine segment grafting density is by calculation based on the molecular weight of the polymer chains grown in solution ($M_{gpc}$) during the polymerization process (as a result of initiator being present both on the substrate surface and in the polymerization solution or system), and the polymer layer thickness, as determined by ellipsometry (t) measurements of the polymer layer on the modified substrate surface. This calculation is achieved using the following formula:

$$\text{Grafting Density} = (1 \ast 10^4 \ast t \ast \rho / M_{gpc})$$

wherein grafting density is expressed in picomoles/cm², t is expressed in Angstroms, $\rho$ is specific gravity and is expressed in grams/cm³ and molecular weight ($M_{gpc}$) is expressed in g/mole. This formula is used in Experiments 1–8, below, in order to calculate segment grafting density.

In those instances wherein no free initiator is used in the polymerization process, no polymer forms in solution. As a result, polymer brushes molecular weights cannot be measured directly. Therefore, in order to calculate the molecular weight, the polymer thickness (t) is measured from a substrate with a known density of polymer chain initiating sites (which directly correlates to the grafting density). Based on this information, the molecular weight ($M_{gpc}$, g/mole) can then be calculated using the above formula (i.e., $M_{gpc} = 1 \ast 10^4 \ast t \ast \rho / \text{grafting density}$).

Cleavable Dye Test

This method may be used to quantify the number of functional groups generally accessible to a probe or target biomolecule which are about the same size as the dye molecule being used, to optimize small molecule modification (i.e., activation), and to quantify covalently attached oligonucleotides/probes (e.g., DNA). Generally speaking, the functional groups on the polymer chain segments are quantified by attaching a dye molecule of a given size to each of the functional sites which are accessible to molecules of that size, washing the substrate to remove excess/ unbound dye, cleaving the bound dye molecules, collecting the cleaved dye molecules, and then measuring the amount of dye collected for a given surface area, using HPLC analysis with a fluorescence detector.

The amount or concentration of dye in the solution is calculated from the fluorescence signal using a calibration curve obtained from a model reaction. From this concentration data, the number of dye molecules can be determined, which then can be directly correlated to the number of functional groups on the water-soluble (or water-dispersible) segments that were accessible to molecules of a size about equal to, or less than, the size of the dye molecules employed in the test. If the surface area of the brush is known, a number of accessible functional groups per unit area may then be calculated. This test method can also be used in a similar manner to quantify the number of accessible functional groups for the probe or other molecule directly, by attaching a dye molecule to the probe that is to be attached.

Stability Test

As previously noted, the present invention enables the preparation of substrates (both planar and non-planar surfaces) having water-soluble (or water-dispersible) segments attached thereto, and optionally probes attached to these segments, which are highly stable. More specifically, the present invention enables the attachment of these segments to the substrate surface, and likewise the attachment of probes to the segments, in a manner which prevents their detachment upon exposure to subsequent processing steps. For example, in addition to the discussion provided elsewhere, it is to be noted that experience to-date has shown that biosensors prepared in accordance with the present process may be heated to a temperature above about 40° C., preferably ranging from about 40 to about 60° C., in an aqueous solution for about 16 hours (conditions commonly employed in gene expression tests) with less than about a 20% loss of probes from the segments, or segments from the substrate surface. In fact, in some cases loss may be less than about 15%, less than about 10%, or even less than about 5%. In contrast, existing sensors, such as those comprised of a glass substrate to which is attached a DNA probe by means of a silane linker, commonly experience a loss of up to about 90% of the linkers which connect the probe to the substrate surface (and therefore the probes themselves), rendering the sensor significantly less sensative.

Film Thickness Measurements

Polymer layer or film thickness may be measured as a dry thickness (i.e., in the absence of solvent) by, among other methods known to those of skill in the art, ellipsometry. (See, e.g., "A User's Guide to Ellipsometry", by Harland G. Tompkins (Academic Press, owned/published by Harcourt Brace Jovanovich, 1993), which is incorporated herein by reference.) Briefly, the thickness is determined by reflecting polarized light from the film surface and analyzing the change in the polarization state which results from the reflection. This can be related to the film thickness and index of refraction by comparing the results of the measurement with the results of a model calculation, which incorporates thickness and index as variable parameters.

Also, depending on the chain molecular weight and grafting density, as well as the solvent, the polymer chains can also be measured when in the presence of a solvent (i.e., in the "swollen" state). This "wet thickness" might be many times the dry thickness depending on the segment molecular weight, the segment persistence length, and the segment grafting density. The polymer chain conformation in solvent might be measured with neutron reflectivity or with contact methods such as by Atomic Force Microscopy ("AFM"— which provides a measure of compliance, which is similar to elasticity of the polymer on the surface; film thickness may also be measured, providing you can determine a baseline or edge within the scan), or by Surface Force Apparatus.

Applications

Once the functional group-bearing polymer chains have been grown on the substrate surface, it may be necessary to "activate" the functional groups prior to probe coupling. Various activation and coupling techniques are known in the art. These techniques may vary depending upon the particular application. Accordingly, while the following procedures are intended for illustrative purposes, those of skill in the art would be able to use these procedures, or procedures similar thereto, in order to achieve the desired results.

Carbonyldiimidazole(CDI) Activation of Hydroxyl-functionalized Polymers on Glass Slides:

Glassware used in the procedure are all oven dried at 150° C. and placed inside a dry glove box while warm. All measurements and weighings are done inside the dry box, as well. Glass slides used as substrates are dried in vacuum oven at 40° C. (24 in Hg) overnight.

In a glove box, a hydroxyl-functionalized polymer brush, bound on a glass slide, is placed in a 20 ml glass vial, which is then filled with a 0.5 M stock solution of carbonyldiimidazole in anhydrous acetonitrile. The vial is sealed tight and wrapped with electric tape (to ensure the seal). The vial is removed from the dry box and placed on horizontal shaker for 24 hrs. The vial is opened at the end of the 24 hr period in ambient air, and then the glass slide is washed with anhydrous Acetonitrile several times. After air drying, the slide is stored in a dry, dark place until needed.

Coupling of Amine-functionalized Oligonucleotide Probes onto CDI-activated Polymer Brush:

Printing and coupling of oligonucleotide probes onto the CDI-activated polymer brushes is achieved as follows: to begin, three different stock solutions (100, 50 and 25 μM) of a 50 mer oligonucleotide (amine functionality in 3' position and Cy3 dye in 5' position), were prepared with a total concentration of 150 mM sodium phosphate (pH=8.5). The oligonucleotides were then spotted onto the glass slide using a 1 μL pipette in varying amounts on different regions of the substrates in a array format, for purposes of comparison.

After spotting was complete, the slides were incubated in a glass chamber at room temperature for 18 hrs. A blocking solution containing 50 mM ethanolamine, 0.1 M Tris and 0.1 weight percent SDS (pH=9) was then prepared. The modified slides were washed with the blocking solution at room temperature for 1 hr. and subsequently rinsed with water and air dried.

Activation of Carboxylate-functionalized Polymers and Coupling of Amine-functionalized Oligonucleotide Probes:

A carboxylate-functionalized (COOH) polymer can be activated, and amine-functionalized probes can be coupled, via the commonly-known technique of carbodiimide activation. For example, using EDC [1-ethyl-3-(3-dimethylaminopropylcarbodiimide], an amine-functionalized probe can be coupled to the activated polymer by a single-step condensation via the amine-reactive intermediate, O-acylisourea. This intermediate is unstable in aqueous solution and must be immediately reacted with the amine-functionalized probe. (see, e.g., Williams & Ibrahim, JACS, 103, 1981, p. 7090–7095.)

Alternatively, the amine-terminated probe can be coupled in two steps by using EDC and NHS [N-hydroxysuccinimide]. In this method, the polymer functional sites retain a stable, amine-reactive NHS ester functionality in the presence of water, which can later be coupled with the amine-functionalized probe. (see, e.g., Grabaraek & Gergely, Anal. Biochem., 185, 1990, p. 131–135.)

General Technique for Hybridization and Scanning Oligonucleotide (and cDNA) Arrays:

Once the polymer brush has been successfully activated and the probes attached, the resulting "biosensor" may be used in scanning procedures common in the art (see, e.g., Lockhart et al., Nature Biotechnology (14), 1996, pp. 1675-). A scanning procedure such as the following may also be used.

The above-referenced probe-activated brushes were immerse in either (i) a 4×SSC target solution (i.e., a solution comprising 30 mM sodium chloride, 3 mM sodium citrate and 0.1% SDS; pH 8.0), or (ii) a 6×SSPE target solution (i.e., a solution comprising 0.9 M sodium chloride, 60 mM $NaH_2PO_4$, 6 mM EDTA and 0.005% Triton X-100; pH 7.6), both of which additionally contained RNA or DNA target molecules. In one embodiment, the hybridization can be performed by exposing the whole slide to the target solution, in this case by immersing or otherwise placing about 24 to 100 L of the target solution on the array under a 22 mm×22 mm glass cover slip (used in order to limit the amount of solution which evaporates during the process). Hybridization may also be achieved by exposing the array to a much larger amount of the target solution (e.g., about 500 microliters to about 500 milliliters of solution, but this typically requires some form of flow cell, and/or agitation of the bulk solution).

Hybridization was then achieved by heating each of the probe-attached brushes at about 40 to about 65° C. for a period of time (ranging from about 4 to about 24 hrs, depending on target molecule being studied). If a biotinylated target molecule is used, the hybridized brush is additionally incubated with 2 μg/ml fluorescenated streptavidin or streptavidin-phycoerythrin (SAPE) in the hybridization buffer at about 40° C. for 5–10 min.

To scan the resulting hybridized brushes in solution, they are first rinsed or gently agitated with fresh hybridization buffer for about 5–10 minutes, and then they are scanned for surface fluorescence using a confocal microarray scanner (such as, for example, a Hewlett Packard GeneArray scanner).

To scan the resulting hybridized brushes dry, they are first rinsed or agitated in a solution comprising a 1×SSC solution (i.e., the above-referenced 4×SSC solution being dilutioned by a factor of 4), the cover slip being removed if necessary, after which the brushes are removed and blotted dry. The rinse step is repeated twice, each time using a more dilute solution (i.e., the above 1×SSC solution first being diluted by a factor of 5, and then a factor of 20). The brushes are then spun dry by centrifugation in a slide rack (Beckman GS-6 tabletop centrifuge at 600 RPM for 2 mins.), after which the brushes are scanned for surface fluorescence using a microarray scanner (such as, for example, an AXON GenePix or GSI Lumonics ScanArray scanner).

Advantageously, the brushes may be used to accurately call in excess of 90%, 95%, 97%, 98%, or 99% of the targets in an analyte-containing solution.

Definitions

As used herein, the phrase "characterized by the formula" is not intended to be limiting and is used in the same way that "comprising" is commonly used. The term "independently selected" is used herein to indicate that the R groups, e.g., $R^1$, $R^2$, $R^3$, etc., can be identical or different (e.g. $R^1$, $R^2$ and $R^3$ may all be substituted alkyls or $R^1$ and $R^2$ may be a substituted alkyl and $R^3$ may be an aryl, etc.). A named R group will generally have the structure that is recognized in the art as corresponding to R groups having that name. For the purposes of illustration, representative R groups as enumerated above are defined herein. These definitions are intended to supplement and illustrate, not preclude, the definitions known to those of skill in the art.

The term "alkyl" is used herein to typically refer to a branched or unbranched, saturated acyclic hydrocarbon radical. Suitable alkyl radicals include, for example, methyl, ethyl, n-propyl, i-propyl, n-butyl, t-butyl, i-butyl (or 2-methylpropyl), etc. In particular embodiments, alkyls have between 1 and 200 carbon atoms, between 1 and 50 carbon atoms, or between 1 and 20 carbon atoms.

The term "alkenyl" is used herein to typically refer to a branched or unbranched acyclic hydrocarbon radical having at least one carbon-carbon double bond. Exemplary alkenyl radicals include, for example, 2-propenyl (or allyl), vinyl, etc. In particular embodiments, alkenyls have between 1 and 200 carbon atoms, between about 1 and 50 carbon atoms, or between about 1 and 20 carbon atoms. In addition, this term embraces radicals having both "cis" and "trans" orientations, or alternatively, "E" and "Z" orientations.

The term "akynyl" is used herein to typically refer to a branched or unbranched acyclic hydrocarbon radical having at least one carbon-carbon triple bond. In particular embodiments, alkynyls have between 1 and 200 carbon atoms, between about 1 and 50 carbon atoms, or between about 1 and 20 carbon atoms.

"Substituted alkyl," "substituted alkenyl" and "substituted alkynyl" typically refer to the alkyl, alkenyl and alkynyl radicals, respectively, as just described in which one or more hydrogen atoms to any carbon of these radicals is replaced by another group such as a heteroatom, halogen, aryl, substituted aryl, cycloalkyl, cycloalkenyl, substituted cycloalkyl, substituted cycloalkenyl and combinations thereof. Exemplary substituted alkyls include, for example, benzyl, trifluoromethyl and the like.

The term "heteroalkyl," "heteroalkenyl" and "heteroalkynyl" typically refer to the alkyl, alkenyl and alkynyl radicals, respectively, described above in which one or more of the carbon chain atoms of these radicals is replaced by a heteroatom selected from the group consisting of N, O, P, B, S, Si, Se and Ge. The bond between the carbon atom and the heteroatom may be saturated or unsaturated. Thus, an alkyl substituted with a heterocycloalkyl, substituted heterocycloalkyl, heteroaryl, substituted heteroaryl, alkoxy, aryloxy, boryl, phosphino, amino, silyl, thio, or seleno is within the scope of the term heteroalkyl. Suitable heteroalkyls include cyano, benzoyl, 2-pyridyl, 2-furyl, $Me_3SiOCH_2(CH_3)_2C-$ and the like.

The term "cycloalkyl" is used herein to typically refer to a saturated cyclic non-aromatic hydrocarbon radical having a single ring or multiple condensed rings. Exemplary cycloalkyl radicals include, for example, cyclopentyl, cyclohexyl, cyclooctanyl, bicyclooctyl, etc. In particular embodiments, cycloalkyls have between 3 and 200 carbon atoms, between 3 and 50 carbon atoms or between 3 and 20 carbon atoms.

The term "cycloalkenyl" is used herein to typically refer to a partially unsaturated (i.e., having at least one carbon-carbon double bond), cyclic non-aromatic hydrocarbon radical having a single ring or multiple condensed rings. Exemplary cycloalkenyl radicals include, for example, cyclopentenyl, cyclohexenyl, cyclooctenyl, etc. In particular embodiments, cycloalkyls have between 3 and 200 carbon atoms, between 3 and 50 carbon atoms or between 3 and 20 carbon atoms.

"Substituted cycloalkyl" and "substituted cycloalkenyl" typically refer to cycloalkyl and cycloalkenyl radicals, respectively, as just described wherein one or more hydrogen atoms to any carbon of these radicals is replaced by another group such as a halogen, alkyl, alkenyl, alkynyl, substituted alkyl, substituted alkenyl, substituted alkynyl, aryl, substituted aryl, cycloalkyl, cycloalkenyl, substituted cycloalkyl, substituted cycloalkenyl, heterocyclo, substituted heterocyclo, heteroaryl, substituted heteroaryl, alkoxy, aryloxy, boryl, phosphino, amino, silyl, thio, seleno and combinations thereof. Exemplary substituted cycloalkyl and cycloalkenyl radicals include, for example, 4-dimethylaminocyclohexyl, 4,5-dibromocyclohept-4-enyl, and the like.

The term "aryl" is used herein to typically refer to an aromatic substituent that may be a single aromatic ring or multiple aromatic rings which are fused together, linked covalently, or linked to a common group such as a methylene or ethylene moiety. The common linking group may also be a carbonyl as in benzophenone or oxygen as in diphenylether or nitrogen in diphenylamine. The aromatic ring(s) may include phenyl, naphthyl, biphenyl, diphenylether, diphenylamine and benzophenone among others. In particular embodiments, aryls have between 1 and 200 carbon atoms, between 1 and 50 carbon atoms or between 1 and 20 carbon atoms.

"Substituted aryl" typically refers to aryl as just described in which one or more hydrogen atom to any carbon is replaced by one or more functional groups such as alkyl, alkenyl, alkynyl, substituted alkyl, substituted alkenyl, substituted alkynyl, cycloalkyl, cycloalkenyl, substituted cycloalkyl, substituted cylcoalkenyl, heterocyclo, substituted heterocyclo, halogen, alkylhalos (e.g., $CF_3$), hydroxy, amino, phosphino, alkoxy, thio and both saturated and unsaturated cyclic hydrocarbons which are fused to the aromatic ring(s), linked covalently or linked to a common group such as a methylene or ethylene moiety. The linking group may also be a carbonyl such as in cyclohexyl phenyl ketone. Specific examples of substituted aryls include perfluorophenyl, chlorophenyl, 3,5-dimethylphenyl, 2,6-diisopropylphenyl and the like.

The term "heterocyclo" is used herein to typically refer to saturated, partially unsaturated and unsaturated cyclic radicals (including, for example, cycloalkyl and cycloalkenyl radicals as described), wherein one or more or all carbon atoms of the radical are replaced by a heteroatom such as nitrogen, phosphorus, oxygen, sulfur, silicon, germanium, selenium, or boron. Additionally, the term "heteroaryl" as used herein typically refers to a specific example of a class of unsaturated cyclic radicals wherein one or more carbon atoms of an aromatic ring or rings are replaced by a heteroatom(s) such as nitrogen, oxygen, boron, selenium, phosporus, silicon or sulfur. Heteroaryl typically refers to structures that may be a single aromatic ring, multiple aromatic ring(s), or one or more aromatic rings coupled to one or more nonaromatic ring(s). In structures having multiple rings, the rings can be fused together, linked covalently, or linked to a common group such as a methylene or ethylene moiety. The common linking group may also be a carbonyl as in phenyl pyridyl ketone. As used herein, rings such as thiophene, pyridine, isoxazole, phthalimide, pyrazole, indole, furan, etc. or benzo-fused analogues of these rings are defined by the term "heteroaryl."Other exemplary heterocyclo radicals include, for example, piperazinyl, morpholinyl, tetrahydropyranyl, tetrahydrofuranyl, piperidinyl, pyrrolidinyl, oxazolinyl, and the like.

"Substituted heterocyclo" and "substituted heteroaryl" typically refer to heterocyclo and/or heteroaryl radicals as just described wherein one or more hydrogen atom to any atom of the radical is replaced by another group such as a halogen, alkyl, substituted alkyl, aryl, substituted aryl, heteroaryl, substituted heteroaryl, alkoxy, aryloxy, boryl, phosphino, amino, silyl, thio, seleno and combinations thereof. Exemplary substituted heteroaryl radicals include, for example, 4-N,N-dimethylaminopyridine. Other exemplary substituted heterocyclo radicals include, for example, N-methylpiperazinyl, 3-dimethylaminomorpholine, and the like.

"Hydrocarbyl" typically refers to univalent hydrocarbyl radicals containing 1 to about 30 carbon atoms, preferably 1 to about 24 carbon atoms, most preferably 1 to about 12 carbon atoms, including branched or unbranched, saturated or unsaturated species, such as alkyl groups, alkenyl groups, aryl groups, and the like. The term "lower hydrocarbyl" intends a hydrocarbyl group of one to six carbon atoms, preferably one to four carbon atoms. The term "hydrocarbylene" typically intends a divalent hydrocarbyl moiety containing 1 to about 30 carbon atoms, preferably 1 to about 24 carbon atoms, most preferably 1 to about 12 carbon atoms, including branched or unbranched, saturated or unsaturated species, or the like. The term "lower hydrocarbylene" typically intends a hydrocarbylene group of one to six carbon atoms, preferably one to four carbon atoms. "Substituted hydrocarbyl" typically refers to hydrocarbyl substituted with one or more substituent groups, and the terms "heteroatom-containing hydrocarbyl" and "heterohydrocarbyl" typically refer to hydrocarbyl in which at least one carbon atom is replaced with a heteroatom. Similarly, "substituted hydrocarbylene" typically refers to hydrocarbylene substituted with one or more substituent groups, and the terms "heteroatom-containing hydrocarbylene" and "heterohydrocarbylene" typically refer to hydrocarbylene in which at least one carbon atom is replaced with a heteroatom.

The term "alkoxy" is used herein to typically refer to the —$OZ^1$ radical, where $Z^1$ is selected from the group consisting of alkyl, substituted alkyl, cycloalkyl, substituted cycloalkyl, heterocylcoalkyl, substituted heterocycloalkyl, silyl groups and combinations thereof as described herein. Suitable alkoxy radicals include, for example, methoxy, ethoxy, benzyloxy, t-butoxy, etc. A related term is "aryloxy" where $Z^1$ is selected from the group consisting of aryl, substituted aryl, heteroaryl, substituted heteroaryl, and combinations thereof. Examples of suitable aryloxy radicals include phenoxy, substituted phenoxy, 2-pyridinoxy, 8-quinalinoxy and the like.

As used herein the term "silyl" typically refers to the —$SiZ^1Z^2Z^3$ radical, where each of $Z^1$, $Z^2$, and $Z^3$ is independently selected from the group consisting of alkyl, substituted alkyl, cycloalkyl, heterocycloalkyl, heterocyclic, aryl, substituted aryl, heteroaryl, substituted heteroaryl, alkoxy, aryloxy, amino, silyl and combinations thereof.

As used herein the term "boryl" typically refers to the —$BZ^1Z^2$ group, where each of $Z^1$ and $Z^2$ is independently selected from the group consisting of alkyl, substituted alkyl, cycloalkyl, heterocycloalkyl, heterocyclic, aryl, substituted aryl, heteroaryl, substituted heteroaryl, alkoxy, aryloxy, amino, silyl and combinations thereof.

As used herein, the term "phosphino" typically refers to the group —$PZ''$, where each of $Z''$ is independently selected from the group consisting of hydrogen, oxygen, substituted or unsubstituted alkyl, cycloalkyl, heterocycloalkyl, heterocyclic, aryl, heteroaryl, silyl, alkoxy, aryloxy, amino and combinations thereof, where n is z to 4 depending on the phosphorus oxidation state.

The term "amino" is used herein to typically refer to the group —$NZ^1Z^2$, where each of $Z^1$ and $Z^2$ is independently selected from the group consisting of hydrogen, alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, silyl and combinations thereof.

The term "thio" is used herein to typically refer to the group —$SZ^1$, where $Z^1$ is selected from the group consisting of hydrogen, alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, silyl and combinations thereof.

The term "seleno" is used herein to typically refer to the group —$SeZ^1$, where $Z^1$ is selected from the group consisting of hydrogen, alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, silyl and combinations thereof.

The term "saturated" typically refers to lack of double and triple bonds between atoms of a radical group such as ethyl, cyclohexyl, pyrrolidinyl, and the like.

The term "unsaturated" typically refers to the presence one or more double or triple bonds between atoms of a radical group such as vinyl, acetylenyl, oxazolinyl, cyclohexenyl, acetyl and the like.

The phrase "living-type kinetics" typically refers to a polymerization where substantially all chains are reactive and propagating throughout the course of the polymerization reaction, and where a plot of chain length versus conversion is approximately linear.

The phrase "water-soluble" when used in connection with a polymer chain or a polymer chain segment which is soluble in an aqueous solution under some conditions (including, for example, aqueous solutions at a selected pH or in the presence of one or more selected buffers, etc.). Additionally, the phrase "water-dispersible" typically refers to a polymer chain which includes some entity which is not solvated by water.

The term "radius of gyration" or "Rg" typically refers to one-half the mean square end-to-end distance of a linear chain molecule in solution.

It is to be noted that, as used herein, "terminus" generally refers the end regions of a polymer chain, within which various polymer architectures may be present (e.g., linear chains, branched chains, etc.); that is, it is to be understood that, as used herein, "terminus" does not necessarily refer to the last atom at each end of the principal polymer chain. However, it is also to be understood that this term is used in the context of the polymer backbone, and therefore is not intended to include or refer to the end of a short chain branch or of a substituent group attached to the polymer backbone.

It is to be still further noted that, as used herein, the term "layer" typically refers to a region on the substrate surface that comprises hydrophobic or water-soluble/water-dispersible polymer chain segments and, as a result, has a corresponding surface characteristic. Accordingly, it is to be understood that the hydrophobic layer or water-soluble/water-dispersible layer may not continuously extend over the entire substrate surface. More specifically, once formed, the hydrophobic layer may extend over discrete regions of the substrate surface, or it may be a single region extending over a portion (e.g., about 25%, 50%, 75%, 85%, 95% or more) or substantially all of the substrate surface. Likewise, once formed, the water-soluble/water-dispersible layer may extend over discrete regions of the hydrophobic layer, or it may be a single region extending over a portion (e.g., about 25%, 50%, 75%, 85%, 95% or more) or substantially all of the hydrophobic layer.

The sensors of the present invention provide increased sensitivity of measurements as well as lower signal to noise ratios, as compared to known surface bound sensors. The invention will now be described and illustrated further by way of the following examples. These examples are therefore not to be viewed in a limiting sense.

EXAMPLES

Examples 1 through 19 illustrate various features with respect to the preparation and use of polymer brushes that are relevant to the present invention, while Examples 20 through 25 further illustrate certain features of the present invention.

Example 1

The following example illustrates one approach for the preparation of a monomer suitable for use in the present invention for polymer brush preparation.

I. Synthesis of N-Methyl,N-(2-hydroxyethyl)acrylamide:
A. Synthesis of N-Methyl,N-2-(1-Trimethylsiloxy)ethylacrylamide:

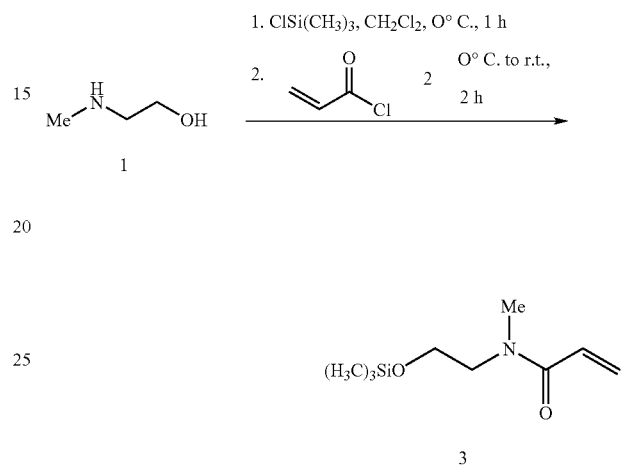

An oven-dried 4 L three-necked flask equipped with an overhead mechanical stirrer, a 250 mL dropping funnel and an adapter to an argon line was charged under an atmosphere of argon with 113 g (1.5 mol, 121 mL) 2-(methylamino)ethanol (1), commercially available from Sigma-Aldrich, 1500 mL of anhydrous dichloromethane, and 334 g (460 mL, 3.3 mol) of triethylamine. The solution was chilled to ca. 0° C. (icebath) and 171 g (1.58 mol, 200 mL) of chlorotrimethylsilane (TMSCl) were added dropwise. Upon completion of the exothermic reaction (ca. 1 h), the reaction mixture is cooled again to ca. 0° C. (icebath) and acryloyl chloride (2) (136 g, 1.5 mol, 122 mL) were added dropwise and the reaction mixture was stirred for ca. 2 h with warming to room temperature. The pH of the reaction mixture should be established at ca. 9. The reaction was quenched by careful addition of 2 L of water. After thoroughly mixing, the aqueous layer was decanted off and the procedure was repeated twice (2×1000 mL). After thoroughly mixing, the aqueous layer was separated and the solution was dried ($Na_2SO_4$) and the solvent removed under reduced pressure to yield an orange-yellow product 3 of sufficient purity (>95% by $^1H$ NMR) which can be used without further purification in the next step. In the case of triethylammonium chloride impurities the washing protocol is repeated and the crude product was freed from excess triethylamine in high vacuo. $^1H$ NMR (300 MHz, $CDCl_3$, room temp., (E)/(Z)-isomers): δ 6.53 (dd, J=16.8, 2.4 Hz, 1H, CH=CHH), 6.48 (dd, J=16.5, 2.4 Hz, 1H, CH=CHH), 6.26–6.13 (2dd, superimposed, 2×1H, CH=CHH), 5.62–5.46 (2×dd, superimposed, 2×1H, CH=CHH), 3.60 (t, J=6.3 Hz, 2H, $CH_2CH_2O$), 3.55 (t, J=6.3 Hz, 2H, $CH_2CH_2O$), 3.40 (t, J=6.3 Hz, 2H, $CH_2CH_2O$), 3.35 (t, J=6.3 Hz, 2H, $CH_2CH_2O$), 3.03 (s, 3H, $NCH_3$), 2.91 (s, 3H, $NCH_3$), −0.01 (2s, superimposed, 2×9H, $Si(CH_3)_3$), both diastereoisomers) ppm.

B. Synthesis of N-Methyl,N-2-(1-hydroxy)ethylacrylamide:

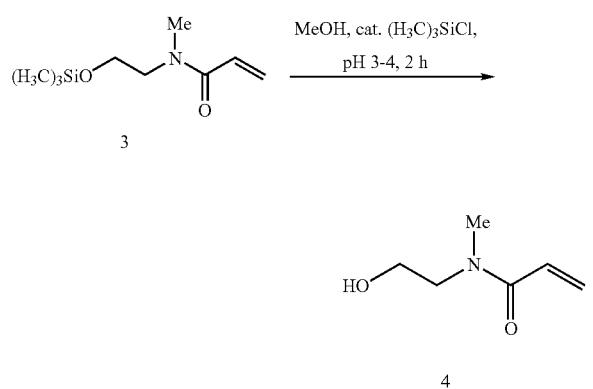

An oven-dried 3 L round-bottomed flask equipped with a magnetic stir and an adapter to an argon line was charged under an atmosphere of argon with the crude product 3 obtained in step B and dissolved in 1.5 L of anhydrous methanol. Chlorotrimethylsilane was added dropwise the reaction mixture till the pH reached 3–4 (ca. 10 mL). The reaction mixture turns from orange to yellowish upon cleavage. Upon completion of the reaction, the solvent was removed under reduced pressure to yield 169 g (87%) of 4 as an orange crude product of sufficient purity which can be used without further purification in the following polymerization step. $R_f$: 0.25 (EtOAc/MeOH=40:1). $^1$H NMR (300 MHz, DMSO-d$^6$, room temp., (E)/(Z)-isomers): δ 6.76 (dd, J=16.5, 10.2 Hz, 1H, C(=O)CH=CHH), δ 6.73 (dd, J=16.5, 10.8 Hz, 1H, C(=O)CH=CHH), 6.08 (dd, J=16.8, 2.7 Hz, 1H, C(=O)CH=CHH), 6.06 (dd, J=16.5, 2.4 Hz, 1H, C(=O)CH=CHH), 5.65 (dd, J=10.5, 2.7 Hz, 1H, C(=O)CH=CHH), 5.60 (dd, J=10.5, 2.4 Hz, 1H, C(=O)CH=CHH), 4.80 (t, J=5.1 Hz, 1H, OH), 4.67 (t, J=5.4 Hz, 1H, OH), 3.53–3.45 (m, 2H, CH$_2$CH$_2$OH, both diastereoisomers), 3.45–3.37 (m, 2×2H, CH$_2$CH$_2$OH, both diastereoisomers), 3.06 (s, 3H, NCH$_3$), 2.88 (s, 3H, NCH$_3$) ppm.

C. N-Dansylcystamine (10):

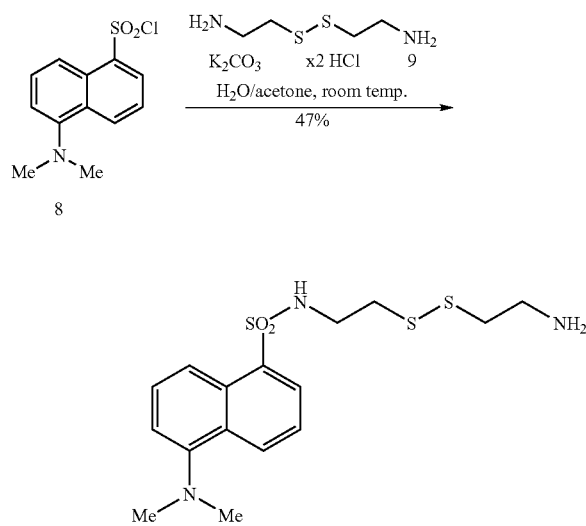

A 250 mL round-bottomed flask equipped with a magnetic bar and a 100 mL addition funnel was charged with cystamine dihydrochloride (9) (4.95 g, 22 mmol), K$_2$CO$_3$ (7.28 g, 52.8 mmol) and 50 mL of deionized water. Dansyl chloride (8) (1.00 g, 3.7 mmol) was dissolved in 20 mL of acetone and was added dropwise to the aqueous solution by means of the addition funnel. The reaction mixture turned from slight orange to yellow-green in two hours. Upon completion of the reaction, acetone was removed under reduced pressure. The reaction mixture was extracted with ethyl acetate (2×100 mL). The organic extracts were combined and washed with brine and dried over MgSO$_4$. After filtration and evaporation, the crude product was further purified by MPLC (silica gel, EtOAc/MeOH=2:1) to yield 670 mg (47%) of a yellow-green solid. $R_f$: 0.48 (EtOAc/MeOH=1:1, stained with 2% ninhydrin). $^1$H NMR (300 MHz, CDCl$_3$, room temp.): δ 8.51 (d, J=8.7 Hz, 1H, Ar—H), 8.25 (dd, J=8.7 Hz, 2H, Ar—H), 7.57–7.47 (m, 2H, Ar—H), 7.16 (d, J=7.5 Hz, 1H, Ar—H), 3.22 (t, J=6.3 Hz, 2H, CH$_2$CH$_2$NHSO$_2$), 2.86 (s, 8H, NCH$_3$, CH$_2$CH$_2$NH$_2$), 2.62 (t, J=6.3 Hz, CH$_2$SSC H$_2$), 2.57 (t, J=6.3 Hz, CH$_2$SSC H$_2$) ppm.

General Procedures:

Examples 2–14 Using "Free" Initiator/Initiator-Control Adduct

Surface modifications were carried out on 2×3 and 1×3 inch fused silica glass wafers and 1 inch round silicon wafers. The wafers were cleaned with acetone and dichloromethane prior to use. The initiator-control agent adducts were tethered to the wafer surface via a short alkyl spacer (five carbon atoms) using silane chemistry following the procedure described in Husseman et al., *Macromolecules* 1999, 32, 1424–31. The corresponding chloromethyl adduct was treated with 1-pentenol using sodium hydride in dimethylformamide (DMF). Subsequent hydrosilylation with trichlorosilane/chloroplatinic acid in 1:1 ethanol/dimethoxyethane yielded the surface-active initiator-control agent adduct.

Treatment of this initiating moiety with the surface silanol groups of the fused silica and/or silicon wafers was catalyzed by triethylamine in toluene to provide covalently modified initiating substrate surfaces (i.e., derivatized surfaces). In each of the below examples (i.e., examples 1–8), the total amount of trichlorosilyl-substituted initator-control agent adduct (and dummy molecules where applicable) was 5×10$^{-4}$ mol per 2×3 inch wafer. Depending on the desired chain surface grafting density on the surface, the ratio of linker-modified initiator-control agent adduct to dummy molecule was adjusted. The surface bound initiator-control agent adduct was either

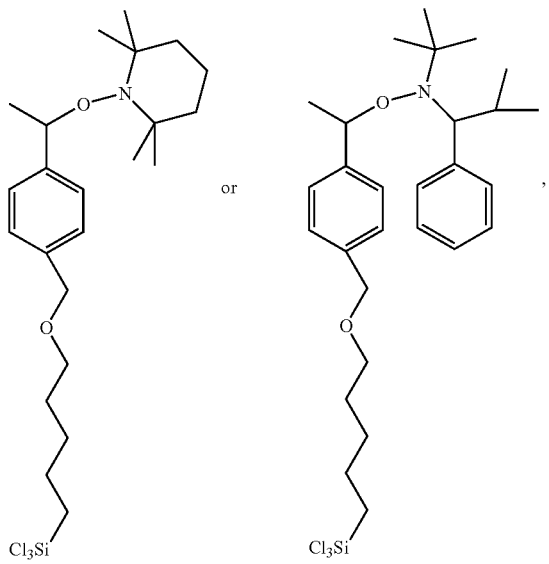

with the Si attached to the surface, as is known. The unbound initiator-control agent in all the examples was Also in each example, free radical nitroxyl was added, which had the composition

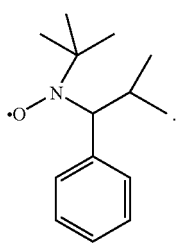

The inactive "dummy" molecule was which was synthesized following the same procedure, but starting from benzylchloride.

The surface grafted initiator-control agent adducts were used to form surface-bound polymers as follows. All polymerizations were carried out in a 500 mL sealable vessel with an argon inlet. The total volume of the polymerization reaction mixture was 350 mL. This volume ensured that the wafers were fully covered by the polymerization mixture. Three to six initiator-control agent modified wafers were positioned upright in the reaction vessel leaning against a central Teflon core at a 45° angle. The positioning of the wafer was designed to allow the site to be modified to be fully exposed to the reactants. A small silicon wafer was added to serve as a probe for thickness measurements. The initiator to monomer ratio was controlled by the amount of unbound initiator-control agent adduct in the polymerization reaction mixture. 2–5 mol % of free α-hydrido-nitroxide relative to non-surface-attached initiator-control agent adduct was added in order to control the propagation of monomer, as well as to substitute the TEMPO radical when TEMPO-containing surface-bound adduct was used.

The polymerizations were carried out in bulk or in 50 to 90 weight percent aqueous solutions. The water-soluble monomers were N,N-dimethylacrylamide and N-methyl-N-(2-hydroxyethyl)acrylamide; the latter provided hydroxyl functionality. The monomers were degassed by subjecting them to three freeze-pump-thaw cycles prior to use.

Size Exclusion Chromatography was performed using an automated "Accelerated GPC" system as described in U.S. patent application Ser. Nos. 09/285,363; 09/285,333; 09/285,335; or 09/285,392; each of which was filed on Apr. 2, 1999 and each of which is incorporated herein by reference. In the current apparatus, dimethylformamide containing 0.1% of trifluoroacetic acid at a flow rate of 2 ml/min. and a series of three 30 cm×7.5 mm linear columns calibrated using narrow polystyrene standards. The concentration of the polymer in the eluent was monitored using an evaporative light scattering detector. All of the molecular weight results obtained are relative to linear polystyrene standards. Thickness of the polymers was determined by ellipsometry measurements on the substrate surface. Thickness measurements were made using a Gaertner L 116A rotating analyzer ellipsometer, which uses a HeNe laser ($\delta$=632.8 nm) and an incidence angle of 70°.

Example 2

This example describes the preparation of a surface-bound copolymer having a target molecular weight of 50,000 daltons and 10 mol % of N-methyl-N-(2-hydroxyethyl)-acrylamide and 90 mol % N,N-dimethylacrylamide. Three fused silica wafers and one silicon wafer were used in this experiment. It was assumed that each surface contained hydroxyl functionalities typically in the picomole per square inch range. In order to add an initiator-control agent adduct to each surface hydroxyl functionality, $5 \times 10^{-4}$ mol of the trichlorosilyl-substituted initiator-control agent adduct was used per 2×3 in. wafer. Thus, the surface in this example is considered to have a fraction of chain initiator to the total number of reactive sites on the substrate surface of about 1.

Unbound initiator-control agent adduct (1.9 g) was dissolved in 291 mL of N,N-dimethylacrylamide, 37.9 g of N-methyl-N-(2-hydroxyethyl)acrylamide, 32 mg of α-hydridonitroxide, and 30 mL of water. The reaction vessel was sealed under argon and heated at 130° C. for 48 h. After the polymerization reaction, the wafers were placed in a DMF bath and heated at 50° C. for 12 h to remove non-covalently attached polymer chains, which were then analyzed by SEC, as described above. After washing with water and acetone, the wafers were air-dried and analyzed via ellipsometry to determine the thickness of the surface-bound copolymer film. SEC molecular weight ($M_w$, calibration versus polystyrene standards): 72,000; Film Thickness: 275 Å. Additionally, utilizing the method of determining grafting density described above (see, e.g., "Density Calculation"), the chain grafting density of the resulting polymer brush was found to be about 38 picomol/cm$^2$.

Example 3

This example describes the preparation of a surface-bound copolymer brush having a target molecular weight of 50,000 daltons and 25 mol % incorporation of N-methyl-N-(2-hydroxyethyl)acrylamide.

Substantially following Example 2, three fused silica wafers and one silicon wafer were modified with the trichlorosilyl-substituted initiator/control agent adduct to provide a fraction of chain initiator to the total number of surface functionalities of about 1. 1.9 g of unbound initiator-control agent adduct was dissolved in 232 mL of N,N-dimethylacrylamide, 90.8 g of N-methyl-N-(2-hydroxyethyl)acrylamide, 32 mg of α-hydridonitroxide, and 30 mL of water. The reaction vessel was sealed under argon and heated at 130° C. for 48 h. After the polymerization reaction, the wafers were placed in a DMF bath and heated at 50° C. for 12 h to remove non-covalently attached polymer that was then analyzed by SEC, as described above. After washing with water and acetone, the wafers were air dried and analyzed via ellipsometry to determine the thickness of the surface-bound copolymer film. SEC molecular weight (Mw, calibration versus polystyrene standards): 66,000; Film Thickness: 290 Å; and, Chain Density: ~44 picomol/cm$^2$.

Example 4

This example describes the preparation of a surface-bound copolymer having a target molecular weight of 10,000 daltons and 10 mol % incorporation of N-methyl-N-(2-hydroxyethyl)acrylamide.

Substantially following Example 2, three fused silica wafers and one silicon wafer were modified with the trichlorosilyl-substituted initiator-control agent adduct to provide a fraction of chain initiator to the total number of surface functionalities of about 1. 9.5 g of unbound initiator-control agent adduct was dissolved in 291 mL of N,N-dimethylacrylamide, 37.9 g of N-methyl-N-(2-hydroxyethyl)acrylamide, 160 mg of α-hydridonitroxide, and 30 mL of water. The reaction vessel was sealed under argon and heated at 130° C. for 48 h. After the polymerization reaction, the wafers were placed in a DMF bath and heated at 50° C. for 12 h to remove non-covalently attached polymer, which was then analyzed by SEC. After washing with water and acetone, the wafers were air dried and analyzed via ellipsometry to determine the thickness of the surface-bound copolymer film. SEC molecular weight (Mw, calibration versus polystyrene standards): 22,000; Film Thickness: 100 Å; and, Chain Density: ~46 picomol/cm$^2$.

Example 5

This example describes the preparation of a surface-bound copolymer brush having a target molecular weight of 10,000 daltons and 25 mol % incorporation of N-methyl-N-(2-hydroxyethyl)acrylamide.

Substantially following Example 2, three fused silica wafers and one silicon wafer were modified with the trichlorosilyl-substituted initiator-control agent adduct to provide a fraction of chain initiator to the total number of surface functionalities of about 1. 9.1 g of unbound initiator-control agent adduct was dissolved in 232 mL of N,N-dimethylacrylamide, 90.8 g of N-methyl-N-(2-hydroxyethyl)acrylamide, 160 mg of α-hydridonitroxide, and 30 mL of water. The reaction vessel was sealed under argon and heated at 130° C. for 48 h. After the polymerization reaction, the wafers were placed in a DMF bath and heated at 50° C. for 12 h to remove non-covalently attached polymer that was then analyzed by SEC, as described above. After washing with water and acetone, the wafers were air-dried and analyzed via ellipsometry to determine the thickness of the surface-bound copolymer film. SEC molecular weight (Mw, calibration versus polystyrene standards): 21,500; Film Thickness: 120 Å; and, Chain Density: ~56 picomol/cm$^2$.

Example 6

This example describes the preparation of a surface-bound copolymer brush having a target molecular weight of 50,000 daltons and 25 mol % incorporation of N-methyl-N-(2-hydroxyethyl)acrylamide.

Substantially following Example 2, three fused silica wafers and one silicon wafer were modified using 50 mol % of the trichlorosilyl-substituted initiator-control agent adduct and 50 mol % of the non-initiating benzylderivative (i.e., dummy molecule) to provide a fraction of chain initiator to the total number of surface functionalities of about 0.25. 1.9 g of unbound initiator-control agent adduct was dissolved in 232 mL of N,N-dimethylacrylamide, 90.8 g of N-methyl-N-(2-hydroxyethyl)acrylamide, 32 mg of α-hydridonitroxide, and 30 mL of water. The reaction vessel was sealed under argon and heated at 130° C. for 48 h. After the polymerization reaction, the wafers were placed in a DMF bath and heated at 50° C. for 12 h to remove non-covalently attached polymer that was then analyzed by SEC. After washing with water and acetone, the wafers were air dried and analyzed via ellipsometry to determine the thickness of the surface-bound copolymer film. GPC molecular weight (Mw, calibration versus polystyrene standards): 75,000; Film Thickness: 90 Å; and, Chain Density: ~12 picomol/cm$^2$.

Example 7

This example describes the preparation of a surface-bound copolymer brush having a target molecular weight of 50,000 daltons and 25 mol % incorporation of N-methyl-N-(2-hydroxyethyl)acrylamide.

Substantially following Example 2, three fused silica wafers and one silicon wafer were modified using 25 mol % of the trichlorosilyl-substituted initiator-control agent adduct and 75 mol % of the non-initiating benzyl derivative which provided a fraction of chain initiator to the total number of surface functionalities of about 0.25. 1.9 g of unbound initiator-control agent adduct was dissolved in 232 mL of N,N-dimethylacrylamide, 90.8 g of N-methyl-N-(2-hydroxyethyl)acrylamide, 32 mg of α-hydridonitroxide, and 30 mL of water. The reaction vessel was sealed under argon and heated at 130° C. for 48 h. After the polymerization reaction, the wafers were placed in a DMF bath and heated at 50° C. for 12 h to remove non-covalently attached polymer that was then analyzed by SEC. After washing with water and acetone, the wafers were air dried and analyzed via ellipsometry to determine the thickness of the surface-bound copolymer film. SEC molecular weight (Mw, calibration versus polystyrene standards): 68,000; Film Thickness: 55 Å; and, Chain Density: ~8 picomol/cm$^2$.

Example 8

This example describes the preparation of a surface-bound copolymer brush having a target molecular weight of 100,000 daltons and 25 mol % incorporation of N-methyl-N-(2-hydroxyethyl)acrylamide.

Substantially following Example 2, three fused silica wafers and one silicon wafer were modified using 50 mol % of the trichlorosilyl-substituted initiator-control agent adduct and 50 mol % of the non-initiating benzyl derivative to provide a fraction of chain initiator to the total number of surface functionalities of about 0.5. 0.95 g of unbound initiator-control agent adduct was dissolved in 291 mL of N,N-dimethylacrylamide, 37.9 g of N-methyl-N-(2-hydroxyethyl)acrylamide, 16 mg of α-hydridonitroxide, and 30 mL of water. The reaction vessel was sealed under argon and heated at 130° C. for 48 h. After the polymerization reactions, the wafers were placed in a DMF bath and heated at 50° C. for 12 h to remove non-covalently attached polymer, which was analyzed by SEC. After washing with water and acetone, the wafers were air dried and analyzed via ellipsometry to determine the thickness of the surface-bound copolymer film. SEC molecular weight (Mw, calibration versus polystyrene standards): 125,000; Film Thickness: 100 Å; and, Chain Density: ~8 picomol/cm$^2$.

Example 9

This example describes the preparation of a surface-bound copolymer brush having a target molecular weight of 100,000 daltons and 25 mol % incorporation of N-methyl-N-(2-hydroxyethyl)acrylamide.

Substantially following Example 2, three fused silica wafers and one silicon wafer were modified using 25 mol % of the trichlorosilyl-substituted initiator-control agent adduct and 75 mol % of the non-initiating benzyl derivative to provide a fraction of chain initiator to the total number of surface functionalities of about 0.25. 0.95 g of unbound initiator-control agent adduct was dissolved in 291 mL of N,N-dimethylacrylamide, 37.9 g of N-methyl-N-(2-hydroxyethyl)acrylamide, 16 mg of α-hydridonitroxide, and 30 mL of water. The reaction vessel was sealed under argon and heated at 130° C. for 48 h. After the polymerization reaction, the wafers were placed in a DMF bath and heated at 50° C. for 12 h to remove non-covalently attached polymer that was then analyzed by SEC. After washing with water and acetone, the wafers were air-dried and analyzed via ellipsometry to determine the thickness of the surface-bound copolymer film. SEC molecular weight (Mw, calibration versus polystyrene standards): 1125,000; Film Thickness: 65 Å; and, Chain Density: ~5 picomol/cm$^2$.

Example 10

This example describes the preparation of a surface-bound copolymer brush having a target molecular weight of 50,000 daltons and 25 mol % incorporation of acrylic acid.

Substantially following Example 2, three fused silica wafers and one silicon wafer were modified using 75 mol % of the trichlorosilyl-substituted initiator-control agent adduct and 25 mol % of the non-initiating benzyl derivative which provided a fraction of chain initiator to the total number of surface functionalities of about 0.75. 2.1 g of unbound initiator-control agent adduct was dissolved in 268 g of N,N-dimethylacrylamide, 50.5 g of acrylic acid, 100 mg of α-hydridonitroxide, and 50 mL of water. The reaction vessel was sealed under argon and heated at 130° C. for 48 h. After the polymerization reaction, the wafers were placed in a DMF bath and heated at 50° C. for 12 h to remove non-covalently attached polymer that was then analyzed by SEC. After washing with water and acetone, the wafers were air dried and analyzed via ellipsometry to determine the thickness of the surface-bound copolymer film. SEC molecular weight (Mw, calibration versus polystyrene standards): 76,000.

Example 11

This example describes the preparation of a surface-bound copolymer brush having a target molecular weight of 50,000 daltons and 25 mol % incorporation of acrylic acid.

Substantially following Example 2, three fused silica wafers and one silicon wafer were modified using 50 mol % of the trichlorosilyl-substituted initiator-control agent adduct and 50 mol % of the non-initiating benzyl derivative which provided a fraction of chain initiator to the total number of surface functionalities of about 0.5. 2.1 g of unbound initiator-control agent adduct was dissolved in 268 g of N,N-dimethylacrylamide, 50.5 g of acrylic acid, 100 mg of α-hydridonitroxide, and 50 mL of water. The reaction vessel was sealed under argon and heated at 130° C. for 48 h. After the polymerization reaction, the wafers were placed in a DMF bath and heated at 50° C. for 12 h to remove non-covalently attached polymer that was then analyzed by SEC. After washing with water and acetone, the wafers were air dried and analyzed via ellipsometry to determine the thickness of the surface-bound copolymer film. SEC molecular weight (Mw, calibration versus polystyrene standards): 76,000.

Example 12

This example describes the preparation of a surface-bound copolymer brush having a target molecular weight of 50,000 daltons and 25 mol % incorporation of acrylic acid.

Substantially following Example 2, three fused silica wafers and one silicon wafer were modified using 25 mol % of the trichlorosilyl-substituted initiator-control agent adduct and 75 mol % of the non-initiating benzyl derivative which provided a fraction of chain initiator to the total number of surface functionalities of about 0.25. 2.1 g of unbound initiator-control agent adduct was dissolved in 268 g of N,N-dimethylacrylamide, 50.5 g of acrylic acid, 100 mg of α-hydridonitroxide, and 50 mL of water. The reaction vessel was sealed under argon and heated at 130° C. for 48 h. After the polymerization reaction, the wafers were placed in a DMF bath and heated at 50° C. for 12 h to remove non-covalently attached polymer that was then analyzed by SEC. After washing with water and acetone, the wafers were air dried and analyzed via ellipsometry to determine the thickness of the surface-bound copolymer film. SEC molecular weight (Mw, calibration versus polystyrene standards): 76,000.

Example 13

This example describes the preparation of a surface-bound copolymer brush having a target molecular weight of 50,000 daltons and 25 mol % incorporation of acrylic acid.

Substantially following Example 2, three fused silica wafers and one silicon wafer were modified using 12.5 mol % of the trichlorosilyl-substituted initiator-control agent adduct and 87.5 mol % of the non-initiating benzyl derivative which provided a fraction of chain initiator to the total number of surface functionalities of about 0.125. 2.1 g of unbound initiator-control agent adduct was dissolved in 268 g of N,N-dimethylacrylamide, 50.5 g of acrylic acid, 100 mg of α-hydridonitroxide, and 50 mL of water. The reaction vessel was sealed under argon and heated at 130° C. for 48 h. After the polymerization reaction, the wafers were placed in a DMF bath and heated at 50° C. for 12 h to remove non-covalently attached polymer that was then analyzed by SEC. After washing with water and acetone, the wafers were air dried and analyzed via ellipsometry to determine the thickness of the surface-bound copolymer film. SEC molecular weight (Mw, calibration versus polystyrene standards): 76,000.

Example 14

This example describes the preparation of a surface-bound copolymer brush having a target molecular weight of 80,000 daltons and 25 mol % incorporation of N-methyl-N-(2-hydroxyethyl)acrylamide.

Substantially following Example 2, three fused silica wafers and one silicon wafer were modified using 75 mol % of the trichlorosilyl-substituted initiator-control agent adduct and 25 mol % of the non-initiating benzyl derivative which provided a fraction of chain initiator to the total number of surface functionalities of about 0.75. 1.9 g of unbound initiator-control agent adduct was dissolved in 232 mL of N,N-dimethylacrylamide, 90.8 g of N-methyl-N-(2-hydroxyethyl)acrylamide, 32 mg of α-hydridonitroxide, and 30 mL of water. The reaction vessel was sealed under argon and heated at 130° C. for 48 h. After the polymerization reaction, the wafers were placed in a DMF bath and heated at 50° C. for 12 h to remove non-covalently attached polymer that was then analyzed by SEC. After washing with water and acetone, the wafers were air dried and analyzed via ellipsometry to determine the thickness of the surface-bound copolymer film. SEC molecular weight (Mw, calibration versus polystyrene standards): 88,000; Film Thickness: 175 Å; and, Chain Density: ~20 picomol/cm$^2$.

After preparation of the slides was complete, each was activated with carbonyldidimidazole as generally described above (see, e.g., "CDI activation of Hydroxyl-functionalized polymers on glass slides"). These were then treated with N-Dansylcystamine, and reductively cleaved to release the dye which was titrated with the HPLC technique as generally described above (see, e.g., Cleavable Dye Test). More specifically, attachment of the cleavable dye is achieved by submerging a brush in about 500 μM of a dye solution for about 12 hours and then washing the brush with anhydrous acetonitrile until the wash does not show any fluorescence as measured by HPLC with a fluorescence detector. The slides are then dried and stored in a dark, dry place. The attached dye molecules are then cleaved off the brush by reaction with 0.5 ml of 0.1 M dithiothreitol (DTT) or other reducing agents in acetonitrile in a cleaving chamber. The cleaved dye is then collected and quantified by HPLC analysis. Separation is performed by reverse-phase chromatography using a Waters $C_{18}$ bonded reverse-phase column (150 mm×3.9 mm) with 4 μm particle size. A gradient method is run using water and acetonitrile (water/acetonitrile changing from 70/30 to 20/80 in 60 minutes), and a 5 μl injection of the cleaved solution. Fluorescence is measured with a Waters model 474 fluorescence detector using a 530 nm band-pass emission filter and 450 nm band-pass excitation filter in conjunction with a Xenon fluorescence lamp.

The density of functional groups accessible to this specific dye, N-Dansylcystamine, was $2.066 \times 10^3$ pmol/cm$^2$ (i.e., about 86% of the total number of —OH functional sites present on the surface). In terms of functional groups density, these results indicate a significant improvement over slides currently available commercially, which typically have a functional group density of about 25 pmol/cm$^2$.

Examples 15–17

Addition of Control Agent but not Initiator to Solution

Example 15

This example describes the preparation of a surface-bound copolymer brush with 25 mol % incorporation of N-methyl-N-(2-hydroxyethyl)acrylamide with control agent, but without sacrificial initiator-control agent adduct present in the reaction mixture.

Substantially following Example 2, three 1×1 cm silicon wafer were modified using 75 mol % of the trichlorosilyl-substituted initiator-control agent adduct and 25 mol % of the non-initiating benzyl derivative to provide a fraction of chain initiator to the total number of surface functionalities of about 0.75. 32 g (0.32 moles) of N,N-dimethylacrylamide, 10.3 g (0.08 moles) of N-methyl-N-(2-hydroxyethyl)acrylamide and 1.864 mg ($8.5 \times 10^{-3}$ mmoles, $2 \times 10^{-4}$ M) of α-hydridonitroxide were placed in a 100 mL flask together with the silicon wafers. The reaction vessel was sealed under argon and heated at 130° C. for a total of 20 h. After 3, 6 and 20 h, respectively one of the wafers was removed and washed with acetone for 2 h, air dried and analyzed via ellipsometry to determine the thickness of the surface-bound copolymer film. Film Thickness: 3 h: 20 Å (mol. wt. ~5236 g/mol); 6 h: 31 Å (mol. wt. ~8115 g/mol); 20 h: 46 Å (mol. wt. ~12,042 g/mol).

Example 16

This example describes the preparation of a surface-bound copolymer brush with 25 mol % incorporation of N-methyl-N-(2-hydroxyethyl)acrylamide with control agent, but without sacrificial initiator-control agent adduct present in the reaction mixture.

Substantially following Example 2, three 1×1 cm silicon wafer were modified using 75 mol % of the trichlorosilyl-substituted initiator-control agent adduct and 25 mol % of the non-initiating benzyl derivative to provide a fraction of chain initiator to the total number of surface functionalities of about 0.75. 32 g (0.32 moles) of N,N-dimethylacrylamide, 10.3 g (0.08 moles) of N-methyl-N-(2-hydroxyethyl) acrylamide and 18.64 mg ($8.5×10^{-2}$ mmoles, $2×10^{-3}$ M) of α-hydridonitroxide were placed in a 100 mL flask together with the silicon wafers. The reaction vessel was sealed under argon and heated at 130° C. for a total of 20 h. After 3, 6 and 20 h, respectively one of the wafers was removed and washed with acetone for 2 h, air dried and analyzed via ellipsometry to determine the thickness of the surface-bound copolymer film. Film Thickness: 3 h: 20 Å (mol. wt. ~5236 g/mol); 6 h: 31 Å (mol. wt. ~8115 g/mol); 20 h: 39 Å (mol. wt. ~10,209 g/mol).

Example 17

This example describes the preparation of a surface-bound copolymer brush with 25 mol % incorporation of N-methyl-N-(2-hydroxyethyl)acrylamide with control agent, but without sacrificial initiator-control agent adduct present in the reaction mixture.

Substantially following Example 2, three 1×1 cm silicon wafer were modified using 75 mol % of the trichlorosilyl-substituted initiator-control agent adduct and 25 mol % of the non-initiating benzyl derivative to provide a fraction of chain initiator to the total number of surface functionalities of about 0.75. 32 g (0.32 moles) of N,N-dimethylacrylamide, 10.3 g (0.08 moles) of N-methyl-N-(2-hydroxyethyl) acrylamide and 0.1864 mg ($8.5×10^{4}$ mmoles, $2×10^{-5}$ M) of α-hydridonitroxide were placed in a 100 mL flask together with the silicon wafers. The reaction vessel was sealed under argon and heated at 130° C. for a total of 20 h. After 3, 6 and 20 h, respectively one of the wafers was removed and washed with acetone for 2 h, air dried and analyzed via ellipsometry to determine the thickness of the surface-bound copolymer film. Film Thickness: 3 h: 16 Å (mol. wt. ~4188 g/mol); 6 h: 22 Å (mol. wt. ~5759 g/mol); 20 h: 32 Å (mol. wt. ~8377 g/mol).

Example 18

Addition of Control Agent but not Initiator to Solution

This example describes an approach similar to Examples 15–17, above, in than no free initiator is present in the polymerization mixture. However, unlike those examples, here the iniferter technique is employed in place of the nitroxide-mediated, controlled polymerization.

1—Synthesis of the Initiator:

p-(Chloromethyl)phenyltrimethoxysilane (0.4 g, 1.62 mmol) and N,N-diethyl dithiocarbamate sodium salt (0.370 mg, 2.17 mmol) were each dissolved separately in 3 mL of dry THF. The N,N-diethyl dithiocarbamate solution was added slowly to the p-(Chloromethyl)-phenyltrimethoxysilane solution via a syringe. The solution was stirred for 7 h at room temperature. A white precipitate was formed almost immediately (NaCl) and, during the reaction period, the solution became more yellow. The mixture was then filtered and the crude product was used without further purification.

2—Surface Grafting of the Initiator:

The solution of initiator (0.2–0.3 M in dry THF or dry toluene) was directly used on glass wafers as well as on silicon wafers, prepared as described above with respect to Examples 2–14. Typically each wafer is immersed one after the other in 5 ml of solution for up to about 2 to 3 days at room temperature, to allow the initiator to react with the surface silanol groups. The surfaces were covered by 2–3 mm of solution each time. Then, the wafers were washed with DMF and dried under a prepurified $N_2$ flow at room temperature.

3—Synthesis of Polymer Brushes:

Reactions were performed in a glove box with low amount of oxygen (about 1 ppm or less). Each silicon wafer was immersed in distilled dimethylacrylamide (1 ml). As indicated by the table below, various concentrations of the control agent, tetraethylthiuram disulfide (TEDS) were used in each preparation. The surfaces were then placed about 10 cm from a 365–366 nm UV lamp and irradiated for the required time at room temperature. After polymerization, the samples were immersed in 50 ml of dichloromethane overnight to remove homopolymers that may have formed in solution. Finally, the surfaces were dried under a prepurified $N_2$ flow at room temperature. The surfaces were then characterized by ellipsometry measurements.

| Control agent (TEDS) | Irradiation time | Monomer conversion in solution (%) | Polymer thickness (Angstroms) |
| --- | --- | --- | --- |
| None (*) | 5 mn | 1 | 0 |
| None | 5 mn | 1 | 41 |
| None | 50 mn | 3 | 333 |
| 0.001 M/L | 50 mn | 5.5 | 158 |
| 0.01 M/L | 780 mn | 80 | 58 |

(*): reference sample with no bound initiator

These experiments show that no polymerization occurs on the wafer, and virtually no polymer is formed in solution when no initiator is grafted on the surface. It also shows a steady increase of the polymer thickness as the irradiation time is prolonged. The addition of control agent actually slows down the growth and provides additional control.

Example 19

Performance Study

The polymer substrate can be evaluated as a biosensor based on the ability of the polymer-bound probes to capture biomolecules (e.g. target) from solution. This performance can be evaluated in terms of the overall efficiency and selectivity of target binding, e.g., by evaluating (1) the total amount of target bound, (2) the ability to detect and quantify the amount of specific target in solution, (3) the ability to detect and quantify the amount of specific target within a complex solution, (4) the ability to enhance the dynamic range through detection of very low concentrations of target, or (5) the combined ability to detect these signals above the background and noise of the system.

This example illustrates a method for testing the performance of the polymers as a substrate for oligonucleotide probe attachment and subsequent DNA target hybridization.

In this example, oligonucleotide probes of 50-bases (50 mers) were immobilized to polymer substrates of varying fractions of surface bound chain initiator to the total number of surface functionalities (the fraction ranging from 0.125 to 0.75). Probe concentrations within a 0–200 micromolar range were used to test the loading (chemical attachment) efficiency of these probes to the activated polymer substrates. Complex (gene expression) target solutions were then applied to the probe arrays, where the solution included "spiked" picomolar concentrations of particular targets to test the efficiency of capturing/sampling very low target populations within a complex hybridization solution. The results are illustrated in FIG. 7.

All of the substrates demonstrated a loading capacity that mimicked solution hybridization, suggesting that the loading is not significantly limited or slowed by surface effects or mesh-hindered diffusion. For the range of polymer densities tested, the polymer designed with 0.25 initiator fraction reproducibly demonstrated the best performance in loading capacity for the 50-base probes. This result is consistent with the ~40 Å mesh-size analysis of the polymer architecture, suggesting that the polymer substrate can be tailored to achieve an optimal loading capacity if the mesh is roughly equivalent to half the radius of gyration of the intended probes.

The same polymer (with 0.25 initiator fraction) also reproducibly demonstrated the best performance in target hybridization, presumably due to the increased probe density and solution-like binding performance. For the polymers designed with 0.25 to 0.75 initiator fraction, these substrates significantly increased the dynamic range of the hybridization performance, as shown by the ability to hybridize and recognize ("call") more of the targets present at very low concentrations. In some cases, these substrates accurately called 100% of the targets in the gene expression solution.

Example 20

This example generally describes an approach for preparing a polymer brush in accordance with one embodiment of the present invention, wherein an iniferter/UV system is employed to initiate polymerization. No free iniferter initiator is added to the monomer solution; rather, initially the iniferter is only attached to the substrate surface (as describe herein).

1—Synthesis of the Initiator (Photoiniferter):

To a 100 ml round bottom flask was introduced 5 g (20 mmol) of p-(chloromethyl)phenyltrimethoxysilane dissolved in 20 cc of dry THF. To the stirring solution was then added slowly 4.6 g of N,N-diethyldithiocarbamate sodium salt, a white sodium chloride precipitate forming almost immediately. The reaction was allowed to proceed at room temperature for 6 hours, after which the crude product was filtered. The crude product was used without further purification.

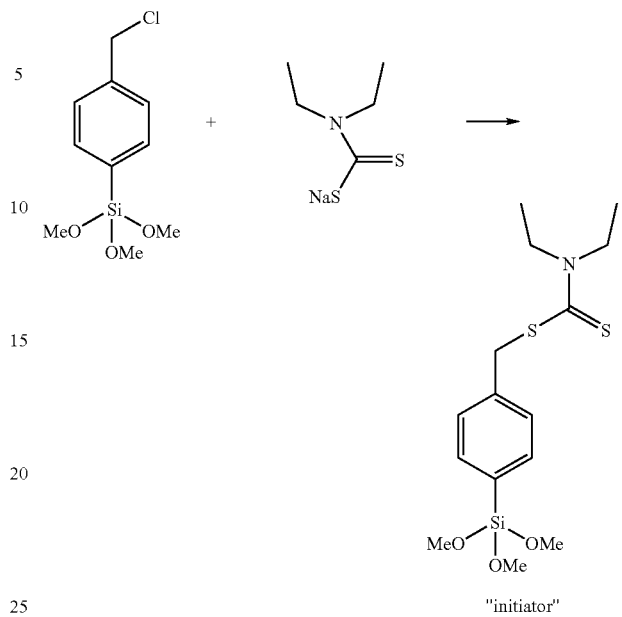

It is to be noted that when preparing a solution with a dummy or spacer molecule, p-(chloromethyl)phenyltrimethoxysilane and phenyltrimethoxysilane (shown below) are mixed together at the beginning of the process. The sodium salt is then introduced in a slight excess compared to the p-(chloromethyl) derivative.

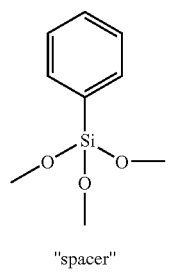

"spacer"

2—Surface Grafting of Initiator:

The crude product was poured into a 500 ml beaker containing 10 wafers. Non-anhydrous THF was then added to ensure complete coverage of the wafers with the solution (the total volume after the additional THF was added being about 500 ml). Wafers were left in contact with the solution for about two days at room temperature in a dessicator (or, alternatively, the beaker is covered with aluminum foil), in order to avoid evaporation of the solvent. Afterward, the wafers were removed from the beaker, rinsed with dichloromethane, and then dried under a flow of inert gas (e.g., nitrogen or argon).

It is to be noted that when the wafers are removed from the solution and rinsed, they are not wiped or touched with human hands. Additionally, rinsing or drying (under a gas stream) is not done perpendicular to the surface (in order to avoid etching of the surface).

3—Synthesis of Polymer Brushes:

The once removed from the above solution and dried, each wafer was position so that it was exposed at approximately 10 cm from the UV source (about 365 or 366 nm).

For irradiation, the wafers were placed in a beaker and immersed in a degassed solution of monomer (i.e., a bulk polymerization was performed), so that the surface was covered by at least about 2 mm of solution. The oxygen concentration was kept as low as possible during the process (i.e., less than about 2 ppm). When degassing the monomer (DMA), the liquid was introduced in a round bottom flask and degassed under vacuum thoroughly. The flask was then sealed under vacuum and introduced in the antechamber of the glove box.

After the reaction was complete, the wafers were removed from the irradiation source and rinsed with dichloromethane. The surface was then dried with a flow of nitrogen or argon.

Example 21

1—Synthesize of Poly(t-butylacrylamide)-b-poly(N,N-dimethylacrylamide)

A solution of t-butyl acrylamide in dimethylformide was prepared (3 g, t-butyl acrylamide dissolved in 15 cc DMF), and then poured on a modified silicon wafer (3 inches in diameter) to insure total coverage of the surface by the solution during the irradiation. The surface was then irradiated for 30 minutes at 366 nm, washed with acetone and dichloromethane, and then dried under an inert gas stream. The resulting thickness was analyzed by ellipsometry and found to be 100 angstroms.

The wafer was then immersed in N,N-dimethylacrylamide and irradiated further at 366 nm for 30 minutes. After rinsing and drying the surface (as described above), the final thickness was found to be 1400 angstroms (as determined by ellipsometry).

2—Stability Test

The impact of a hydrophobic layer on the substrate surface was investigated by exposing two different polymer brush surfaces to a sodium hydroxide solution (about 10 mmol) for about 15 minutes. The first brush contained a hydrophobic layer of t-butyl acrylamide (log P about 1.02) on the surface (about 100 angstroms thick), as well as a second water-soluble or water-dispersible layer (about 1300 angstroms thick) of dimethyl acrylamide (log P about −0.13). For purposes of comparison, a second brush was tested having only a water-soluble or water-dispersible layer of dimethyl acrylamide (about 1220 angstroms thick).

After treatment, the surfaces were rinsed and dried (as described above), and then the overall polymer thickness of each brush was again measured. For the first, the total or overall thickness was reduced from about 1400 angstroms to about 1230 angstroms, about a 12% reduction. In comparison, the total or overall thickness of the second brush was reduced from about 1220 angstroms to about 730 angstroms, about a 40% reduction. (It is to be noted that each thickness is the average of three measurements for each brush.) From these results, it is clear that the hydrophobic layer provides significant protection against the basic solution (the decrease in thickness indicating a decrease in density because, as the chains become less density, they are able to pack more tightly, thus reducing thickness).

Example 22

Preparation of "Pre-activated" Monomers

1—(a) Synthesis of N-hydroxysuccinimidyl Acrylate (C):

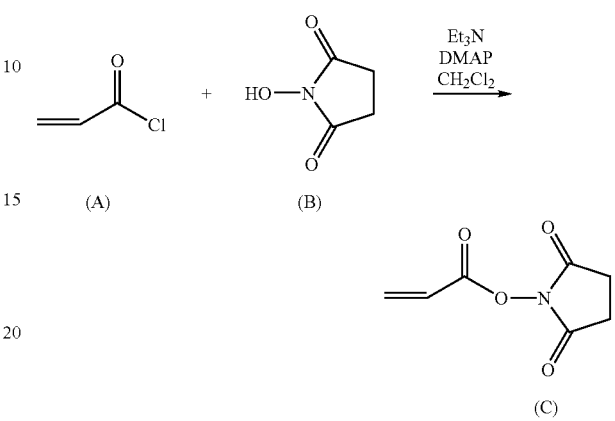

In a round bottom flask, 10 g (86.9 mmol) of N-hydroxysuccinimide (B) was dissolved in 60 ml of anhydrous $CH_2Cl_2$. The reaction was chilled to 0° C. with an ice bath. A solution of 8.26 g (91.3 mmol) acryloyl chloride (A) in 30 ml of $CH_2Cl_2$ was then slowly added from a dropping funnel, followed by the addition of DMAP (50 mg). A solution of $Et_3N$ (9.65 gr, 95.6 mmol) in 30 ml of $CH_2Cl_2$ was then added drop-wise. The reaction was stirred at 0° C. for 1 hr, and at RT for 3 hr. The organic solution was washed 2 times with water and 1 time with brine, and then dried with $MgSO_4$. After filtration, the filtrate was evaporated to dryness. The residue was purified by flash chromatography using ether as the eluant, followed by recrystallization from ether/hexane. The yield of the final product was 54%.

1—(b) Synthesis of 2-(methacryloyloxy)ethylamino N-succinimidyl carbamate (F)

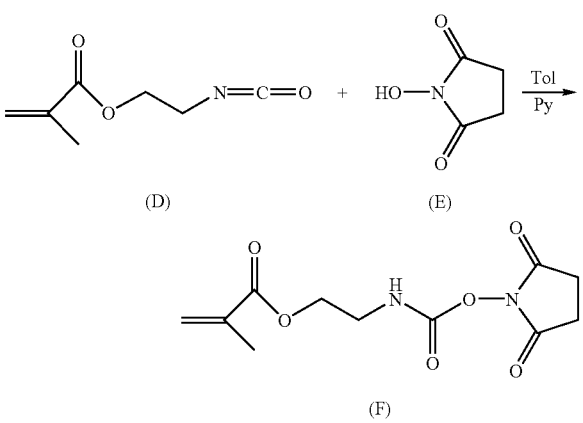

To an oven dried round bottom flask is added 815 mg (7.08 mmol) of N-hydroxysuccinimide (E). The flask was closed with a septum and flushed with argon. Anhydrous toluene (20 ml) was added with a syringe, followed by 1 ml (7.08 mmol, 1.098 g) of isocyanoethyl methacrylate (D). Pyridine (0.57 ml) was then added drop-wise. The mixture was stirred for 2 hr at RT. Hexane was added until an oil (or solid) separated. The supernatant was discarded. The oil or solid was redissolved in dichloromethane:ether (1:2). Hexane was added until the solution started to get cloudy. The flask was then left in the fridge overnight.

White crystals where collected by filtration. A second batch was then obtained by adding more hexane to the remaining solution. (Yield: 98%.)

2—Polymer Brush Preparation:

(a) Substrate Surface Preparation for Hydrosilylation:

In order to prepare the substrate surfaces (i.e., glass slides) for use, the substrates were immersed a series of solutions. Specifically, the substrates were immersed sequentially in: (a) a nanostrip solution for 15 minutes; (b) a 10% NaOH solution at 70° C. for 3 minutes; and, (c) a 1% aqueous solution of hydrochloric acid for 3 minutes (the slides being immersed in deionized water after being removed from each solutions and before being immersed in the subsequent solution). Afterward, the substrates were allowed to air dry, and then they were place in a vacuum oven over night (at a temperature of about 100° C.).

(b) Hydrosilylation of Initiator and Dummy Molecules:

To begin, all of the glassware employed in the hydrosilylation process was oven dried. Different ratios of initiator to dummy were then weighed into the reaction vessel, which were purged with Ar gas continuously. In this instance, for 10 slides a total of 3.2 mmoles (mmoles initiator plus mmoles dummy) were used. For example, using a 50:50 I:D ratio, the appropriate molar ratio of initiator to dummy is 1.6 mmoles initiator to 1.6 mmoles dummy (0.677 g initiator to 0.282 g dummy). Referring to the table provide below, three different ratios of I/D were investigated: I:D=12.5/87.5, 50:50, and 75:25.

| Molecule | I/D = 12.5/87.5 | I/D = 50/50 | I/D = 75/25 |
|---|---|---|---|
| Initiator (I) | 0.169 g | 0.677 g | 1.015 g |
| Dummy (D) | 0.493 g | 0.282 g | 0.141 g |

Once each initiator to dummy combination was weighed into the appropriate reaction vessel, 15 ml of $(Cl)_3SiH$ were added to each vessel. A platonic solution (2.5 ml) was then added to each vessel (in this case, a solution comprising 15 mg $HPtCl_6$ in 1.25 ml anhydrous ethanol and 1.25 ml anhydrous ethylene glycol dimethylether was used). The reaction vessels were sealed tightly, covered with aluminum foil and stirred overnight. The following day, 5 ml of anhydrous toluene were added, and then excess $(Cl)_3SiH$ was removed under pressure and mild heat (using a rotavap). Anhydrous $CH_2Cl_2$ (20 ml) was added, and then solvent removal was continued until the toluene level was reached (again using the rotavaped).

The resulting solution was filter through a syringe filled half way with anhydrous $Na_2SO_4$, and then 20 ml $CH_2Cl_2$ were added. Again, the $CH_2Cl_2$ was removed until the toluene level was reached (using the rotavap). The resulting product in toluene was stored under Ar gas for further use in bonding onto glass slides.

(c) Surface-bonding of Initiator and Dummy Molecules onto Glass Slide Substrates:

In a dry glove box, the substrates (i.e., 5 glass slides) which were cleaned as described above were placed in the silylation chamber. Toluene (20 ml) was added to the chamber, followed by 5 ml of one of the modified initiator and dummy solutions (i.e., hydrosilylation solutions) described above, and then 5 ml of $(Et)_3N$ (99.8% solution).

The reaction solution was covered and left to stand in the glove box for 72 hours with gentle shaking. After this time had elapsed, the slides were removed from the solution and glove box, and then washed with acetone and DMF solvent. Finally, the slides were allowed to air dry.

(d) Polymer Brushes on Glass Slides:

Reaction solutions were prepared inside the glove box and then glassware was oven dried. Using a round petri dish containing PEEK racks with 6 modified glass slides as described above (two glass slides from each I/D ratio), 31.2 g of dimethyl acrylamide (DMA) was added, followed by 13.0 g of N-hydroxysuccinimidyl acrylate (NHSA) (25% molar ratio to DMA), $3.19 \times 10^{-3}$ g of initiator-control agent adduct, $0.15 \times 10^{-3}$ g of nitroxide (same nitroxide as that employed in Experiment 2, above), and finally 60 ml of dimethyl foramide (DMF) distilled over sodium metal. The reaction vessel was tightly sealed and then heated to 126° C. in oil bath for 9 to 10 hours (heating was continued until the target molecular weight of about 50,000 was reach, the reaction being followed by GPC measurement).

Once the reaction was complete, the glass slides were washed with anhydrous DMF inside the glove box three times over a period of 30 hours, and then stored in a dark (wht a desiccant).

Three different molar ratios of NHS monomer to DMA monomer were studied: 25%, 10% and 5%.

| NHS % | NHS(g) | DMA(g) | Adduct(g) | Nitroxide(g) | MF |
|---|---|---|---|---|---|
| 25 | 13.0 | 31.2 | $3.19 \times 10^{-3}$ | $0.12 \times 10^{-3}$ | 55 ml |
| 10 | 5.8 | 35.0 | $3.02 \times 10^{-3}$ | $0.10 \times 10^{-3}$ | 60 ml |
| 5 | 4.2 | 50.0 | $3.73 \times 10^{-3}$ | $0.13 \times 10^{-3}$ | 70 ml |

(e) Quantification of Linking Efficiency of Activated Slides:

This method was used to optimize the activation process and brush parameters (brush density, molecular weight and functionality), and quantify covalently attached oligonucleotides/DNA (probes). DNA solutions are printed on the activated slides and linking efficiency is measured by using a fluorescence scanner. (Note that results are further illustrated by the Tables and Graphs presented in FIGS. 10a through 10d.)

Preparation of DNA printing solution: Solutions of probe oligo (Cy3-TAATGAAACTGGATGTAGAGATAGAT-GAATGTTGATAGCGACGAGCGAT-NH2 3') were made at different concentrations (10, 25, 50 and 100 M) in a printing buffer (150 mM sodium phosphate, pH 8.5).

Printing and coupling DNA: Activated slides or slides containing activated monomers were taken out of the desiccator. DNA solution was printed on activated slides to form microarrays by using an internal facility for spotting arrays. The printed slides are placed in a slide storage box and the uncovered storage box is set in a humidification chamber, which is maintained at 80% relative humidity. The slides are allowed to incubate overnight.

Post-coupling processing: The coupled slides are placed in a slide rack and residual reactive groups are blocked by using 10 ml per slide of pre-warmed blocking solution (50 mM ethanolamine, 0.1 M Tris, pH 9) at 50° C. for 20 minutes. Prior to warming, SDS (sodium dodecyl sulfate) is added to the blocking solution to a final concentration of 0.1%. After the blocking solution is discarded the slides are rinsed with distilled water, dried under $N_2$ flow and stored in a dark, dry place (in a slide storage box inside a desiccator).

The DNA linked to the slide is quantified by using a GSI Lumonics scanner. The system is operated at ambient temperature and fluorescence is measured using a 570-nm band-pass emission filter and 550-nm band-pass excitation filter in conjunction with a HeNe laser (543.5 nm). ScanArray™ software is used for data acquisition and the images are analyzed using QuantArray™ to quantify the fluorescence of each spot.

Example 23

Preparation of Brush for Large Probe Attachment

The procedure is carried out in a dry box, with an oxygen level lower than 2 ppm. The activated glass slides (initiator to dummy ratio of 2% to 98%) are placed in a flat container. A mixture of dimethylacrylamide (DMA) and N-methyl-N-2-hydroxyethylacrylamide (DMA-OH) is prepared and poured slowly over the surfaces, so that all of the slides are completely covered with at least 2 mm of the solution. UV irradiation (366 nm) perpendicular to the surface is then carried out for 60 minutes. The source is positioned 10 cm over the surface. The slides are then soaked in dichloromethane overnight. Afterward, the slides are rinsed with dichloromethane, and dried with Ar flow. Elipsometry measurements show a thickness of 50 angstroms. [OH] density: 46 pmoles/cm$^2$.

Example 24

Preparation of Brushes Having Functional Sites Which do not Require Activation for Probe Attachment Preparation of DMA/GMA Polymer Brushes The procedure is carried out in a dry box, with an oxygen level lower than 2 ppm. The Si wafers or glass slides, previously treated with the initiator and dummy solutions as shown in Example 20-2, are placed in a flat container. A mixture of DMA and GMA is prepared and poured slowly over the activated surfaces (prepared as described in example 20), so that the surface of each slide is completely covered with at least 2 mm of the solution. UV irradiation (366 nm) perpendicular to the surface is then carried out. The source is positioned 10 cm over the surface. After the required time, the source is turned off, and the wafers are soaked in dichloromethane overnight. Afterward, the wafers are rinsed with dichloromethane, and dried with an Ar flow.

Following this process, various slides were prepared having different initiator to spacer or dummy ratios (I/D ratio), ratios of GMA to DMA, and irradiation times. A few combinations are indicated in the table, below.

| I/D ratio | GMA/DMA ratio | Irradiation time | Brush Thickness |
|---|---|---|---|
| 50/50 | 10/90 | 15 min | 289 Å |
| 15/85 | 5/95 | 30 min | 170 Å |

Example 25

Synthesis of Polymer Brushes by the UV Method

Synthesis of the initiator/surface modification: The preparation of the initiator and spacer, as well as the derivatization of the substrate surface using this, was the same as disclosed above in Example 20.

Results on silicon wafers: Reactions were performed in a glove box with low amount of oxygen (about 1 ppm or less). Each silicon wafer was immersed in distilled dimethylacrylamide (1 ml). Some functional monomers (shown below) were used in random copolymerizations. Different amounts of the dummy molecule (structure above) were used in order to tune the polymer chain densities.

The surfaces were then placed about 10 cm from a 365–366 nm UV lamp and irradiated for the required time at room temperature. After polymerization, the samples were immersed in 50 ml of dichloromethane overnight to remove homopolymers that may have formed in solution. Finally, the surfaces were dried under a prepurified N$_2$ flow at room temperature. The surfaces were then characterized by ellipsometry measurements.

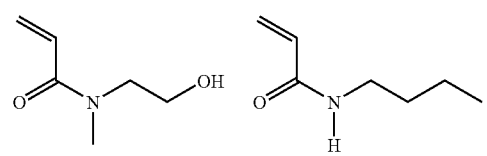

| Ratio: D/I | Functional monomer % (w/w) | Time of irradiation (mn) | Thickness by ellipsometry |
|---|---|---|---|
| 0/0 | 0 | 15 | — |
| 0/0 | 0 | 30 | — |
| 0/0 | 0 | 50 | — |
| 0/100 | 0 | 0 | 12 |
| 0/100 | 0 | 15 | 620 |
| 0/100 | 0 | 30 | 1210 |
| 0/100 | 0 | 50 | 2040 |
| 0/100 | 15 (H-alc) | 30 | 1094 |
| 0/100 | 23 (Me-alc) | 30 | 1221 |
| 75/25 | 0 | 30 | 329.17 |
| 50/50 | 0 | 30 | 611.8 |
| 25/75 | 0 | 30 | 940 |

Synthesis of Block Copolymers (poly(tert butyl acrylamide)-b-poly(N,N-dimethylacrylamide)). Further to Example 21, above, synthesis of different block copolymers on a silicon wafer, using poly(tert-butylacrylamide)-b-poly(N,N-dimethylacrylamide) was performed, as indicated below.

| Initiator/Dummy | C1 (g/cm$^3$) | T1 (min) | 1 (A) | T2 (min) | 2 (A) |
|---|---|---|---|---|---|
| 100/0 | 0.25 | 0 | 25 | 60 | 1800 |
| 100/0 | 0.25 | 0 | 25 | 60 | 1800 |
| 100/0 | 0.25 | 0 | 25 | 60 | 1840 |
| 100/0 | 0.25 | 0 | 25 | 60 | 1820 |
| 100/0 | 0.25 | 15 | 55 | 60 | 1800 |
| 100/0 | 0.25 | 15 | 55 | 60 | 2000 |
| 100/0 | 0.25 | 15 | 55 | 60 | 1970 |
| 100/0 | 0.25 | 15 | 55 | 60 | 1970 |
| 100/0 | 0.25 | 30 | 145 | 60 | 2000 |
| 100/0 | 0.25 | 30 | 145 | 60 | 2000 |
| 100/0 | 0.25 | 30 | 145 | 60 | 2100 |
| 100/0 | 0.25 | 45 | 220 | 60 | 1800 |
| 100/0 | 0.25 | 45 | 220 | 60 | 2010 |

-continued

| Initiator/Dummy | C1 (g/cm³) | T1 (min) | 1 (A) | T2 (min) | 2 (A) |
|---|---|---|---|---|---|
| 100/0 | 0.25 | 45 | 220 | 60 | 2000 |
| 100/0 | 0.25 | 45 | 220 | 60 | 2000 |

(Table Key:
C1: initial concentration of tert butyl acrylamide in dimethyl formamide;
T1: Time of irradiation to synthesize the first block (poly tert butyl acrylamide) of the polymer brush;
1: Thickness of the first block (poly tertbutyl acrylamide) of polymer brush measured by ellipsometry;
T2: Time of irradiation to synthesize the second block poly(dimethyl acrylamide) of the polymer brush; and,
2: Thickness of the second block poly(dimethyl acrylamide) of polymer brush measured by ellipsometry.)

Synthesis of Block Copolymers Polystyrene-block-Poly(dimethyl acrylamide): Synthesis of different block copolymers on a silicon wafer Polystyrene-block-Poly(dimethyl acrylamide).

| Initiator/Dummy | T1 (min) | 1 (A) | T2 (min) | 2 (A) |
|---|---|---|---|---|
| 100/0 | 0 | 17 | 60 | 2000 |
| 100/0 | 0 | 17 | 60 | 1450 |
| 100/0 | 0 | 17 | 60 | 1430 |
| 100/0 | 0 | 17 | 60 | 1450 |
| 100/0 | 15 | 65 | 60 | 1420 |
| 100/0 | 15 | 65 | 60 | 1412 |
| 100/0 | 15 | 65 | 60 | 1450 |
| 100/0 | 15 | 65 | 60 | 1700 |
| 100/0 | 30 | 120 | 60 | 1402 |
| 100/0 | 30 | 120 | 60 | 1330 |
| 100/0 | 30 | 120 | 60 | 1350 |
| 100/0 | 30 | 120 | 60 | 1430 |
| 100/0 | 60 | 260 | 60 | 1300 |
| 100/0 | 60 | 260 | 60 | 1312 |
| 100/0 | 60 | 260 | 60 | 1300 |
| 100/0 | 60 | 260 | 60 | 1250 |

(Table Key:
T1: Time of irradiation to synthesize the first block (Polystyrene) of the polymer brush;
1: Thickness of the first block (Polystyrene) of polymer brush measured by ellipsometry;
T2: Time of irradiation to synthesize the second block poly(dimethyl acrylamide) of the polymer brush;
2: Thickness of the second block poly(dimethyl acrylamide) of polymer brush measured by ellipsometry.)

It is to be understood that the above description is intended to be illustrative and not restrictive. Many embodiments will be apparent to those of skill in the art upon reading the above description. The scope of the invention should therefore be determined not with reference to the above description, but should instead be determined with reference to the appended claims, along with the full scope of equivalents to which such claims are entitled.

The disclosures or references of all articles, patents and references, including patent applications and publications, are incorporated herein by reference for all purposes.

Other embodiments are within the following claims.

We claim:

1. A polymer brush for binding a molecule in an aqueous sample in an assay, the brush comprising a substrate surface, a hydrophobic layer comprising hydrophobic polymer chain segments attached to the substrate surface and having a dry thickness of at least about 50 angstroms, and a hydrophilic layer attached to the hydrophobic layer containing functional groups for the attachment of a probe for binding the molecule.

2. The polymer brush of claim 1 wherein the hydrophobic layer has a dry thickness of at least about 100 angstroms.

3. The polymer brush of claim 1 wherein the hydrophobic layer has a dry thickness of at least about 1000 angstroms.

4. The polymer brush of claim 1 wherein the hydrophobic layer has a dry thickness of at least about 2000 angstroms.

5. The polymer brush of claim 1 wherein said hydrophobic polymer chain segments comprise repeat units derived from a hydrophobic monomer having a log P value of at least about 1.

6. The polymer brush of claim 1 wherein, in addition to said hydrophobic polymer chain segments, spacer molecules are also attached to the substrate surface, the ratio of said hydrophobic polymer chain segments to the sum of hydrophobic polymer chains segments and spacer molecules ranging from about 0.2:1 to about 0.8:1.

7. The polymer brush of claim 1 wherein at least a portion of the hydrophobic polymer chain segments are crosslinked to other hydrophobic polymer chain segments in the hydrophobic layer.

8. The polymer brush of claim 1 wherein the hydrophilic layer comprises water-soluble or water-dispersible polymer chain segments having groups for the attachment of a probe, wherein an end of each segment is attached to the hydrophobic layer, and further wherein said water-soluble or water-dispersible segments have a weight average molecular weight of at least 1,000.

9. The polymer brush of claim 8 wherein the water-soluble or water-dispersible segments have a weight average molecular weight of at least 1,000 but no more than 5,000,000.

10. The polymer brush of claim 1 wherein the hydrophilic layer comprises water-soluble or water-dispersible polymer chain segments having groups for the attachment of a probe, said segments comprising repeat units derived from a water-soluble or water-dispersible monomer having a log P value of less than about 1.

11. The polymer brush of claim 1 wherein the hydrophilic layer comprises water-soluble or water-dispersible polymer chain segments having groups for the attachment of a probe, said segments comprising repeat units derived from a water-soluble or water-dispersible monomer having a log P value of less than about 0.1.

12. The polymer brush of claim 10 wherein in an absolute difference between a log P value of the hydrophobic monomers and the water-soluble or water-dispersible monomers is at least about 1.

13. The polymer brush of claim 10 wherein in an absolute difference between a log P value of the hydrophobic monomers and the water-soluble or water-dispersible monomers is at least about 2.

14. The polymer brush of claim 1 wherein the hydrophobic layer comprises hydrophobic polymer chain segments, one end of each of said hydrophobic segments being attached to the substrate surface, and further wherein the hydrophilic layer comprises water-soluble or water-dispersible polymer chain segments having groups for the attachment of a probe, one end of each of said water-soluble or water-dispersible segments being attached to the hydrophobic layer, the ratio of water-soluble or water-dispersible segments to hydrophobic segments being less than about 1:1.

15. The polymer brush of claim 1 wherein the hydrophilic layer has a dry thickness ranging from about 10 angstroms to about 2000 angstroms.

16. The polymer brush of claim 1 additionally comprising a probe attached to the functional groups for binding the molecule.

17. The polymer brush of claim 16 wherein said groups for the attachment of a probe are capable of attaching said probe without first being subjected to a chemical treatment to activate said groups for probe attachment.

18. The polymer brush of claim 16 wherein the molecule is a biological molecule and the probe is selected from the group consisting of nucleic acids, polypeptides, peptide nucleic acids, markers, cells, elastin, collagen, carbohydrates, enzymes, lipids, phospholipids, hormones, drug targets, phosphates, and metal ions.

19. The polymer brush of claim 16 wherein said functionalized groups are selected from the group consisting of hydroxy groups, amino groups, carboxylic acids, carboxylic acid derivatives, and thiols.

20. The polymer brush of claim 1 wherein the hydrophilic layer is substantially free of crosslinks.

21. A polymer brush for binding a molecule in an aqueous sample in an assay, the brush comprising a substrate surface having a polymer layer thereon, said polymer layer comprising a first hydrophobic layer attached to the substrate surface, and a second hydrophilic layer attached to the hydrophobic layer containing groups for the attachment of a probe for binding the molecule, said brush being characterized in that said hydrophobic polymer layer has a minimum thickness such that, upon being immersed in a 10 mmolar sodium hydroxide solution for about 15 minutes, the polymer layer thickness is reduced by less than about 40%.

22. The polymer brush of claim 21 wherein the polymer layer thickness is reduced by less than about 20%.

23. The polymer brush of claim 21 wherein the polymer layer thickness is reduced by less than about 10%.

24. The polymer brush of claim 21 wherein the hydrophobic layer has a dry thickness of at least about 100 angstroms.

25. The polymer brush of claim 21 wherein the hydrophobic layer has a dry thickness of at least about 1000 angstroms.

26. The polymer brush of claim 21 wherein the hydrophilic layer has a dry thickness ranging from about 10 angstroms to about 2000 angstroms.

27. The polymer brush of claim 21 wherein the hydrophilic layer comprises water-soluble or water-dispersible intermediate segments having a weight average molecular weight of at least about 1000, and one or more functional groups capable of reacting with a probe selective for the molecule.

28. The polymer brush of claim 27 wherein said functionalized groups are selected from the group consisting of hydroxy groups, amino groups, carboxylic acids, carboxylic acid derivatives, and thiols.

29. The polymer brush of claim 28 wherein the molecule is a biological molecule and the probe is selected from the group consisting of nucleic acids, polypeptides, peptide nucleic acids, markers, cells, elastin, collagen, carbohydrates, enzymes, lipids, phospholipids, hormones, drug targets, phosphates, and metal ions.

30. The polymer brush of claim 1 wherein the hydrophobic polymer chain segments are covalently bound to the substrate surface.

31. The polymer brush of claim 30 wherein the hydrophilic layer comprises water-soluble or water-dispersible polymer chain segments, and further wherein an end of each of said hydrophilic polymer chain segments is covalently bound to a hydrophobic polymer chain segment.

32. The polymer brush of claim 21 wherein the hydrophobic layer comprises hydrophobic polymer chain segments, and further wherein said polymer chain segments are covalently bound to the substrate surface.

33. The polymer brush of claim 32 wherein the hydrophilic layer comprises water-soluble or water-dispersible polymer chain segments, and further wherein an end of each of said hydrophilic polymer chain segments is covalently bound to a hydrophobic polymer chain segment.

* * * * *